(12) United States Patent
Li et al.

(10) Patent No.: US 10,994,025 B2
(45) Date of Patent: May 4, 2021

(54) ARGONAUTE PROTEIN-DOUBLE STRANDED RNA COMPLEXES AND USES RELATED THERETO

(71) Applicant: Massachusetts Institute of Technology, Cambridge, MA (US)

(72) Inventors: Jiahe Li, Medford, MA (US); Paula T. Hammond, Newton, MA (US); Yanpu He, Cambridge, MA (US); Wade Wang, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 16 days.

(21) Appl. No.: 15/977,778

(22) Filed: May 11, 2018

(65) Prior Publication Data

US 2018/0326092 A1 Nov. 15, 2018

Related U.S. Application Data

(60) Provisional application No. 62/505,430, filed on May 12, 2017.

(51) Int. Cl.
| | |
|---|---|
| *A61K 48/00* | (2006.01) |
| *C12N 15/113* | (2010.01) |
| *A61K 9/00* | (2006.01) |
| *A61K 38/17* | (2006.01) |
| *A61K 47/42* | (2017.01) |
| *C12N 15/11* | (2006.01) |

(52) U.S. Cl.
CPC .......... *A61K 48/005* (2013.01); *A61K 9/0019* (2013.01); *A61K 38/17* (2013.01); *A61K 47/42* (2013.01); *A61K 48/0075* (2013.01); *C12N 15/111* (2013.01); *C12N 15/113* (2013.01); *C12N 2310/121* (2013.01); *C12N 2310/122* (2013.01); *C12N 2310/14* (2013.01); *C12N 2310/141* (2013.01); *C12N 2310/31* (2013.01); *C12N 2310/333* (2013.01); *C12N 2310/335* (2013.01); *C12N 2310/336* (2013.01); *C12N 2310/3341* (2013.01); *C12N 2320/35* (2013.01)

(58) Field of Classification Search
None
See application file for complete search history.

(56) References Cited

U.S. PATENT DOCUMENTS

| | | | |
|---|---|---|---|
| 7,732,417 B2 | 6/2010 | Beach et al. | |
| 8,951,983 B2* | 2/2015 | Hornstein | C12N 5/0676 514/44 A |
| 9,476,044 B2 | 10/2016 | Tuschl et al. | |
| 2006/0141600 A1* | 6/2006 | Joshua-Tor | C07K 14/47 435/199 |
| 2014/0308274 A1* | 10/2014 | Bader | A61K 31/713 424/133.1 |
| 2014/0328931 A1* | 11/2014 | Hammond | C12N 15/113 424/490 |

FOREIGN PATENT DOCUMENTS

| | | |
|---|---|---|
| WO | WO-2007/048629 A2 | 5/2007 |
| WO | WO-2010/033225 A2 | 3/2010 |
| WO | WO-2011/133889 A2 | 10/2011 |
| WO | WO-2015/138636 A1 | 9/2015 |
| WO | WO-2016161375 A2 | 10/2016 |

OTHER PUBLICATIONS

Meister et al. Mol. Cell 185-197 (Year: 2004).*
Lin et al. Journal of Controlled release 235, 268-275 (Year: 2016).*
Lin et al. Journal of Controlled Release, 235, Supplementary methods, pp. 1-10 (Year: 2016).*
Li et al. ACS Nano 11, 2531-2544 (Year: 2017).*
Christian et al., "Passenger-Strang Cleavage Facilitates Assembly of siRNA into Ago2-Containing RNAi Enzyme Complexes," Cell, 123(4):608-620 (2005).
Ferreira et al., "Argonaute-2 Promotes miR-18a Entry in Human Brain Endothelial Cells," Journal of the American Heart Association, 3(3):e000968-e000968 (2014).
International Search Report and Written Opinion for International Application No. PCT/US2018/032401 dated May 11, 2018.
Lafont et al., "Activated Platelets can Deliver mRNA Regulatory Ago2bulletmicroRNA Complexes to Endothelial Cells Via Microparticles," Blood, 122(2):253-261 (2013).
Liu et al., "Dicer-Independent Processing of Short Hairpin RNAs," Nucleic Acids Research, 41(6):3723-3733 (2013).
Matsui et al., "Argonaute 2-Dependent Regulation of Gene Expression by Single-Stranded miRNA Mimics," Molecular Therapy: The Journal of the American Society of Gene Therapy, 24(5):946-955 (2016).
Prud'homme et al., "Neuropilin-1 is a Receptor for Extracellular miRNA and AGO2/miRNA Complexes and Mediates the Internalization of miRNAs that Modulate Cell Function," Oncotarget, 7(42):68057-68071 (2016).
Salzman et al., "miR-34 Activity is Modulated Through 5'-end Phosphorylation in Response to DNA Damage," Nature Communications, 7:10954 (2016).
Tan et al., "Expanded RNA-Binding Activities of Mammalian Argonaute 2," Nucleic Acids Research, 37(22):7533-7545 (2009).

* cited by examiner

*Primary Examiner* — Brian Whiteman

(74) *Attorney, Agent, or Firm* — Foley Hoag LLP

(57) ABSTRACT

The invention relates to methods of improving efficacy and enhancing silencing of target genes using Ago2 protein-dsRNA complex (RNP) of the invention.

Figure 1A:
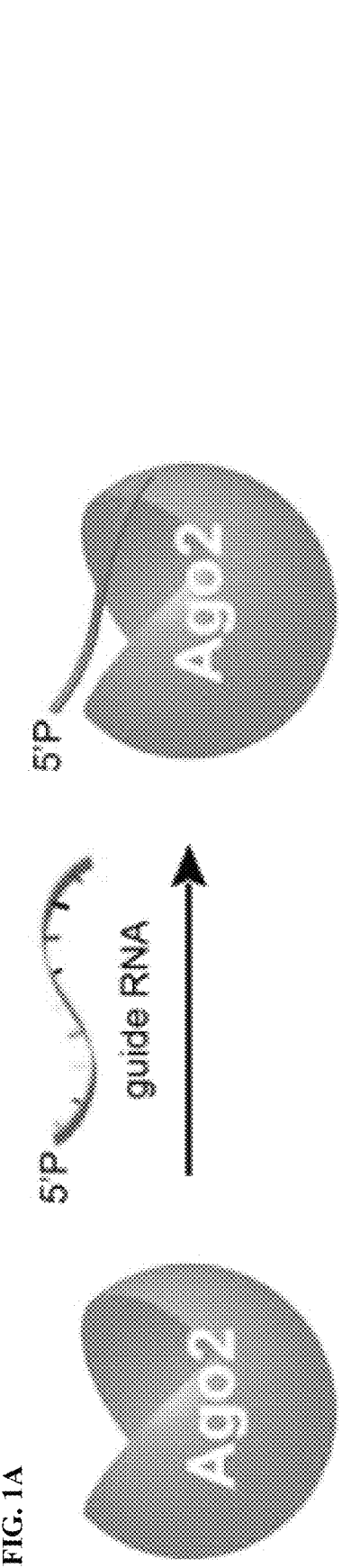

25 Claims, 57 Drawing Sheets
(50 of 57 Drawing Sheet(s) Filed in Color)
Specification includes a Sequence Listing.

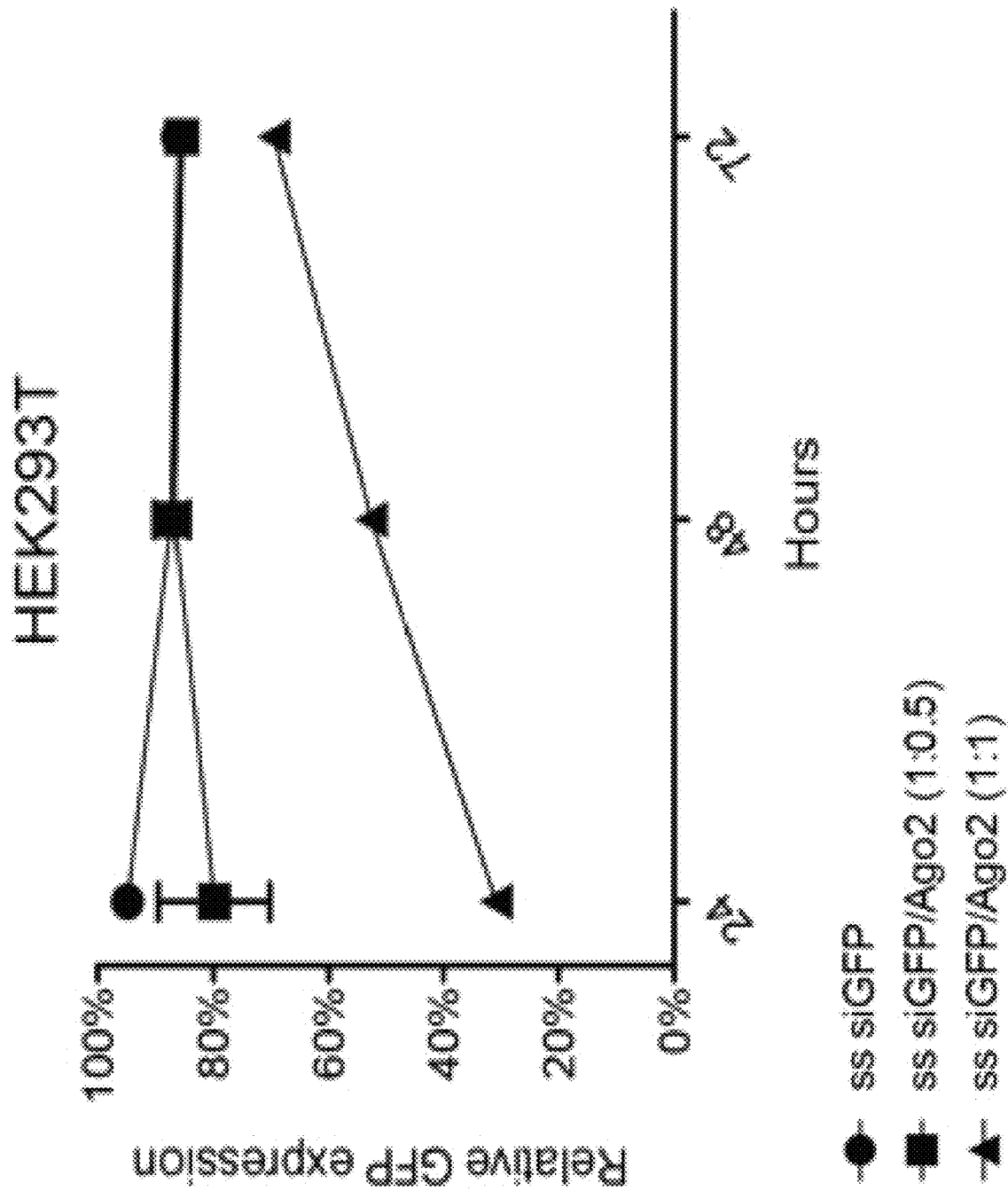

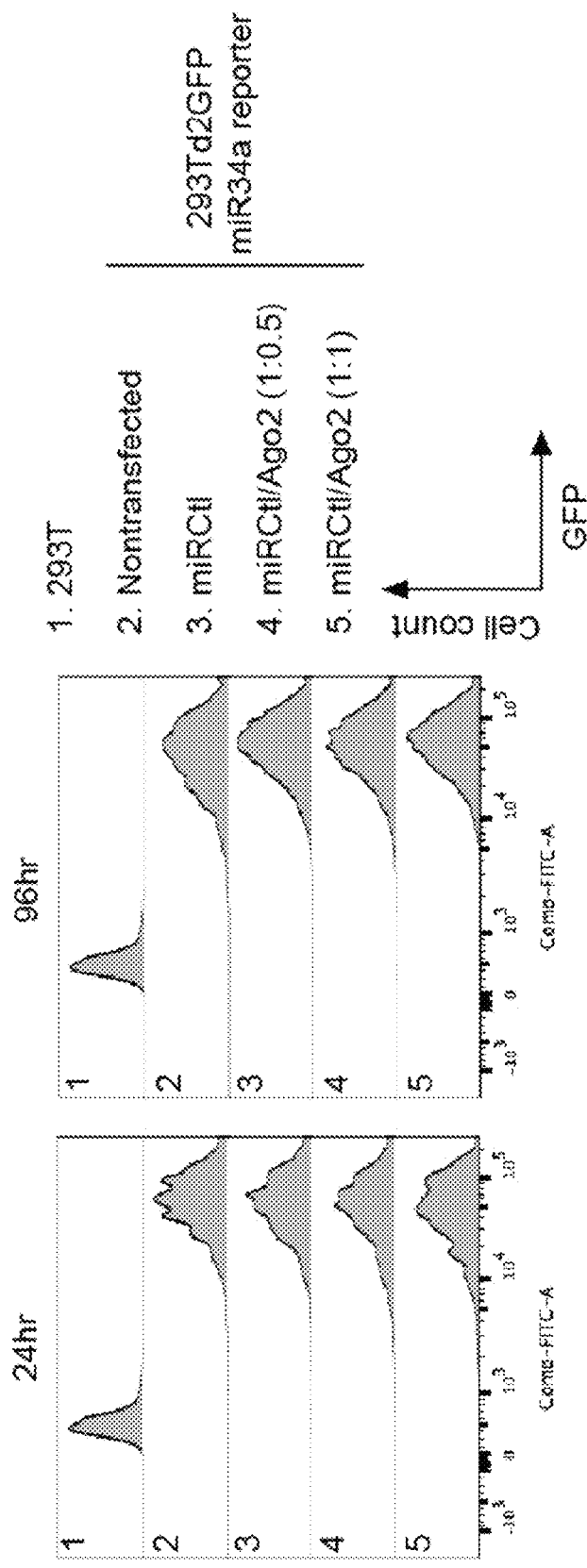
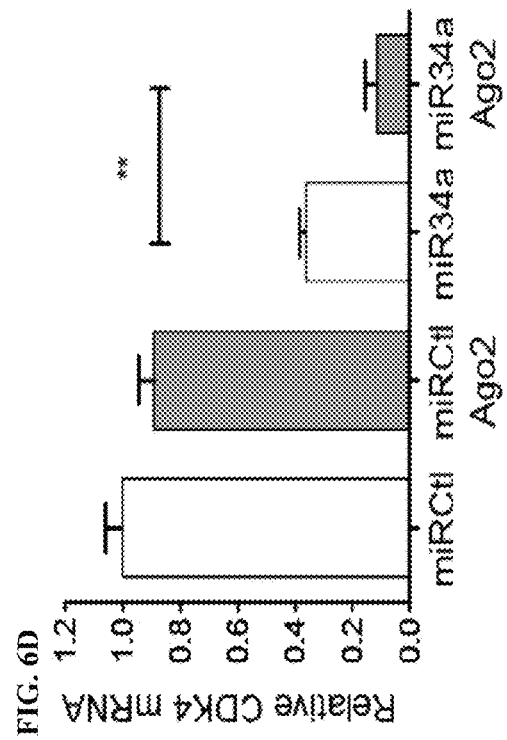
FIG. 6C
FIG. 6D

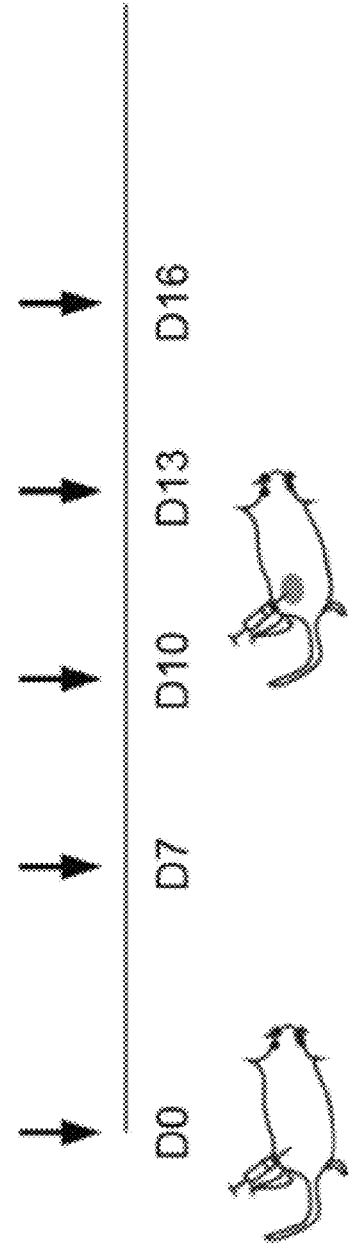
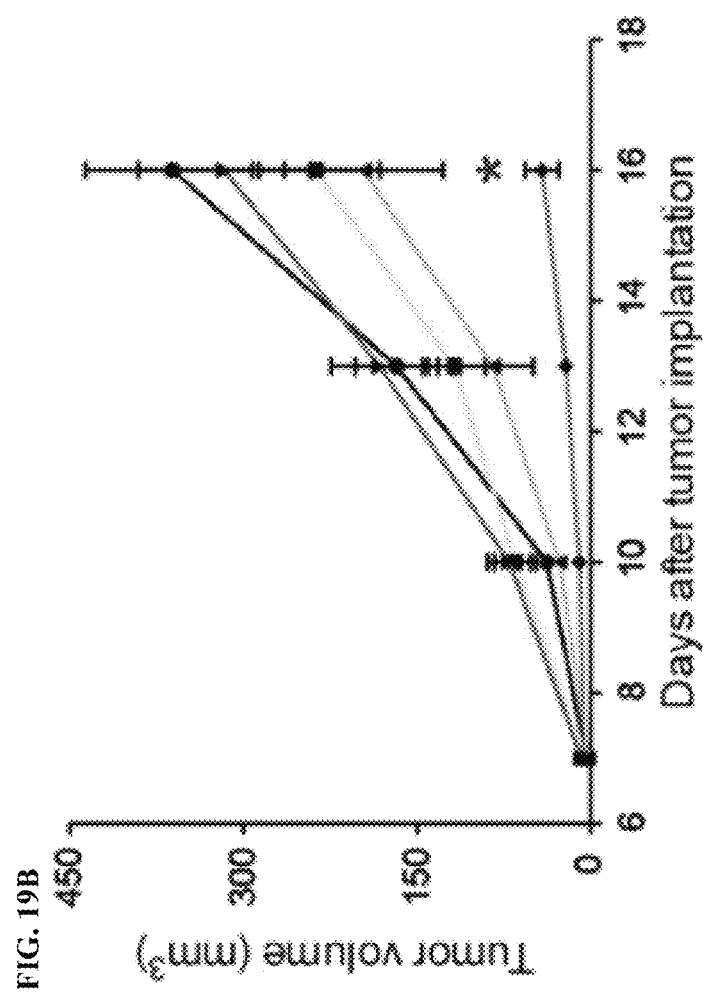
FIG. 19A
FIG. 19B

SEQUENCE LISTING

```
<160> NUMBER OF SEQ ID NOS: 24

<210> SEQ ID NO 1
<211> LENGTH: 861
<212> TYPE: PRT
<213> ORGANISM: Homo sapiens

<400> SEQUENCE: 1

Gly Ala Met Tyr Ser Gly Ala Gly Pro Ala Leu Ala Pro Pro Ala Pro
1               5                   10                  15

Pro Pro Pro Ile Gln Gly Tyr Ala Phe Lys Pro Pro Pro Arg Pro Asp
            20                  25                  30

Phe Gly Thr Ser Gly Arg Thr Ile Lys Leu Gln Ala Asn Phe Phe Glu
        35                  40                  45

Met Asp Ile Pro Lys Ile Asp Ile Tyr His Tyr Glu Leu Asp Ile Lys
    50                  55                  60

Pro Glu Lys Cys Pro Arg Arg Val Asn Arg Glu Ile Val Glu His Met
65                  70                  75                  80

Val Gln His Phe Lys Thr Gln Ile Phe Gly Asp Arg Lys Pro Val Phe
                85                  90                  95

Asp Gly Arg Lys Asn Leu Tyr Thr Ala Met Pro Leu Pro Ile Gly Arg
            100                 105                 110

Asp Lys Val Glu Leu Glu Val Thr Leu Pro Gly Glu Gly Lys Asp Arg
        115                 120                 125

Ile Phe Lys Val Ser Ile Lys Trp Val Ser Cys Val Ser Leu Gln Ala
    130                 135                 140

Leu His Asp Ala Leu Ser Gly Arg Leu Pro Ser Val Pro Phe Glu Thr
145                 150                 155                 160

Ile Gln Ala Leu Asp Val Val Met Arg His Leu Pro Ser Met Arg Tyr
                165                 170                 175

Thr Pro Val Gly Arg Ser Phe Phe Thr Ala Ser Glu Gly Cys Ser Asn
            180                 185                 190
```

-continued

Pro Leu Gly Gly Gly Arg Glu Val Trp Phe Gly Phe His Gln Ser Val
          195                 200                 205

Arg Pro Ser Leu Trp Lys Met Met Leu Asn Ile Asp Val Ser Ala Thr
210                 215                 220

Ala Phe Tyr Lys Ala Gln Pro Val Ile Glu Phe Val Cys Glu Val Leu
225                 230                 235                 240

Asp Phe Lys Ser Ile Glu Glu Gln Gln Lys Pro Leu Thr Asp Ser Gln
                245                 250                 255

Arg Val Lys Phe Thr Lys Glu Ile Lys Gly Leu Lys Val Glu Ile Thr
              260                 265                 270

His Cys Gly Gln Met Lys Arg Lys Tyr Arg Val Cys Asn Val Thr Arg
          275                 280                 285

Arg Pro Ala Ser His Gln Thr Phe Pro Leu Gln Gln Glu Ser Gly Gln
290                 295                 300

Thr Val Glu Cys Thr Val Ala Gln Tyr Phe Lys Asp Arg His Lys Leu
305                 310                 315                 320

Val Leu Arg Tyr Pro His Leu Pro Cys Leu Gln Val Gly Gln Glu Gln
                325                 330                 335

Lys His Thr Tyr Leu Pro Leu Glu Val Cys Asn Ile Val Ala Gly Gln
              340                 345                 350

Arg Cys Ile Lys Lys Leu Thr Asp Asn Gln Thr Ser Thr Met Ile Arg
          355                 360                 365

Ala Thr Ala Arg Ser Ala Pro Asp Arg Gln Glu Glu Ile Ser Lys Leu
370                 375                 380

Met Arg Ser Ala Ser Phe Asn Thr Asp Pro Tyr Val Arg Glu Phe Gly
385                 390                 395                 400

Ile Met Val Lys Asp Glu Met Thr Asp Val Thr Gly Arg Val Leu Gln
                405                 410                 415

Pro Pro Ser Ile Leu Tyr Gly Gly Arg Asn Lys Ala Ile Ala Thr Pro
              420                 425                 430

Val Gln Gly Val Trp Asp Met Arg Asn Lys Gln Phe His Thr Gly Ile
          435                 440                 445

Glu Ile Lys Val Trp Ala Ile Ala Cys Phe Ala Pro Gln Arg Gln Cys
450                 455                 460

Thr Glu Val His Leu Lys Ser Phe Thr Glu Gln Leu Arg Lys Ile Ser
465                 470                 475                 480

Arg Asp Ala Gly Met Pro Ile Gln Gly Gln Pro Cys Phe Cys Lys Tyr
                485                 490                 495

Ala Gln Gly Ala Asp Ser Val Glu Pro Met Phe Arg His Leu Lys Asn
              500                 505                 510

Thr Tyr Ala Gly Leu Gln Leu Val Val Ile Leu Pro Gly Lys Thr
          515                 520                 525

Pro Val Tyr Ala Glu Val Lys Arg Val Gly Asp Thr Val Leu Gly Met
530                 535                 540

Ala Thr Gln Cys Val Gln Met Lys Asn Val Gln Arg Thr Thr Pro Gln
545                 550                 555                 560

Thr Leu Ser Asn Leu Cys Leu Lys Ile Asn Val Lys Leu Gly Gly Val
                565                 570                 575

Asn Asn Ile Leu Leu Pro Gln Gly Arg Pro Pro Val Phe Gln Gln Pro
              580                 585                 590

Val Ile Phe Leu Gly Ala Asp Val Thr His Pro Pro Ala Gly Asp Gly
          595                 600                 605

Lys Lys Pro Ser Ile Ala Ala Val Val Gly Ser Met Asp Ala His Pro

```
                    610                 615                 620
Asn Arg Tyr Cys Ala Thr Val Arg Val Gln Gln His Arg Gln Glu Ile
625                 630                 635                 640

Ile Gln Asp Leu Ala Ala Met Val Arg Glu Leu Leu Ile Gln Phe Tyr
                645                 650                 655

Lys Ser Thr Arg Phe Lys Pro Thr Arg Ile Ile Phe Tyr Arg Asp Gly
            660                 665                 670

Val Ser Glu Gly Gln Phe Gln Gln Val Leu His His Glu Leu Leu Ala
        675                 680                 685

Ile Arg Glu Ala Cys Ile Lys Leu Glu Lys Asp Tyr Gln Pro Gly Ile
690                 695                 700

Thr Phe Ile Val Val Gln Lys Arg His His Thr Arg Leu Phe Cys Thr
705                 710                 715                 720

Asp Lys Asn Glu Arg Val Gly Lys Ser Gly Asn Ile Pro Ala Gly Thr
                725                 730                 735

Thr Val Asp Thr Lys Ile Thr His Pro Thr Glu Phe Asp Phe Tyr Leu
            740                 745                 750

Cys Ser His Ala Gly Ile Gln Gly Thr Ser Arg Pro Ser His Tyr His
        755                 760                 765

Val Leu Trp Asp Asp Asn Arg Phe Ser Ser Asp Glu Leu Gln Ile Leu
770                 775                 780

Thr Tyr Gln Leu Cys His Thr Tyr Val Arg Cys Thr Arg Ser Val Ser
785                 790                 795                 800

Ile Pro Ala Pro Ala Tyr Tyr Ala His Leu Val Ala Phe Arg Ala Arg
                805                 810                 815

Tyr His Leu Val Asp Lys Glu His Asp Ser Ala Glu Gly Ser His Thr
            820                 825                 830

Ser Gly Gln Ser Asn Gly Arg Asp His Gln Ala Leu Ala Lys Ala Val
        835                 840                 845

Gln Val His Gln Asp Thr Leu Arg Thr Met Tyr Phe Ala
850                 855                 860

<210> SEQ ID NO 2
<211> LENGTH: 859
<212> TYPE: PRT
<213> ORGANISM: Homo sapiens

<400> SEQUENCE: 2

Met Tyr Ser Gly Ala Gly Pro Ala Leu Ala Pro Pro Ala Pro Pro Pro
1               5                   10                  15

Pro Ile Gln Gly Tyr Ala Phe Lys Pro Pro Arg Pro Asp Phe Gly
            20                  25                  30

Thr Ser Gly Arg Thr Ile Lys Leu Gln Ala Asn Phe Phe Glu Met Asp
        35                  40                  45

Ile Pro Lys Ile Asp Ile Tyr His Tyr Glu Leu Asp Ile Lys Pro Glu
50                  55                  60

Lys Cys Pro Arg Arg Val Asn Arg Glu Ile Val Glu His Met Val Gln
65                  70                  75                  80

His Phe Lys Thr Gln Ile Phe Gly Asp Arg Lys Pro Val Phe Asp Gly
                85                  90                  95

Arg Lys Asn Leu Tyr Thr Ala Met Pro Leu Pro Ile Gly Arg Asp Lys
            100                 105                 110

Val Glu Leu Glu Val Thr Leu Pro Gly Glu Gly Lys Asp Arg Ile Phe
        115                 120                 125
```

```
Lys Val Ser Ile Lys Trp Val Ser Cys Val Ser Leu Gln Ala Leu His
130                 135                 140

Asp Ala Leu Ser Gly Arg Leu Pro Ser Val Pro Phe Glu Thr Ile Gln
145                 150                 155                 160

Ala Leu Asp Val Val Met Arg His Leu Pro Ser Met Arg Tyr Thr Pro
                165                 170                 175

Val Gly Arg Ser Phe Phe Thr Ala Ser Glu Gly Cys Ser Asn Pro Leu
                180                 185                 190

Gly Gly Gly Arg Glu Val Trp Phe Gly Phe His Gln Ser Val Arg Pro
            195                 200                 205

Ser Leu Trp Lys Met Met Leu Asn Ile Asp Val Ser Ala Thr Ala Phe
210                 215                 220

Tyr Lys Ala Gln Pro Val Ile Glu Phe Val Cys Glu Val Leu Asp Phe
225                 230                 235                 240

Lys Ser Ile Glu Glu Gln Lys Pro Leu Thr Asp Ser Gln Arg Val
                245                 250                 255

Lys Phe Thr Lys Glu Ile Lys Gly Leu Lys Val Glu Ile Thr His Cys
                260                 265                 270

Gly Gln Met Lys Arg Lys Tyr Arg Val Cys Asn Val Thr Arg Arg Pro
            275                 280                 285

Ala Ser His Gln Thr Phe Pro Leu Gln Gln Glu Ser Gly Gln Thr Val
290                 295                 300

Glu Cys Thr Val Ala Gln Tyr Phe Lys Asp Arg His Lys Leu Val Leu
305                 310                 315                 320

Arg Tyr Pro His Leu Pro Cys Leu Gln Val Gly Gln Glu Gln Lys His
                325                 330                 335

Thr Tyr Leu Pro Leu Glu Val Cys Asn Ile Val Ala Gly Gln Arg Cys
                340                 345                 350

Ile Lys Lys Leu Thr Asp Asn Gln Thr Ser Thr Met Ile Arg Ala Thr
            355                 360                 365

Ala Arg Ser Ala Pro Asp Arg Gln Glu Glu Ile Ser Lys Leu Met Arg
370                 375                 380

Ser Ala Ser Phe Asn Thr Asp Pro Tyr Val Arg Glu Phe Gly Ile Met
385                 390                 395                 400

Val Lys Asp Glu Met Thr Asp Val Thr Gly Arg Val Leu Gln Pro Pro
                405                 410                 415

Ser Ile Leu Tyr Gly Gly Arg Asn Lys Ala Ile Ala Thr Pro Val Gln
            420                 425                 430

Gly Val Trp Asp Met Arg Asn Lys Gln Phe His Thr Gly Ile Glu Ile
            435                 440                 445

Lys Val Trp Ala Ile Ala Cys Phe Ala Pro Gln Arg Gln Cys Thr Glu
450                 455                 460

Val His Leu Lys Ser Phe Thr Glu Gln Leu Arg Lys Ile Ser Arg Asp
465                 470                 475                 480

Ala Gly Met Pro Ile Gln Gly Gln Pro Cys Phe Cys Lys Tyr Ala Gln
                485                 490                 495

Gly Ala Asp Ser Val Glu Pro Met Phe Arg His Leu Lys Asn Thr Tyr
            500                 505                 510

Ala Gly Leu Gln Leu Val Val Ile Leu Pro Gly Lys Thr Pro Val
            515                 520                 525

Tyr Ala Glu Val Lys Arg Val Gly Asp Thr Val Leu Gly Met Ala Thr
530                 535                 540

Gln Cys Val Gln Met Lys Asn Val Gln Arg Thr Thr Pro Gln Thr Leu
```

```
                545                 550                 555                 560
Ser Asn Leu Cys Leu Lys Ile Asn Val Lys Leu Gly Gly Val Asn Asn
                    565                 570                 575

Ile Leu Leu Pro Gln Gly Arg Pro Pro Val Phe Gln Gln Pro Val Ile
            580                 585                 590

Phe Leu Gly Ala Asp Val Thr His Pro Pro Ala Gly Asp Gly Lys Lys
        595                 600                 605

Pro Ser Ile Ala Ala Val Val Gly Ser Met Asp Ala His Pro Asn Arg
    610                 615                 620

Tyr Cys Ala Thr Val Arg Val Gln Gln His Arg Gln Glu Ile Ile Gln
625                 630                 635                 640

Asp Leu Ala Ala Met Val Arg Glu Leu Leu Ile Gln Phe Tyr Lys Ser
                    645                 650                 655

Thr Arg Phe Lys Pro Thr Arg Ile Ile Phe Tyr Arg Asp Gly Val Ser
                660                 665                 670

Glu Gly Gln Phe Gln Gln Val Leu His His Glu Leu Leu Ala Ile Arg
            675                 680                 685

Glu Ala Cys Ile Lys Leu Glu Lys Asp Tyr Gln Pro Gly Ile Thr Phe
        690                 695                 700

Ile Val Val Gln Lys Arg His His Thr Arg Leu Phe Cys Thr Asp Lys
705                 710                 715                 720

Asn Glu Arg Val Gly Lys Ser Gly Asn Ile Pro Ala Gly Thr Thr Val
                    725                 730                 735

Asp Thr Lys Ile Thr His Pro Thr Glu Phe Asp Phe Tyr Leu Cys Ser
                740                 745                 750

His Ala Gly Ile Gln Gly Thr Ser Arg Pro Ser His Tyr His Val Leu
            755                 760                 765

Trp Asp Asp Asn Arg Phe Ser Ser Asp Glu Leu Gln Ile Leu Thr Tyr
        770                 775                 780

Gln Leu Cys His Thr Tyr Val Arg Cys Thr Arg Ser Val Ser Ile Pro
785                 790                 795                 800

Ala Pro Ala Tyr Tyr Ala His Leu Val Ala Phe Arg Ala Arg Tyr His
                    805                 810                 815

Leu Val Asp Lys Glu His Asp Ser Ala Glu Gly Ser His Thr Ser Gly
                820                 825                 830

Gln Ser Asn Gly Arg Asp His Gln Ala Leu Ala Lys Ala Val Gln Val
            835                 840                 845

His Gln Asp Thr Leu Arg Thr Met Tyr Phe Ala
        850                 855

<210> SEQ ID NO 3
<211> LENGTH: 825
<212> TYPE: PRT
<213> ORGANISM: Homo sapiens

<400> SEQUENCE: 3

Met Tyr Ser Gly Ala Gly Pro Ala Leu Ala Pro Ala Pro Pro Pro Pro
1               5                   10                  15

Pro Ile Gln Gly Tyr Ala Phe Lys Pro Pro Pro Arg Pro Asp Phe Gly
            20                  25                  30

Thr Ser Gly Arg Thr Ile Lys Leu Gln Ala Asn Phe Phe Glu Met Asp
        35                  40                  45

Ile Pro Lys Ile Asp Ile Tyr His Tyr Glu Leu Asp Ile Lys Pro Glu
    50                  55                  60
```

-continued

```
Lys Cys Pro Arg Arg Val Asn Arg Glu Ile Val Glu His Met Val Gln
 65                  70                  75                  80

His Phe Lys Thr Gln Ile Phe Gly Asp Arg Lys Pro Val Phe Asp Gly
                 85                  90                  95

Arg Lys Asn Leu Tyr Thr Ala Met Pro Leu Pro Ile Gly Arg Asp Lys
            100                 105                 110

Val Glu Leu Glu Val Thr Leu Pro Gly Glu Gly Lys Asp Arg Ile Phe
        115                 120                 125

Lys Val Ser Ile Lys Trp Val Ser Cys Val Ser Leu Gln Ala Leu His
130                 135                 140

Asp Ala Leu Ser Gly Arg Leu Pro Ser Val Pro Phe Glu Thr Ile Gln
145                 150                 155                 160

Ala Leu Asp Val Val Met Arg His Leu Pro Ser Met Arg Tyr Thr Pro
                165                 170                 175

Val Gly Arg Ser Phe Phe Thr Ala Ser Glu Gly Cys Ser Asn Pro Leu
            180                 185                 190

Gly Gly Gly Arg Glu Val Trp Phe Gly Phe His Gln Ser Val Arg Pro
        195                 200                 205

Ser Leu Trp Lys Met Met Leu Asn Ile Asp Val Ser Ala Thr Ala Phe
210                 215                 220

Tyr Lys Ala Gln Pro Val Ile Glu Phe Val Cys Glu Val Leu Asp Phe
225                 230                 235                 240

Lys Ser Ile Glu Glu Gln Lys Pro Leu Thr Asp Ser Gln Arg Val
                245                 250                 255

Lys Phe Thr Lys Glu Ile Lys Gly Leu Lys Val Glu Ile Thr His Cys
            260                 265                 270

Gly Gln Met Lys Arg Lys Tyr Arg Val Cys Asn Val Thr Arg Arg Pro
        275                 280                 285

Ala Ser His Gln Thr Phe Pro Leu Gln Gln Glu Ser Gly Gln Thr Val
290                 295                 300

Glu Cys Thr Val Ala Gln Tyr Phe Lys Asp Arg His Lys Leu Val Leu
305                 310                 315                 320

Arg Tyr Pro His Leu Pro Cys Leu Gln Val Gly Gln Glu Gln Lys His
                325                 330                 335

Thr Tyr Leu Pro Leu Glu Val Cys Asn Ile Val Ala Gly Gln Arg Cys
            340                 345                 350

Ile Lys Lys Leu Thr Asp Asn Gln Thr Ser Thr Met Ile Arg Ala Thr
        355                 360                 365

Ala Arg Ser Ala Pro Asp Arg Gln Glu Glu Ile Ser Lys Leu Met Arg
370                 375                 380

Ser Ala Ser Phe Asn Thr Asp Pro Tyr Val Arg Glu Phe Gly Ile Met
385                 390                 395                 400

Val Lys Asp Glu Met Thr Asp Val Thr Gly Arg Val Leu Gln Pro Pro
                405                 410                 415

Ser Ile Leu Tyr Gly Gly Arg Asn Lys Ala Ile Ala Thr Pro Val Gln
            420                 425                 430

Gly Val Trp Asp Met Arg Asn Lys Gln Phe His Thr Gly Ile Glu Ile
        435                 440                 445

Lys Val Trp Ala Ile Ala Cys Phe Ala Pro Gln Arg Gln Cys Thr Glu
450                 455                 460

Val His Leu Lys Ser Phe Thr Glu Gln Leu Arg Lys Ile Ser Arg Asp
465                 470                 475                 480

Ala Gly Met Pro Ile Gln Gly Gln Pro Cys Phe Cys Lys Tyr Ala Gln
```

485                 490                 495
Gly Ala Asp Ser Val Glu Pro Met Phe Arg His Leu Lys Asn Thr Tyr
            500                 505                 510

Ala Gly Leu Gln Leu Val Val Ile Leu Pro Gly Lys Thr Pro Val
        515                 520                 525

Tyr Ala Glu Val Lys Arg Val Gly Asp Thr Val Leu Gly Met Ala Thr
    530                 535                 540

Gln Cys Val Gln Met Lys Asn Val Gln Arg Thr Thr Pro Gln Thr Leu
545                 550                 555                 560

Ser Asn Leu Cys Leu Lys Ile Asn Val Lys Leu Gly Gly Val Asn Asn
                565                 570                 575

Ile Leu Leu Pro Gln Gly Arg Pro Pro Val Phe Gln Gln Pro Val Ile
            580                 585                 590

Phe Leu Gly Ala Asp Val Thr His Pro Pro Ala Gly Asp Gly Lys Lys
        595                 600                 605

Pro Ser Ile Ala Ala Val Gly Ser Met Asp Ala His Pro Asn Arg
    610                 615                 620

Tyr Cys Ala Thr Val Arg Val Gln Gln His Arg Gln Glu Ile Ile Gln
625                 630                 635                 640

Asp Leu Ala Ala Met Val Arg Glu Leu Leu Ile Gln Phe Tyr Lys Ser
                645                 650                 655

Thr Arg Phe Lys Pro Thr Arg Ile Ile Phe Tyr Arg Asp Gly Val Ser
            660                 665                 670

Glu Gly Gln Phe Gln Gln Val Leu His His Glu Leu Leu Ala Ile Arg
        675                 680                 685

Glu Ala Cys Ile Lys Leu Glu Lys Asp Tyr Gln Pro Gly Ile Thr Phe
    690                 695                 700

Ile Val Val Gln Lys Arg His His Thr Arg Leu Phe Cys Thr Asp Lys
705                 710                 715                 720

Asn Glu Arg Gly Thr Ser Arg Pro Ser His Tyr His Val Leu Trp Asp
                725                 730                 735

Asp Asn Arg Phe Ser Ser Asp Glu Leu Gln Ile Leu Thr Tyr Gln Leu
            740                 745                 750

Cys His Thr Tyr Val Arg Cys Thr Arg Ser Val Ser Ile Pro Ala Pro
        755                 760                 765

Ala Tyr Tyr Ala His Leu Val Ala Phe Arg Ala Arg Tyr His Leu Val
    770                 775                 780

Asp Lys Glu His Asp Ser Ala Glu Gly Ser His Thr Ser Gly Gln Ser
785                 790                 795                 800

Asn Gly Arg Asp His Gln Ala Leu Ala Lys Ala Val Gln Val His Gln
                805                 810                 815

Asp Thr Leu Arg Thr Met Tyr Phe Ala
            820                 825

<210> SEQ ID NO 4
<211> LENGTH: 22
<212> TYPE: RNA
<213> ORGANISM: Artificial Sequence
<220> FEATURE:
<223> OTHER INFORMATION: synthetic miRNA

<400> SEQUENCE: 4
acaaccagcu aagacacugc ca                                        22

<210> SEQ ID NO 5

```
<211> LENGTH: 19
<212> TYPE: RNA
<213> ORGANISM: Artificial Sequence
<220> FEATURE:
<223> OTHER INFORMATION: sythetic siRNA

<400> SEQUENCE: 5
gcaccaucuu cuucaagga                                                    19

<210> SEQ ID NO 6
<211> LENGTH: 19
<212> TYPE: RNA
<213> ORGANISM: Artificial Sequence
<220> FEATURE:
<223> OTHER INFORMATION: synthetic siRNA

<400> SEQUENCE: 6
uccuugaaga agauggugc                                                    19

<210> SEQ ID NO 7
<211> LENGTH: 22
<212> TYPE: RNA
<213> ORGANISM: Artificial Sequence
<220> FEATURE:
<223> OTHER INFORMATION: synthetic miRNA

<400> SEQUENCE: 7
acaaccagcu aagacacugc ca                                                22

<210> SEQ ID NO 8
<211> LENGTH: 22
<212> TYPE: RNA
<213> ORGANISM: Artificial Sequence
<220> FEATURE:
<223> OTHER INFORMATION: synthetic miRNA

<400> SEQUENCE: 8
uggcagmguc uuagcugguu gu                                                22

<210> SEQ ID NO 9
<211> LENGTH: 19
<212> TYPE: RNA
<213> ORGANISM: Artificial Sequence
<220> FEATURE:
<223> OTHER INFORMATION: synthetic siRNA

<400> SEQUENCE: 9
ggacgaggac gagcacuuc                                                    19

<210> SEQ ID NO 10
<211> LENGTH: 19
<212> TYPE: RNA
<213> ORGANISM: Artificial Sequence
<220> FEATURE:
<223> OTHER INFORMATION: synthetic siRNA

<400> SEQUENCE: 10
gaagugcucg uccucgucc                                                    19

<210> SEQ ID NO 11
<211> LENGTH: 25
<212> TYPE: RNA
<213> ORGANISM: Artificial Sequence
<220> FEATURE:
<223> OTHER INFORMATION: synthetic siRNA

<400> SEQUENCE: 11
```

-continued

```
caggguguca gaucacaugg gcuaa                                              25

<210> SEQ ID NO 12
<211> LENGTH: 25
<212> TYPE: RNA
<213> ORGANISM: Artificial Sequence
<220> FEATURE:
<223> OTHER INFORMATION: synthetic siRNA

<400> SEQUENCE: 12
uuagcccaug ugaucugaca cccug                                              25

<210> SEQ ID NO 13
<211> LENGTH: 20
<212> TYPE: DNA
<213> ORGANISM: Artificial Sequence
<220> FEATURE:
<223> OTHER INFORMATION: synthetic primer

<400> SEQUENCE: 13
tccctggaga agagctacga                                                    20

<210> SEQ ID NO 14
<211> LENGTH: 20
<212> TYPE: DNA
<213> ORGANISM: Artificial Sequence
<220> FEATURE:
<223> OTHER INFORMATION: synthetic primer

<400> SEQUENCE: 14
agcactgtgt tggcgtacag                                                    20

<210> SEQ ID NO 15
<211> LENGTH: 20
<212> TYPE: DNA
<213> ORGANISM: Artificial Sequence
<220> FEATURE:
<223> OTHER INFORMATION: synthetic primer

<400> SEQUENCE: 15
tggcgctttt gactcaggat                                                    20

<210> SEQ ID NO 16
<211> LENGTH: 20
<212> TYPE: DNA
<213> ORGANISM: Artificial Sequence
<220> FEATURE:
<223> OTHER INFORMATION: synthetic primer

<400> SEQUENCE: 16
gggatgtttg ctccaaccaa                                                    20

<210> SEQ ID NO 17
<211> LENGTH: 20
<212> TYPE: DNA
<213> ORGANISM: Artificial Sequence
<220> FEATURE:
<223> OTHER INFORMATION: synthetic primer

<400> SEQUENCE: 17
ggatcgctga ggtacaaccc                                                    20

<210> SEQ ID NO 18
<211> LENGTH: 20
<212> TYPE: DNA
```

<213> ORGANISM: Artificial Sequence
<220> FEATURE:
<223> OTHER INFORMATION: synthetic primer

<400> SEQUENCE: 18
gtcaggggtc tcgactgtct                                           20

<210> SEQ ID NO 19
<211> LENGTH: 24
<212> TYPE: DNA
<213> ORGANISM: Artificial Sequence
<220> FEATURE:
<223> OTHER INFORMATION: synthetic primer

<400> SEQUENCE: 19
tgcagcgcgt tgacttattc atgg                                      24

<210> SEQ ID NO 20
<211> LENGTH: 24
<212> TYPE: DNA
<213> ORGANISM: Artificial Sequence
<220> FEATURE:
<223> OTHER INFORMATION: synthetic primer

<400> SEQUENCE: 20
gaaaccacaa cctgcatgaa gcga                                      24

<210> SEQ ID NO 21
<211> LENGTH: 21
<212> TYPE: DNA
<213> ORGANISM: Artificial Sequence
<220> FEATURE:
<223> OTHER INFORMATION: synthetic primer

<400> SEQUENCE: 21
cagatggcac ttacacccgt g                                         21

<210> SEQ ID NO 22
<211> LENGTH: 21
<212> TYPE: DNA
<213> ORGANISM: Artificial Sequence
<220> FEATURE:
<223> OTHER INFORMATION: synthetic primer

<400> SEQUENCE: 22
gcagcccaat caggtcaaag a                                         21

<210> SEQ ID NO 23
<211> LENGTH: 22
<212> TYPE: DNA
<213> ORGANISM: Artificial Sequence
<220> FEATURE:
<223> OTHER INFORMATION: synthetic primer

<400> SEQUENCE: 23
ttctaccgcg ccggtgtctc tg                                        22

<210> SEQ ID NO 24
<211> LENGTH: 18
<212> TYPE: DNA

```
<213> ORGANISM: Artificial Sequence
<220> FEATURE:
<223> OTHER INFORMATION: synthetic primer

<400> SEQUENCE: 24
gatgatgcgg gtgggctt                                                18
```

ARGONAUTE PROTEIN-DOUBLE STRANDED RNA COMPLEXES AND USES RELATED THERETO

CROSS-REFERENCE TO RELATED APPLICATION

This application claims the benefit of U.S. Provisional Application No. 62/505,430, filed on May 12, 2017; the entire contents of said application is incorporated herein in its entirety by this reference.

GOVERNMENT SUPPORT

This invention was made with Government support under Grant No. W81XWH-14-1-0544 awarded by the U.S. Army Medical Research and Material Command. The Government has certain rights in the invention.

BACKGROUND OF THE INVENTION

The discovery of RNA interference (RNAi) has emerged as a potent tool for antisense oligonucleotide (ASO) therapeutics for gene silencing. Transfection of short double-stranded RNAs—namely, small interference RNAs (siRNAs), which are 21-23 nucleotides in length and contain an mRNA sequence (passenger strand) and its complement (guide strand)—harnesses this ubiquitous pathway to degrade target gene mRNA and suppress its expression with high specificity. In particular, siRNAs have been extensively explored as gene silencing drugs, but their instability, low valence, and high stiffness have made efficient delivery difficult. In the past decades, numerous siRNA carriers and chemical methods have been reported to improve the efficacy of siRNA-mediated gene silencing in vitro and in vivo. Yet the efficient gene silencing remains challenging. The rate-limiting factor is the Argonaute 2 (Ago2) protein, which carries the single stranded antisense siRNA (guide RNA) to recognize targeted mRNA substrate and leads to mRNA degradation inside cells.

Thus, to fully exploit siRNA's gene silencing capabilities insides cells for higher therapeutic potency, novel therapeutic methods are needed to improve silencing efficiency.

SUMMARY OF THE INVENTION

Provided herein are RNA protein complexes (RNPs) with enhanced gene silencing effects over conventional siRNA technologies. Such RNPs comprise (a) a short double-stranded RNA (dsRNA), or analog thereof; and (b) an Argonaute 2 protein (Ago2), or biologically active fragment or homolog thereof, wherein said Ago2 comprises a polypeptide having at least 85% sequence identity to the amino acid sequence set forth in SEQ ID NO: 1, 2, or 3. Pharmaceutical compositions of said RNP and a pharmaceutically acceptable carrier are also provided herein.

Another aspect of the invention relates to a method for silencing the expression of a target gene in a cell. The method comprises (i) providing a short double-stranded RNA (dsRNA), or analog thereof; (ii) complexing the dsRNA to an Argonaute 2 protein (Ago2), or biologically active fragment or homolog thereof; wherein said Ago2 comprises a polypeptide having at least 85% sequence identity to the amino acid sequence set forth in SEQ ID NO: 1, 2, or 3 (iii) forming an Ago2 protein-dsRNA complex (RNP) comprising the dsRNA and the Ago2; and (iv) introducing the RNP into the cell; thereby inducing gene silencing of the target gene.

Another aspect of the invention relates to a method of treating a disorder treatable by gene silencing (e.g., cancer, viral or bacterial infection, neurological disorders, metabolic disorders) comprising administering to a subject in need thereof a therapeutically effective amount of the RNP of the present invention Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE DRAWINGS

The patent or application file contains at least one drawing executed in color. Copies of this patent or patent application publication with color drawing(s) will be provided by the Office upon request and payment of the necessary fee.

Figure 1B:
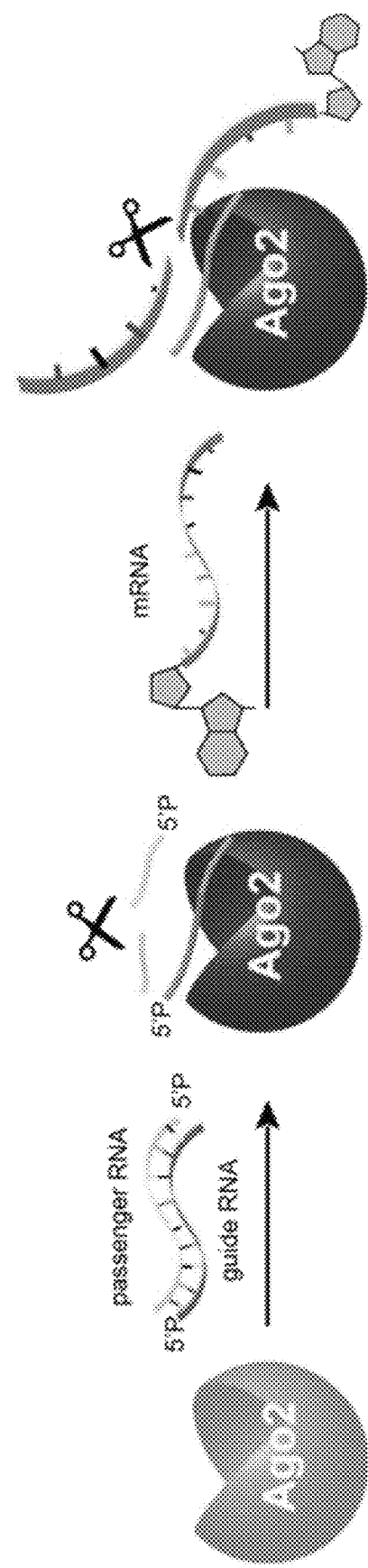
Figure 1C:
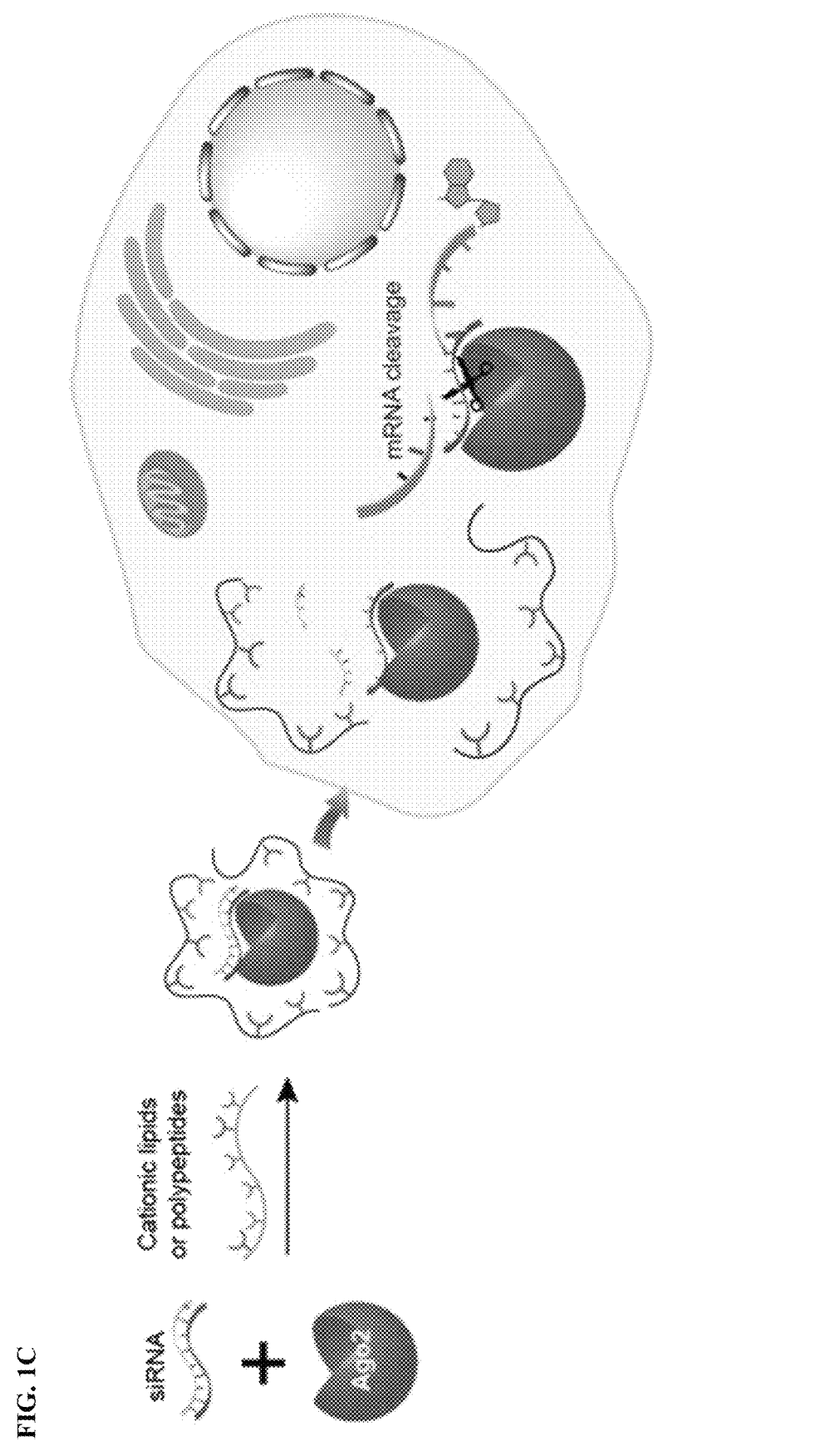

FIGS. 1A-1C collectively show a schematic diagram showing single-stranded (ss) siRNA versus double-stranded (ds) siRNA-loaded Ago2 protein for gene silencing. In FIG. 1A, ss siRNA-loaded Ago2 protein bears minimal activity in the target mRNA cleavage inside cells while the loading of Ago2 with ds siRNA primes Ago2-following the release of passenger RNA, Ago2 becomes activated and induces potent gene silencing (FIG. 1B). FIG. 1C is a cartoon schematic showing the codelivery of siRNA/Ago2 complex into cells. The complex is encapsulated by cationic lipids or synthetic polyamines. Following intracellular delivery, the passenger strand of duplex siRNA gets cleaved and dissociates from Ago2 during the assembly of RISC (Matranga C et al. (2005) *Cell* 123: 607-620; Leuschner P J et al. (2006) *EMBO Rep* 7:314-320), leaving the antisense strand-loaded Ago2 available for recognition and cleavage of target mRNA over a sustained period of time.

FIG. 2A-2D show plots depicting relative expression of GFP in percentage (%) at 24, 48, and 72 hours post-transfection with siGFP/Ago2 of either HEK293T or NIH3T3 cells.

Figure 3A:
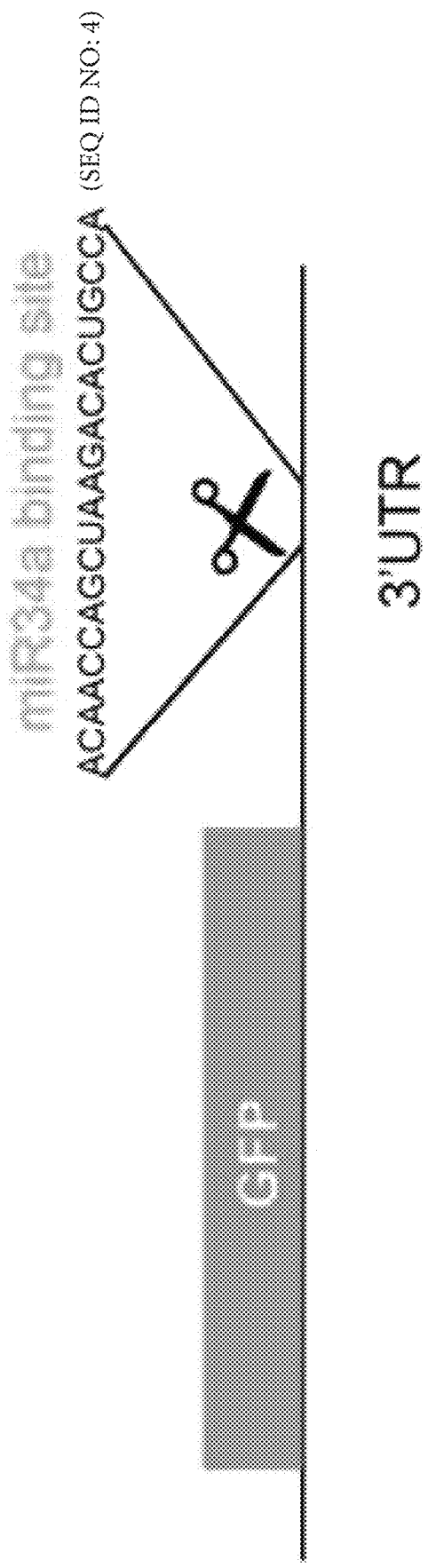
Figure 3B:
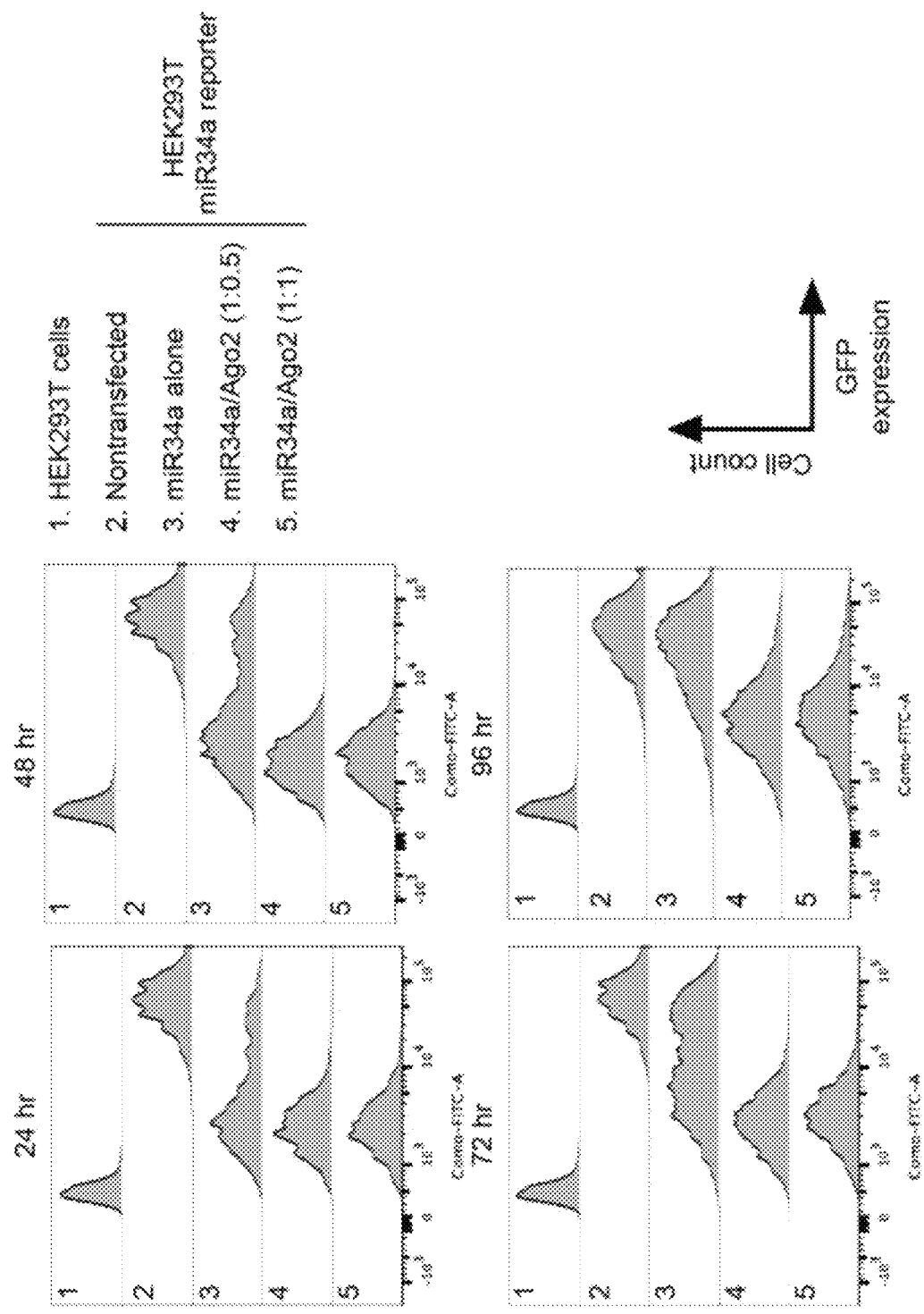
Figure 3C:
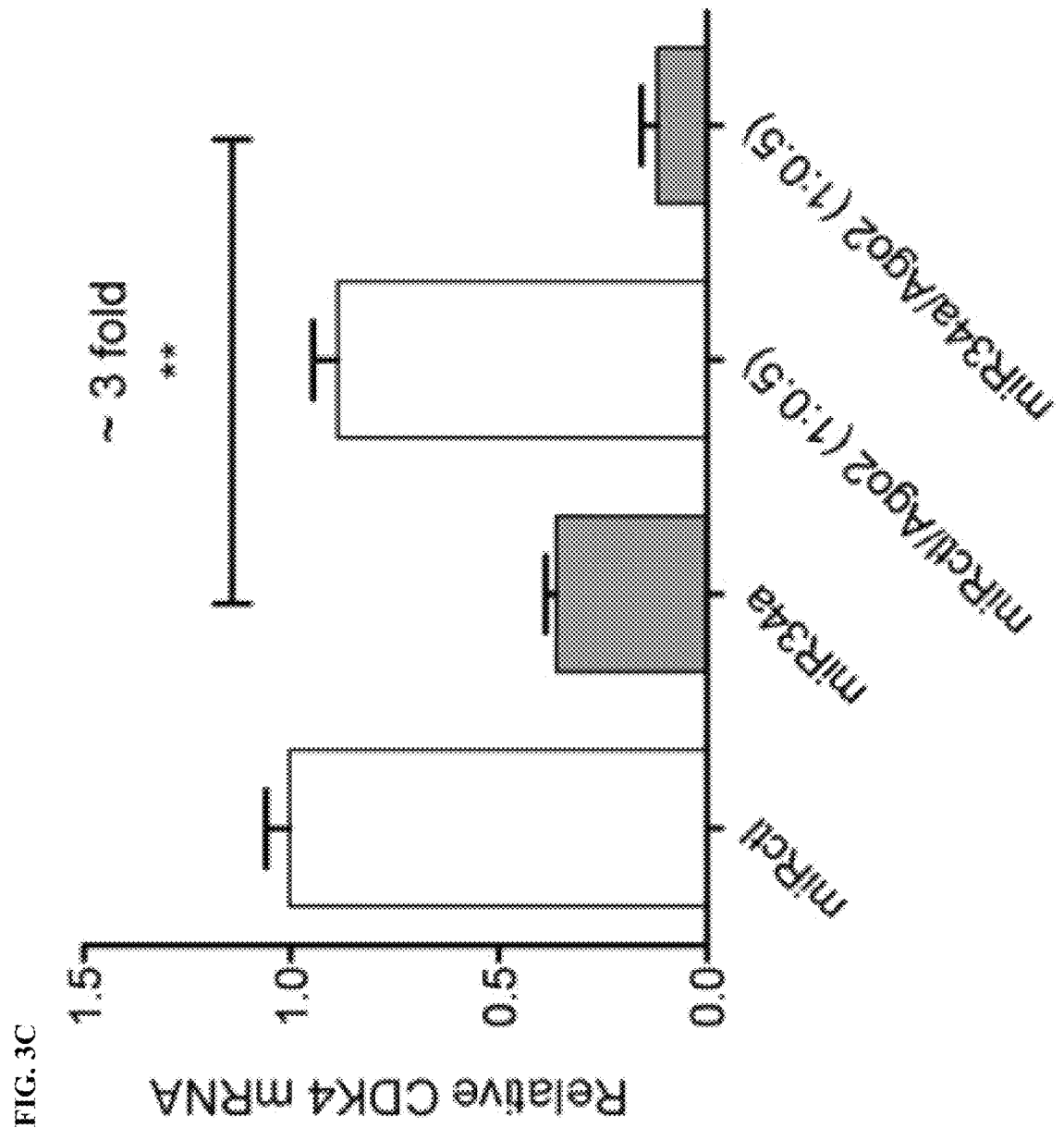

FIG. 3A is a cartoon depiction showing a GFP engineered with a micro34a binding site at the 3' untranslated region (3' UTR), wherein the micro34a binding site has the sequence ACAACCAGCUAAGACACUGCCA (SEQ ID NO: 4). FIG. 3B show four flow cytometry plots showing relative expression of GFP in cell count at 24, 48, 72 and 96 hours post-transfection with miR34a/Ago2 of HEK293T cells. FIG. 3C is a bar plot showing relative expression of CDK4 mRNA post-transfection with miR34a/Ago2 in OVCAR8 cells.

Figure 4A:
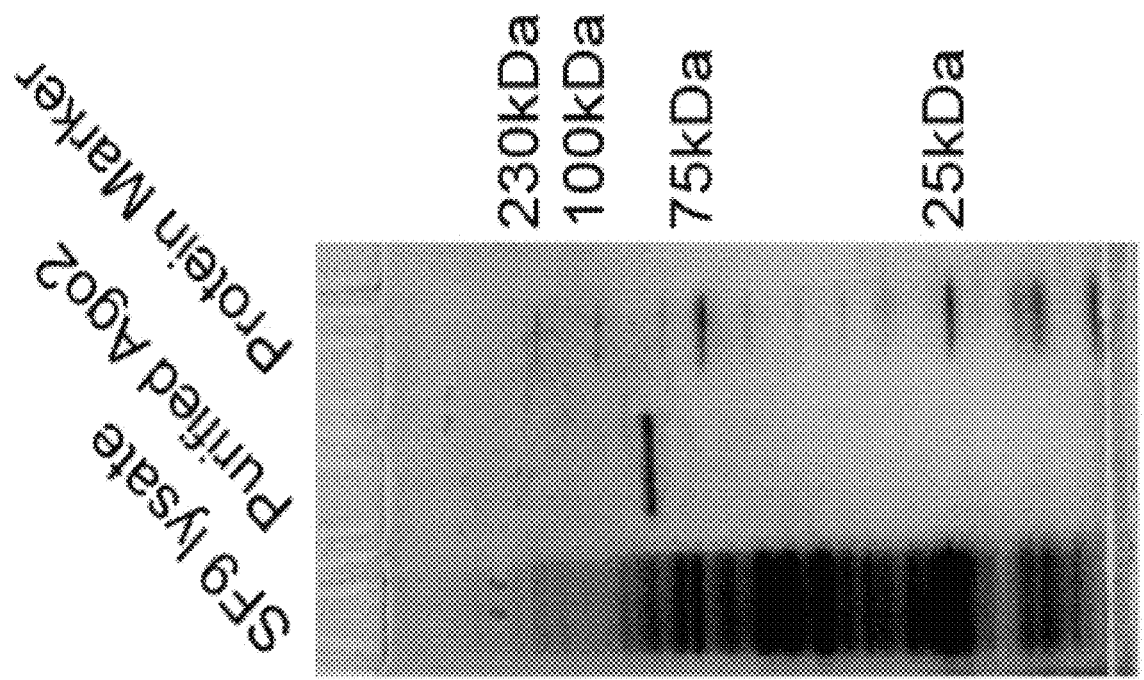
Figure 4B:
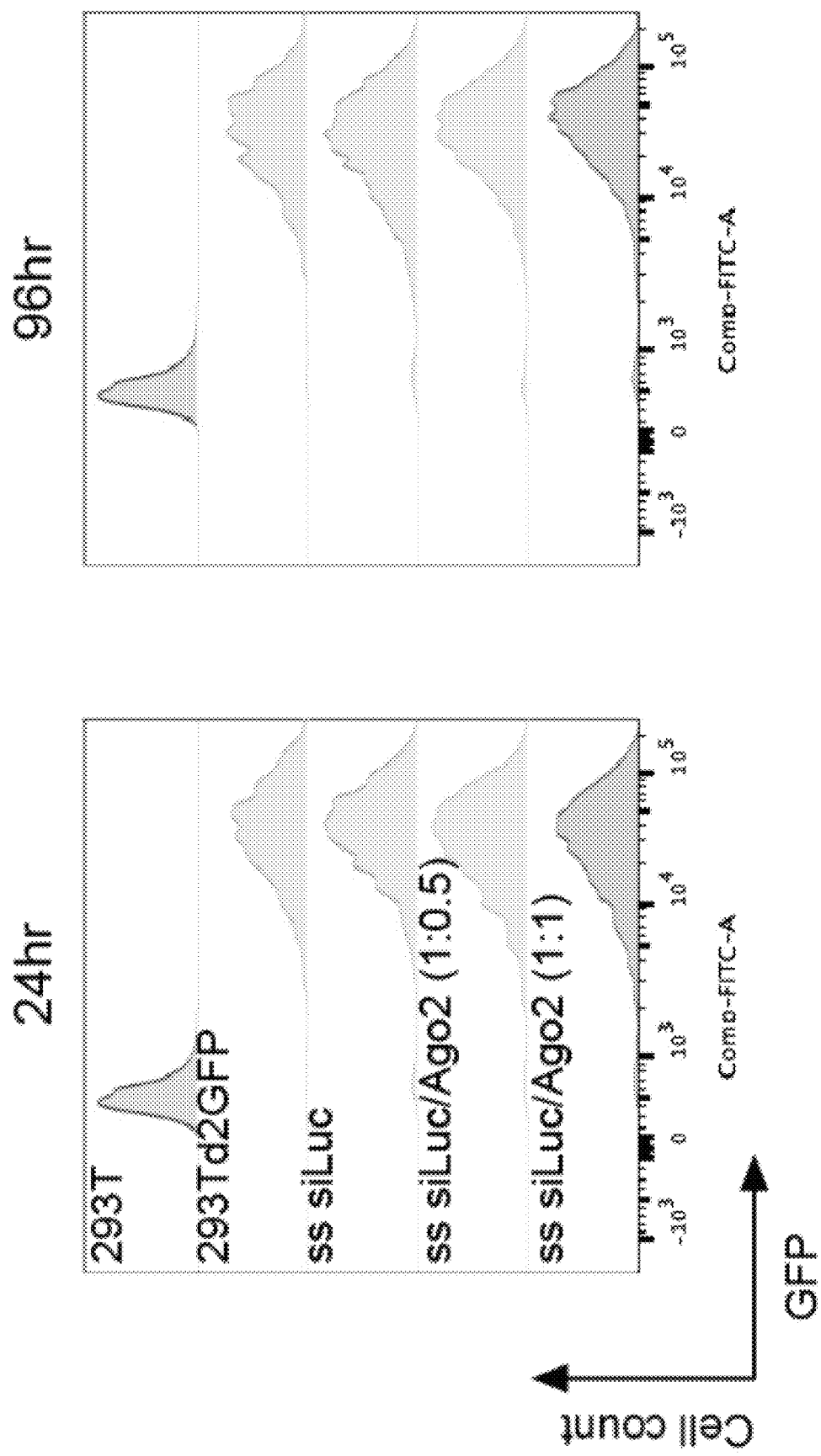
Figure 4C:
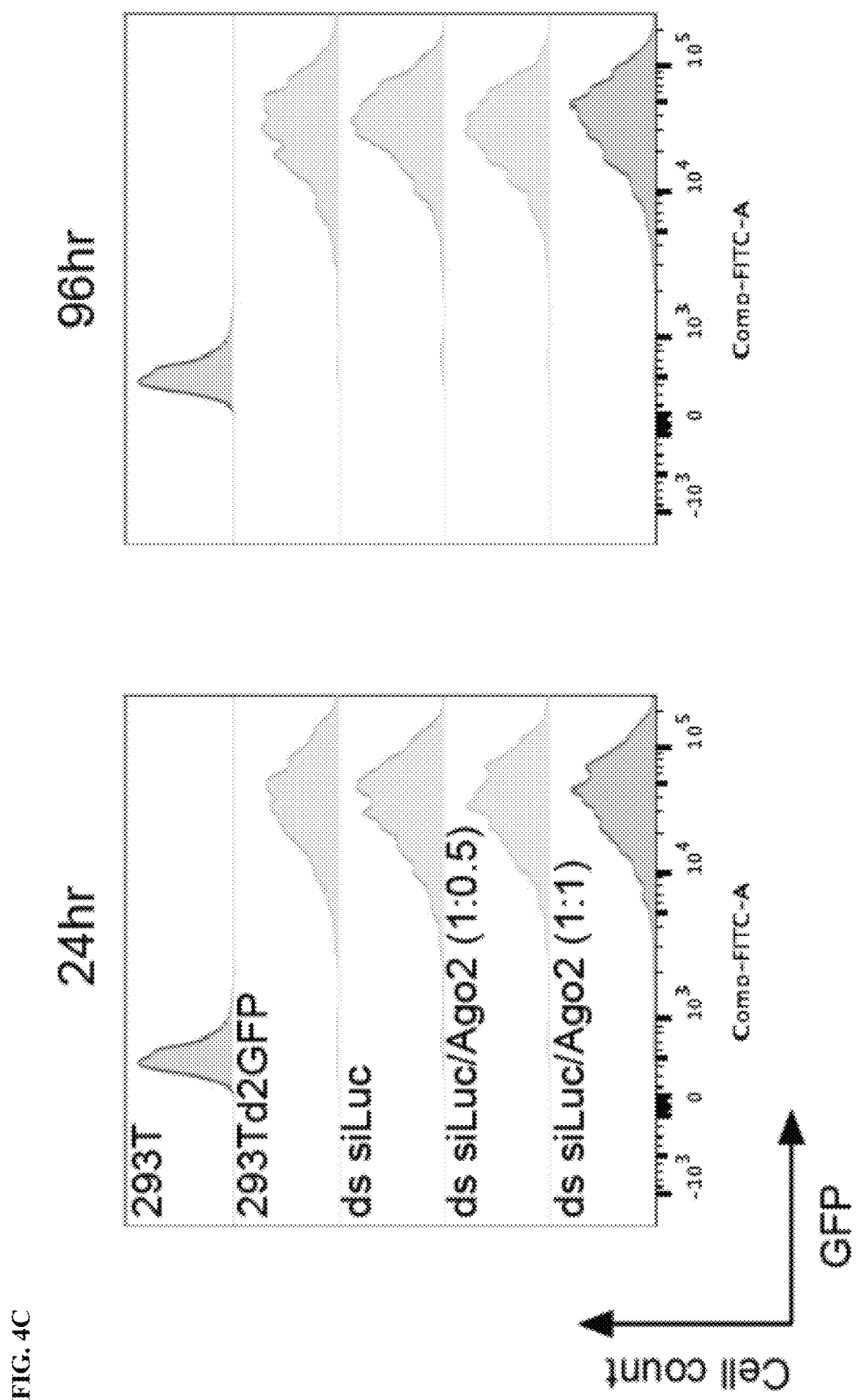

FIGS. 4A-4C collectively shows a photograph (FIG. 4A) and flow cytometry plots (FIG. 4B and FIG. 4c) depicting sequence-specific silencing of GFP via co-transfection of Ago2. FIG. 4A is a photograph of a SDS-PAGE of purified recombinant human Ago2 from SF9 insect cells. FIG. 4B and FIG. 4C are flow cytometry graphs showing the mean fluorescence intensity in 293Td2GFP cells resulting from transfection using TransIT-X2 of 25 nM single-stranded anti-luciferase siRNA (ss siLuc) (FIG. 4B), double-stranded anti-luciferase siRNA (ds siLuc) (FIG. 4C), or siLuc/Ago2 at two different molar ratios (1:0.5 and 1:1). The mean fluorescence intensity of GFP expression was quantified via flow cytometry.

Figure 5A:
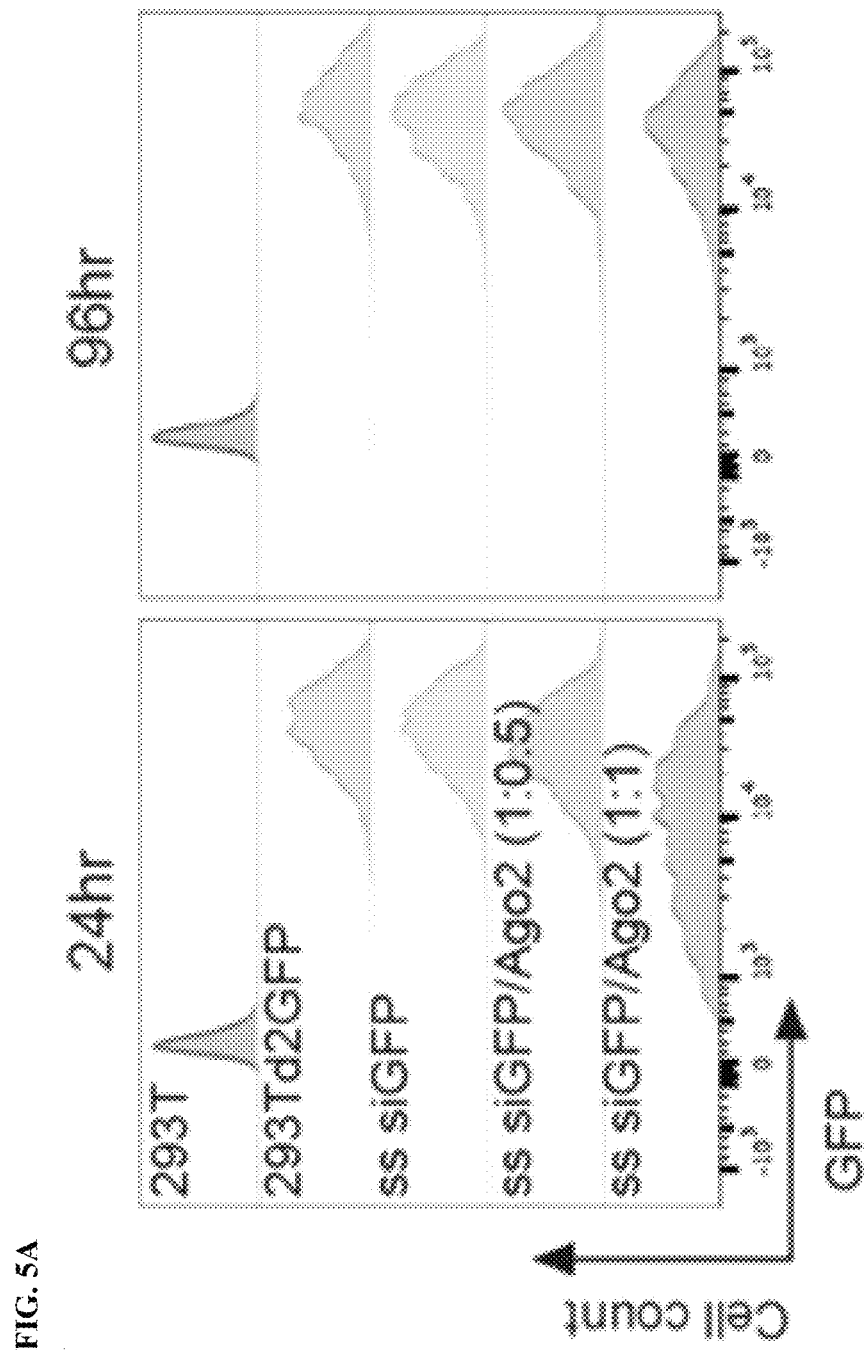
Figure 5B:
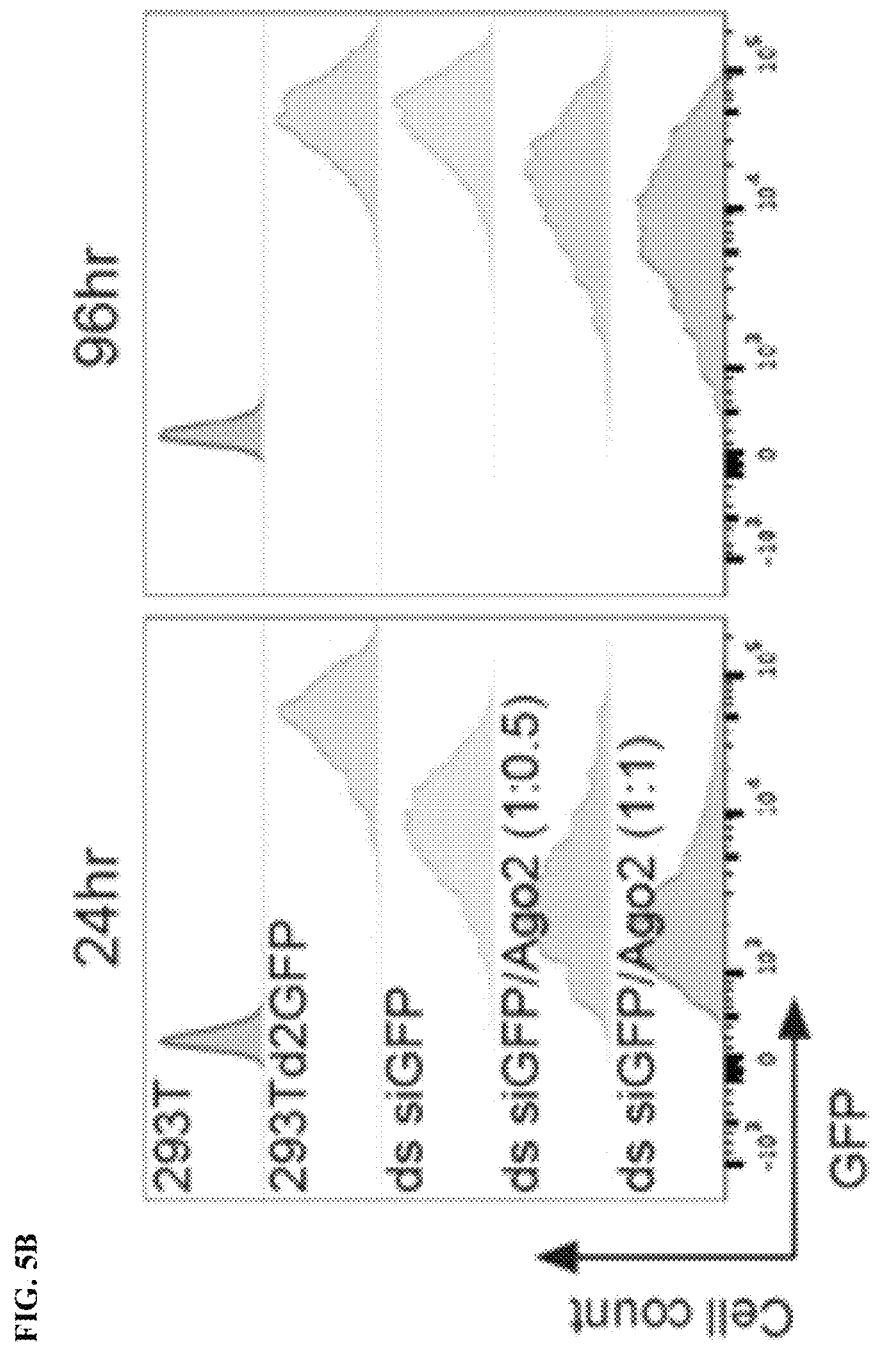
Figure 5C:
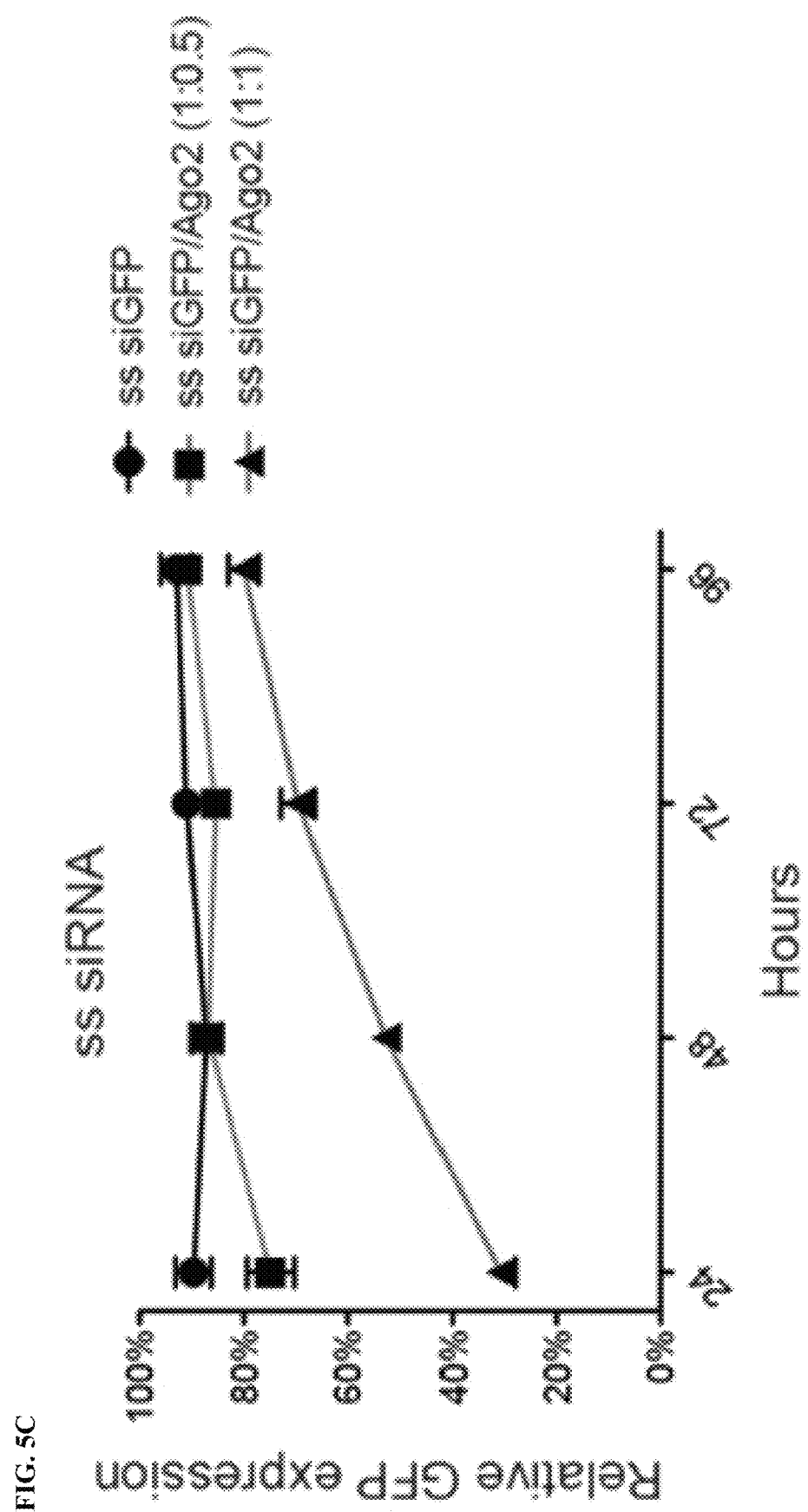
Figure 5D:
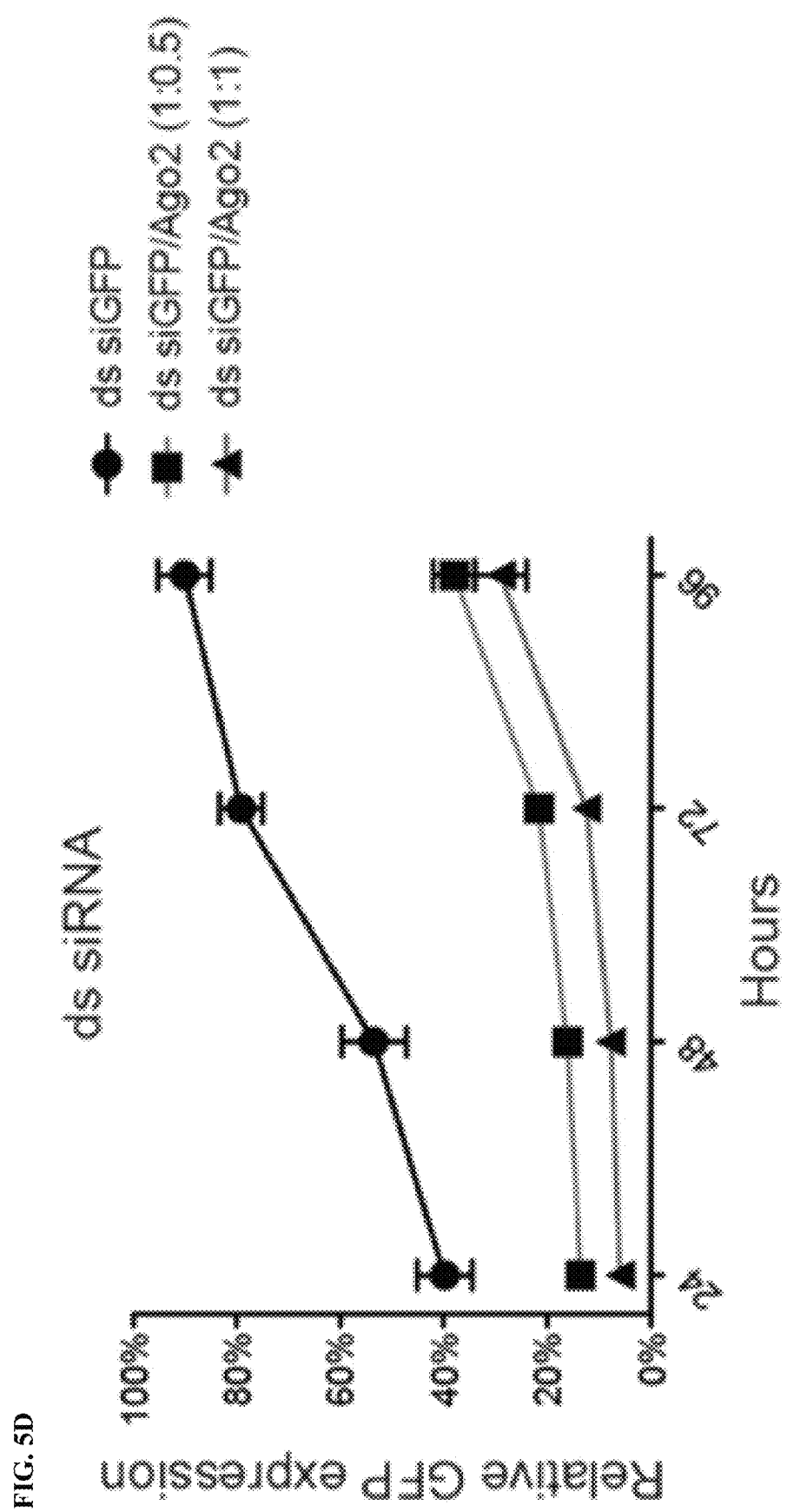
Figure 5E:
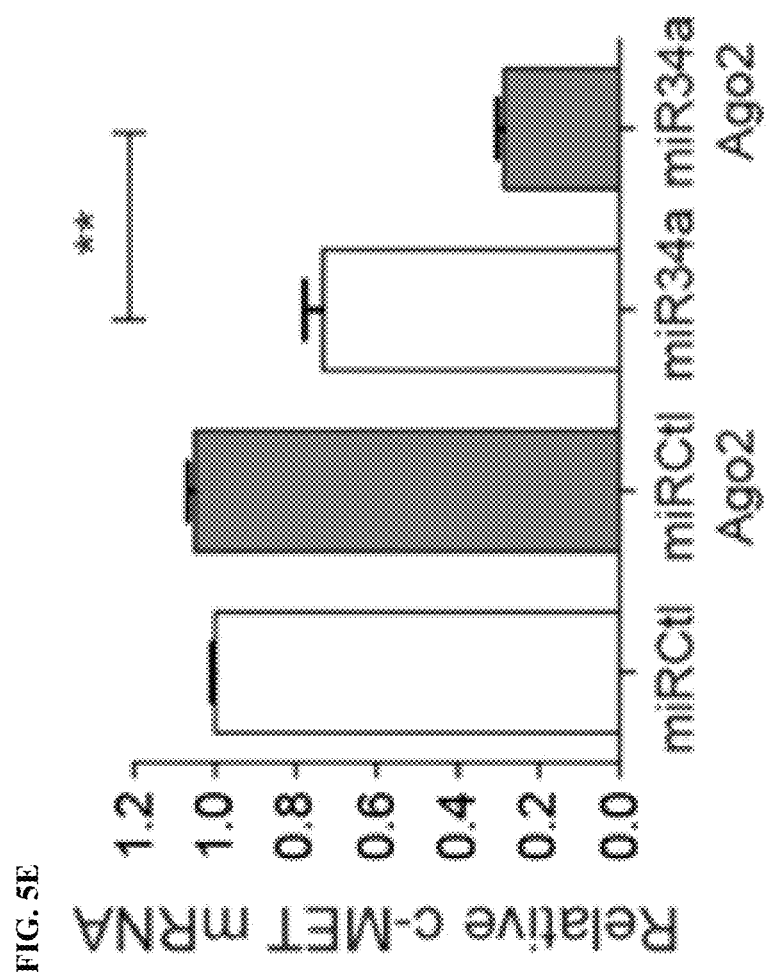
Figure 5F:
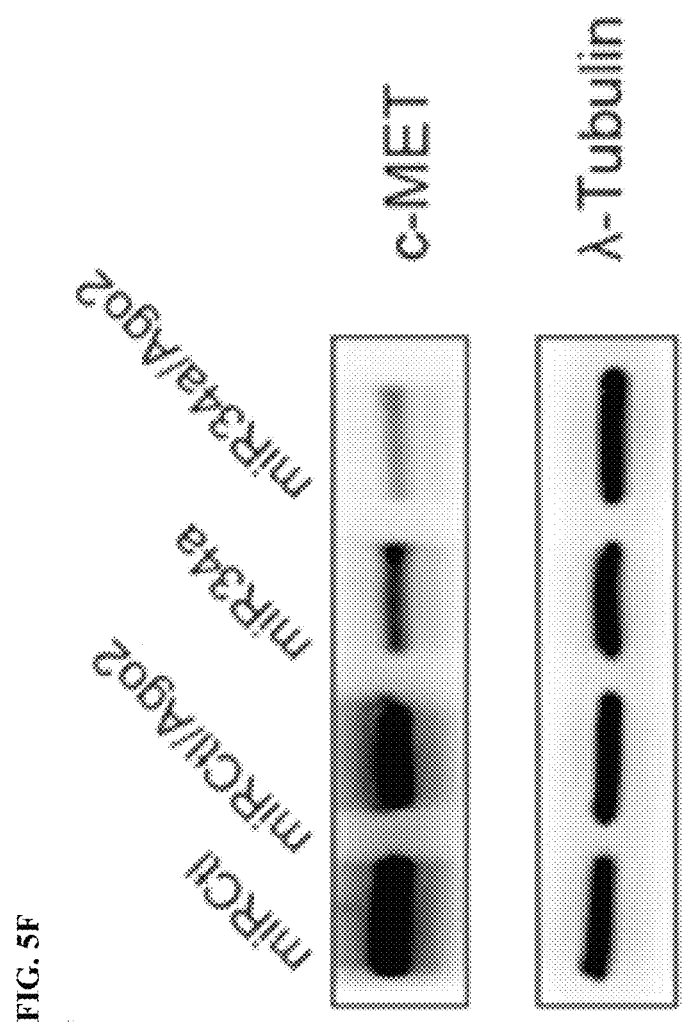

FIGS. 5A-5F collectively shows plots depicting that ds siRNA or miRNA mimics loaded with Ago2 elicit superior gene silencing. FIG. 5A and FIG. 45B are flow cytometry graphs showing mean fluorescence intensity of GFP expression resulting from experiments where ss siGFP (25 nM), ds siGFP (25 nM), or siGFP (25 nM)/Ago2 at two different molar ratios (1:0.5 and 1:1 RNA:Ago2) were transfected using TransIT-X2 into 293Td2GFP cells. FIG. 5A and FIG. 5B are representative histograms of GFP expression at 24- and 96-h posttransfection are shown for (FIG. 5A) ss siGFP and (FIG. 5B) ds siGFP. FIGS. 4C and 4D are plots showing quantification of GFP expression normalized to that of nontransfected 293Td2GFP over the course of 96 h after transfection of (FIG. 5C) ss siGFP or ss siGFP/Ago2; (FIG. 5D) ds siGFP or ds siGFP/Ago2. In addition to targeting GFP, 25 nM miR34a mimics were transfected along with Ago2 at a 1:1 molar ratio using TransIT-X2. A corresponding scrambled sequence (miRCtl) was used as a negative control. FIG. 5E is a bar graph showing the downregulation of a miR34a target, c-MET, confirmed by quantitative PCR via normalization to β-actin mRNA. FIG. 5F is a photograph depicting the downregulation of a miR34a target, c-MET, confirmed by Western blotting. Representative images of two independent experiments are shown. The λ-Tubulin served as an internal loading control. Data for GFP silencing and qPCR are represented as the mean±SEM (n=3); **P<0.01.

Figure 6A:
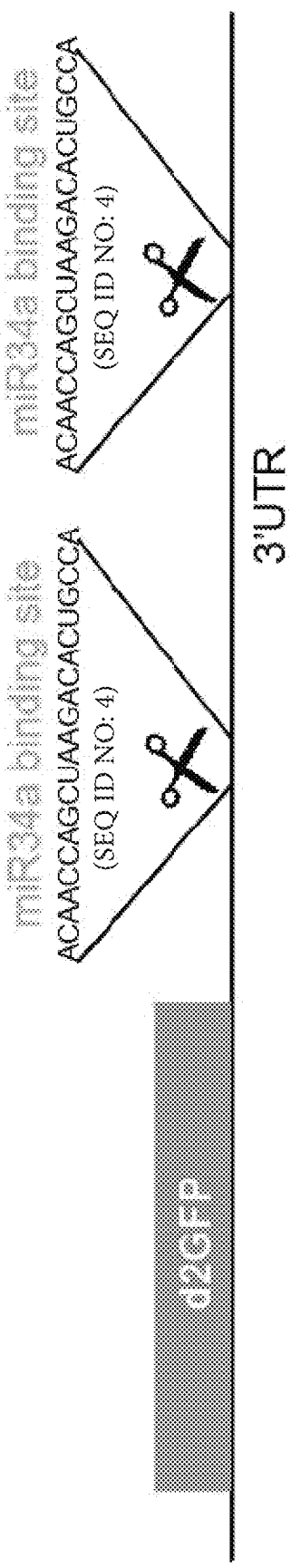
Figure 6B:
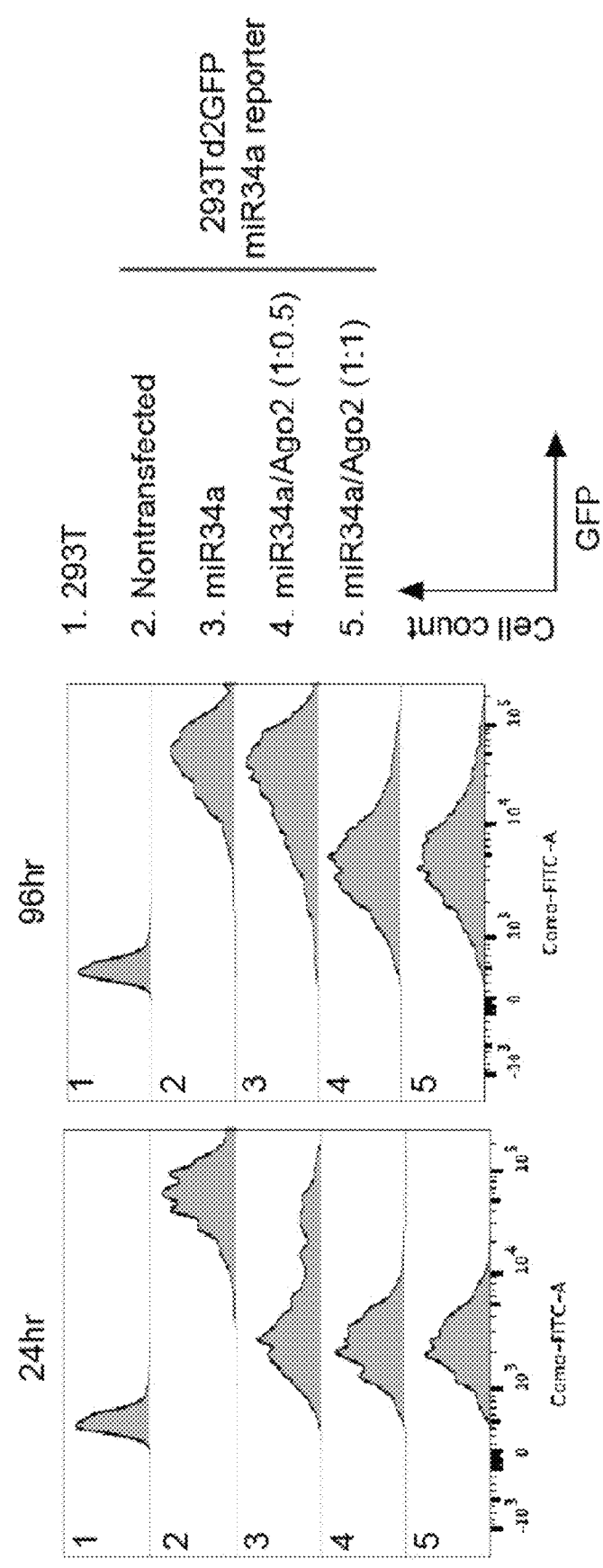

FIG. 6A is a cartoon schematic showing a miR34a reporter construct that includes two miR34a-binding sites in 3'UTR of GFP), wherein the two micro34a binding sites have the sequence ACAACCAGCUAAGACACUGCCA (SEQ ID NO: 4). FIGS. 6B-6D collectively depict graphs showing co-delivery of miR34a mimics and Ago2 in silencing miR34a reporter and its endogenous target. FIG. 6B is a flow cytometry graph showing mean fluorescence intensity of GFP expression resulting from experiments where 25 nM duplex miR34a mimics or miR34a/Ago2 at two different molar ratios (1:0.5 and 1:1) were transfected using TransIT-X2 into 293Td2GFP cells. GFP expression was measured by flow cytometry over 96 hours after transfection. FIG. 6C is a flow cytometry graph showing mean fluorescence intensity of GFP expression resulting from experiments where 25 nM duplex scramble control miRNA (miRCtl) or miRCtl/Ago2 at two different molar ratios (1:0.5 and 1:1) were transfected using TransIT-X2 into 293Td2GFP cells. FIG. 4D is a bar graph showing the quantitative PCR of a miR34a target, CDK4, at 48 hours after transfection of 25 nM miR34a mimics, miR34a mimics/Ago2, or the corresponding scrambled controls. CDK4 mRNA levels were normalized to actin mRNA levels.

Figure 7A:
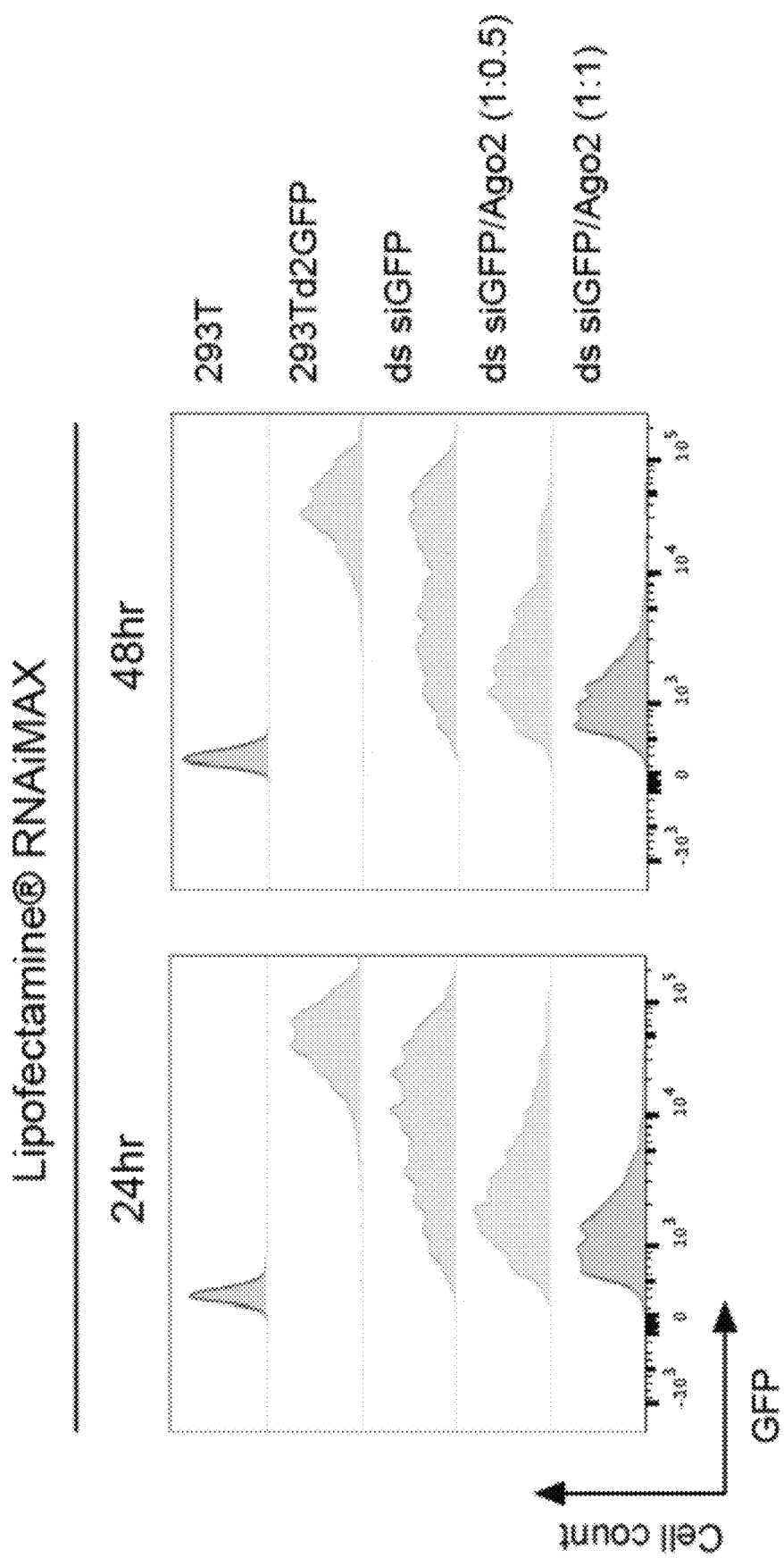
Figure 7B:
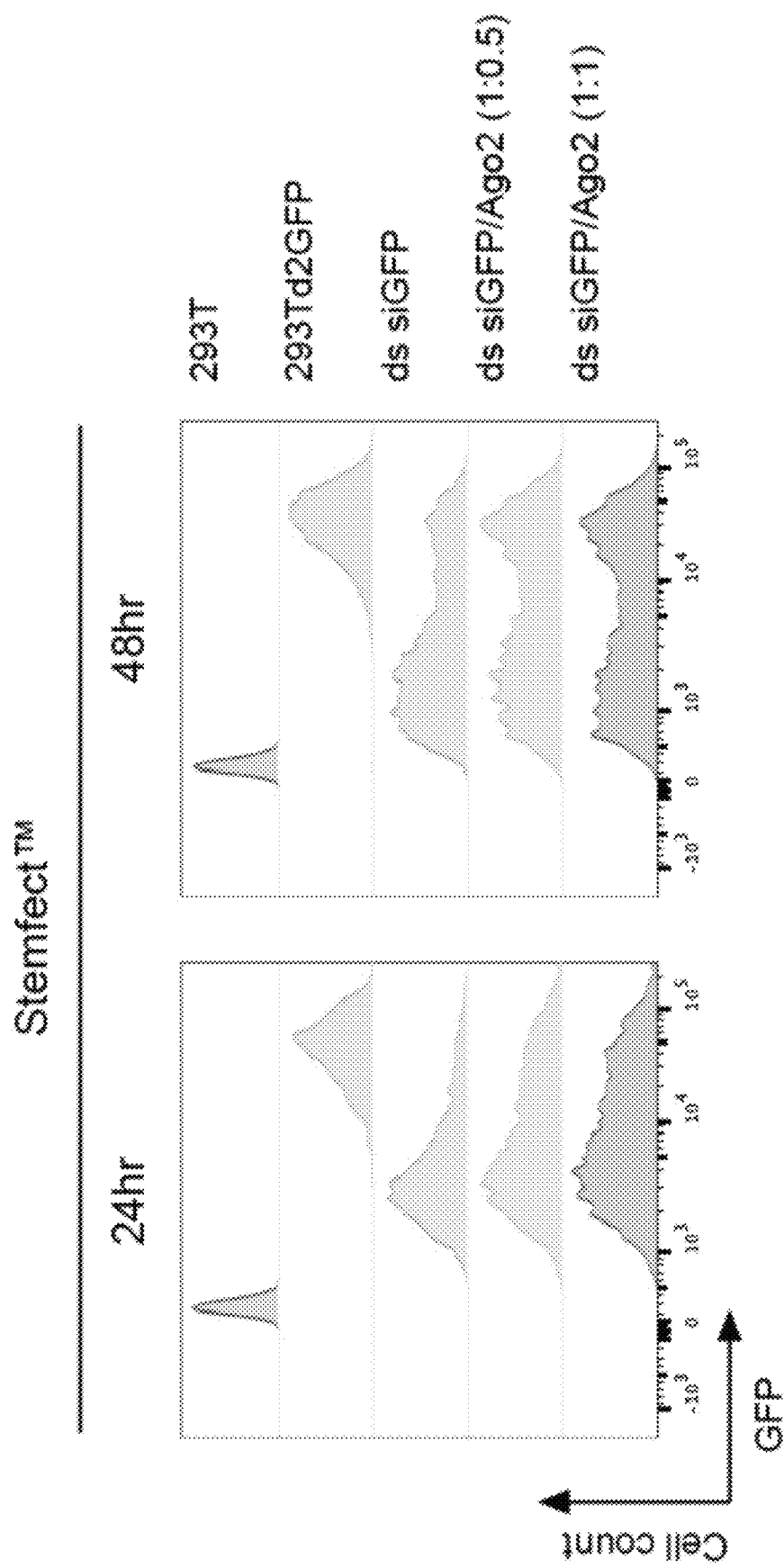

FIG. 7A and FIG. 7B are histogram plots collectively showing transfection of siGFP/Ago2 complexes with RNAiMAX® and Stemfect®. 25 nM double stranded (ds siGFP) or siGFP/Ago2 at two different molar ratios (1:0.5 and 1:1) were transfected into 293Td2GFP cells. GFP expression was quantified via flow cytometry. Representative histograms of GFP expression at 24 and 48 hours posttransfection are shown for (FIG. 7A) RNAiMAX® and (FIG. 7B) Stemfect®.

Figure 8A:
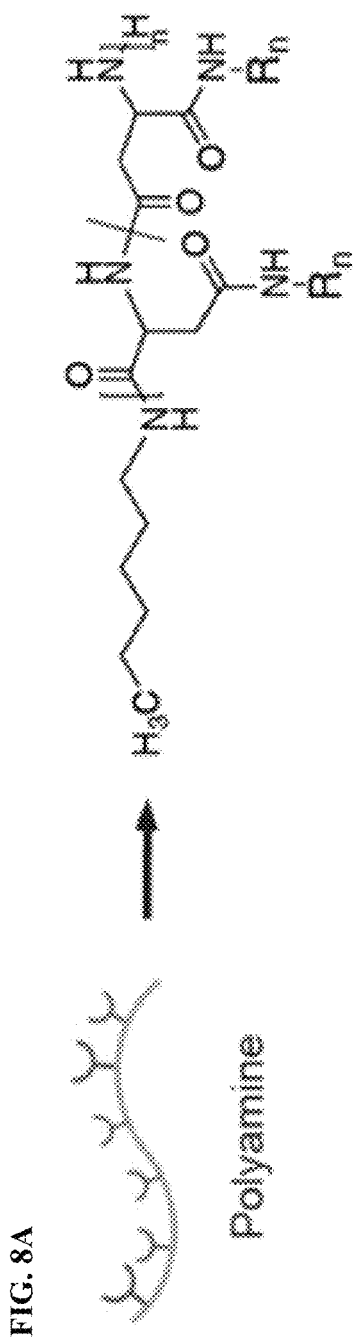
Figure 8B:
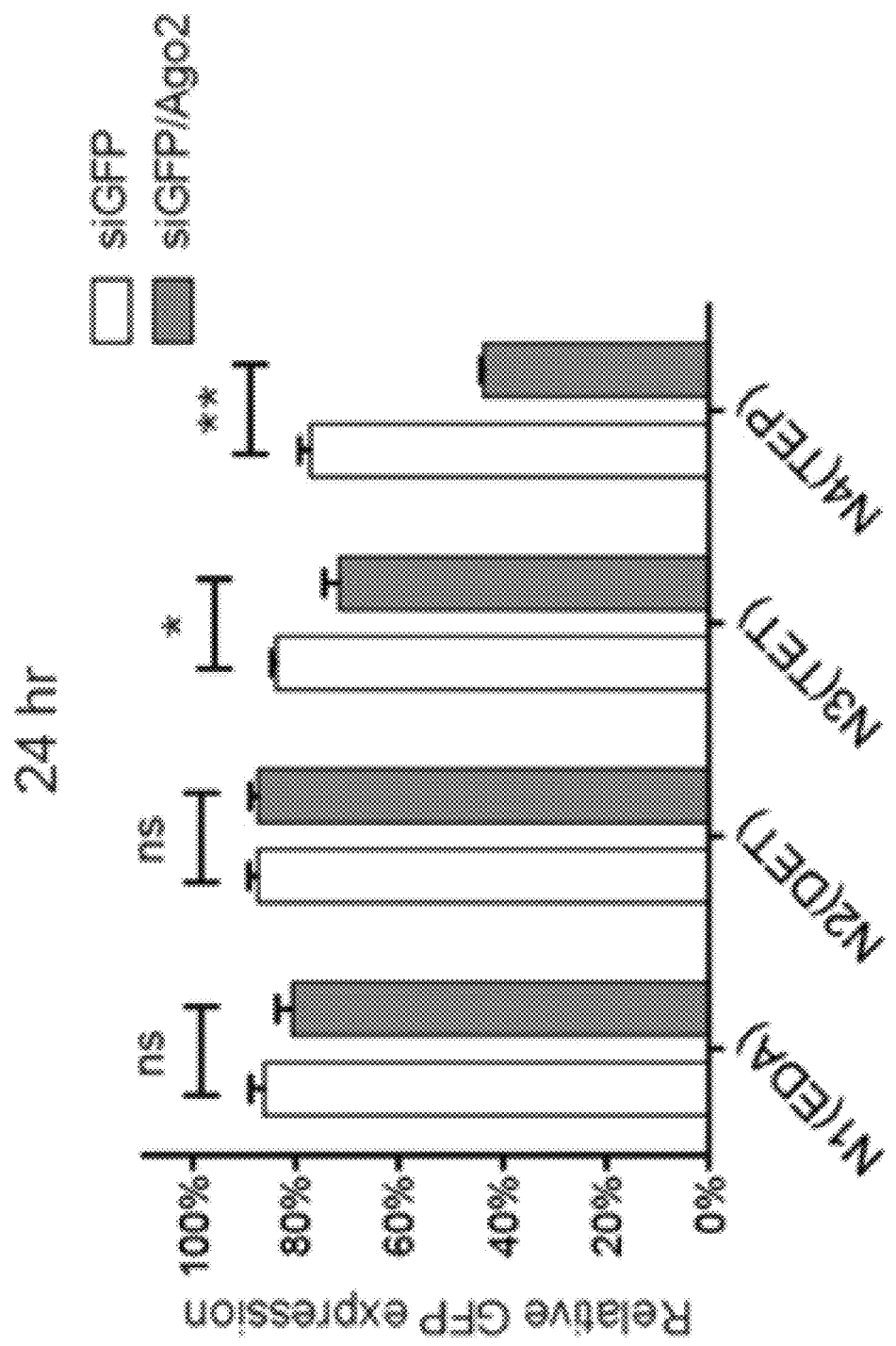
Figure 8C:
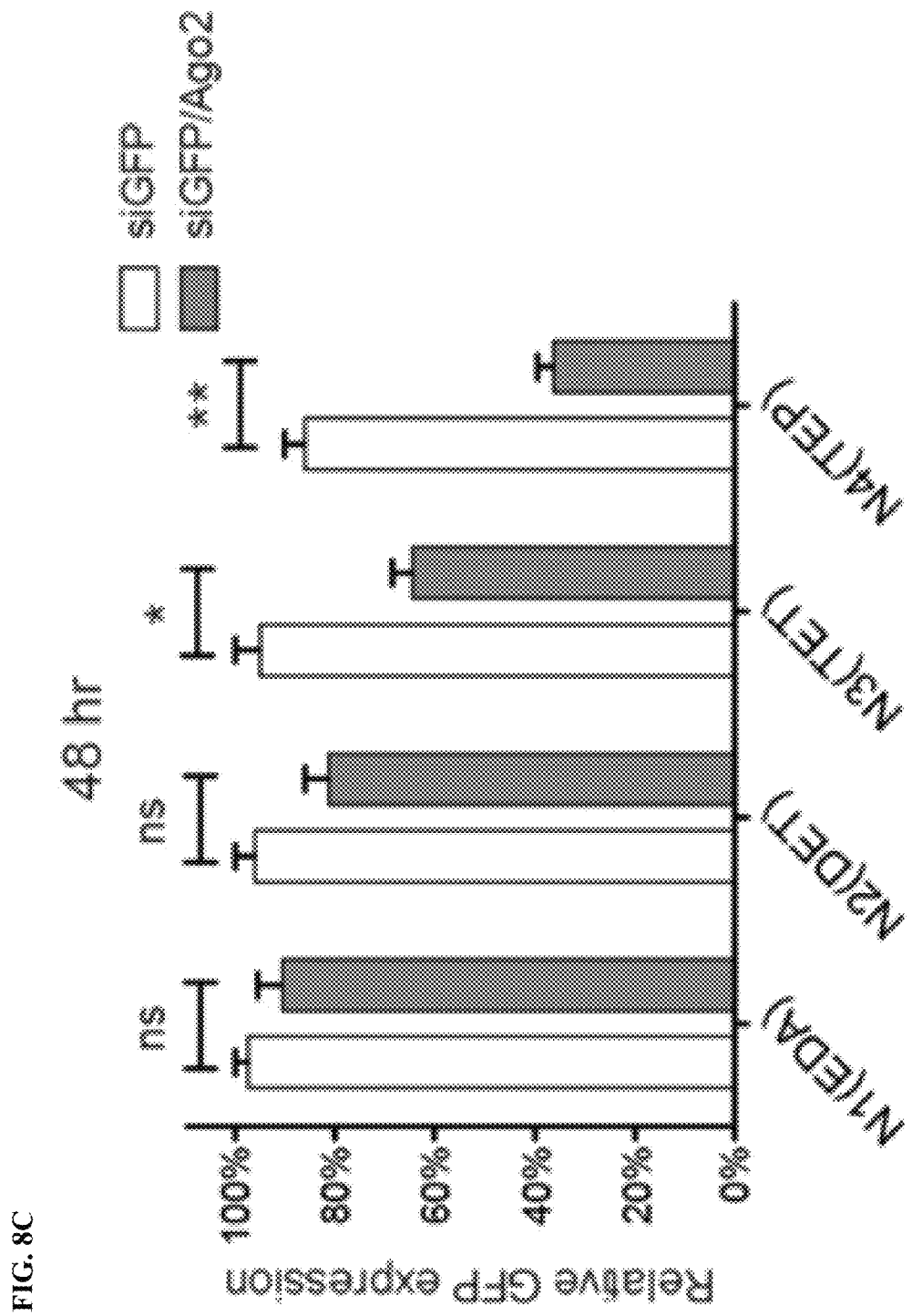
Figure 8D:
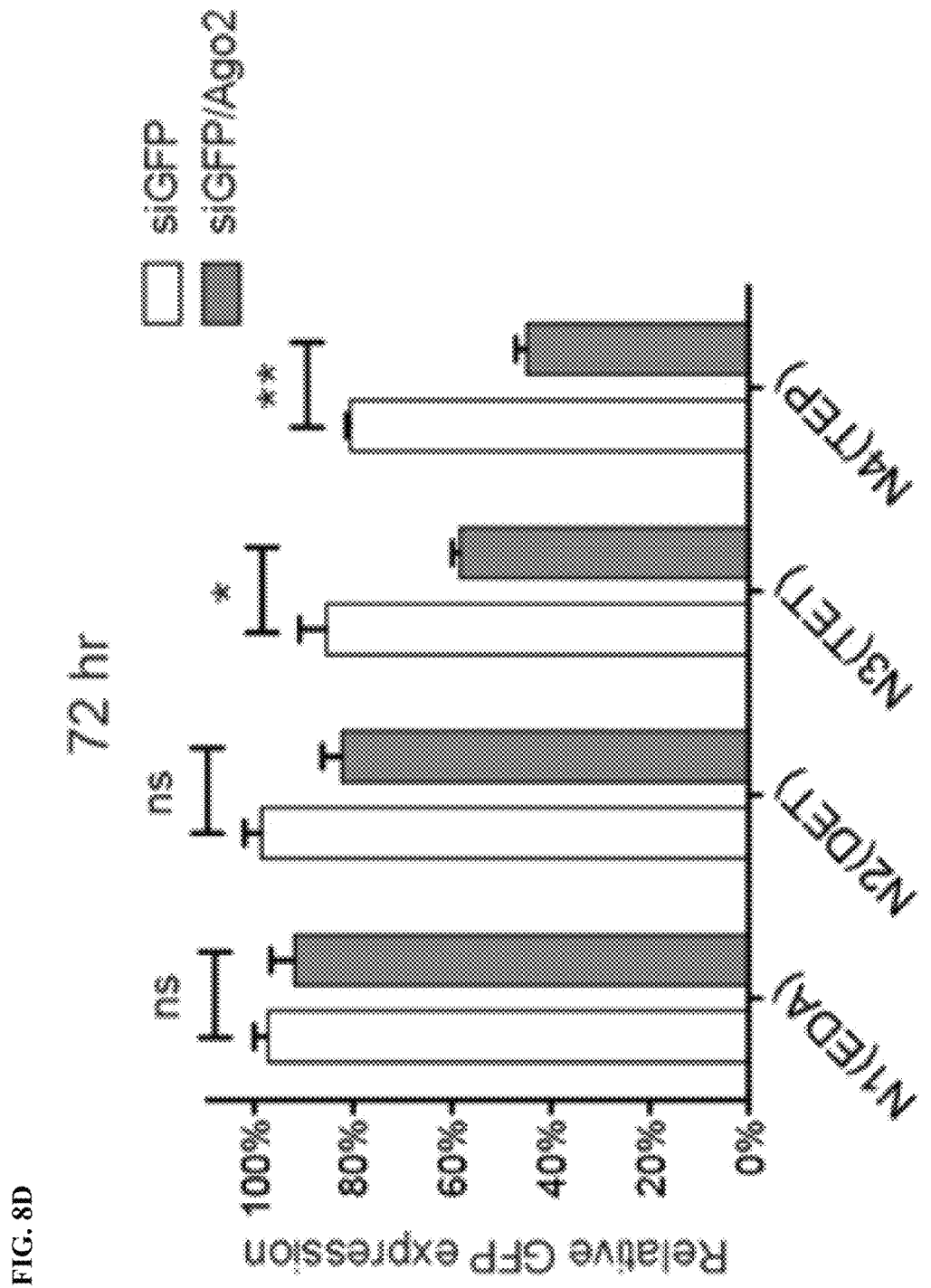
Figure 8E:
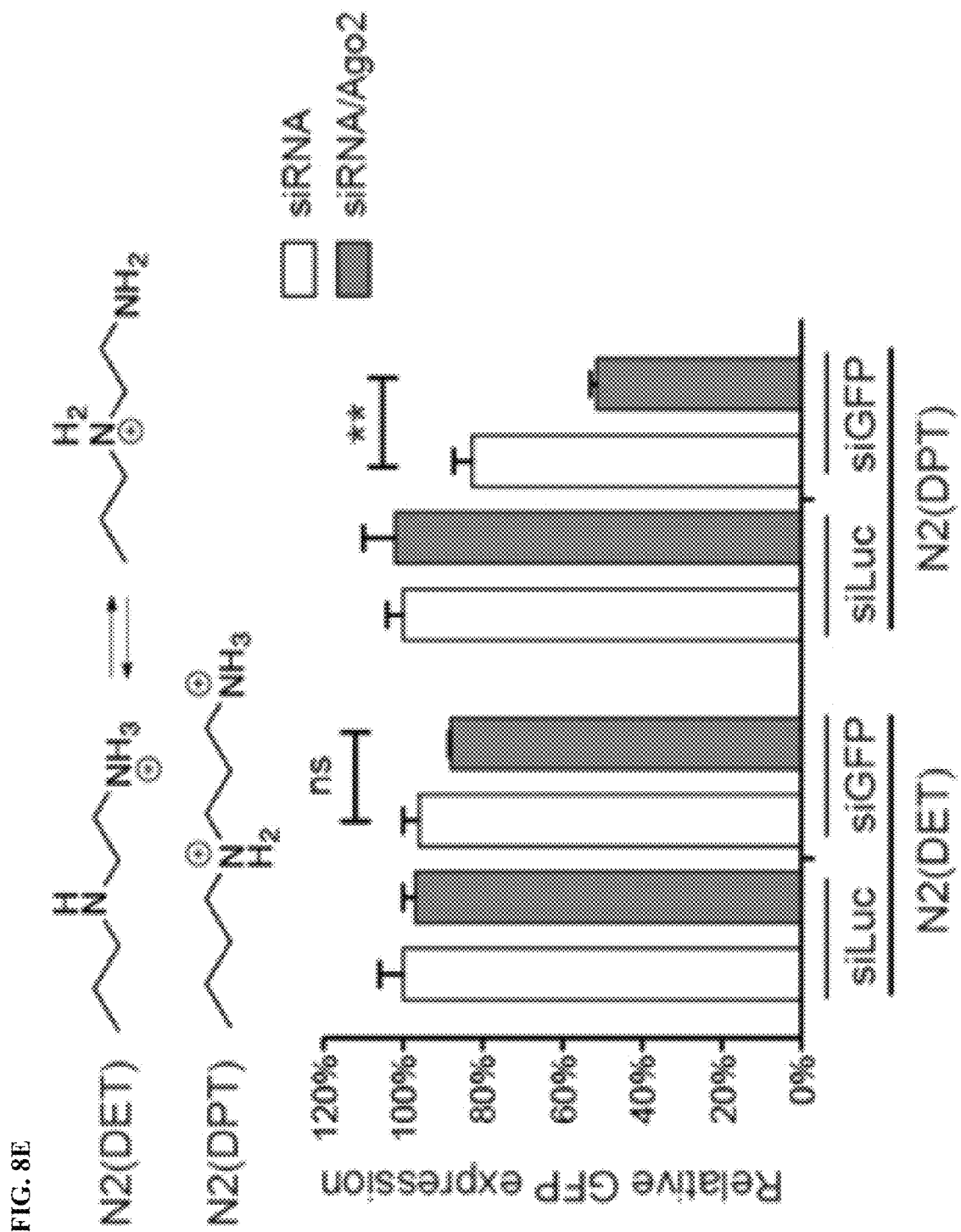

FIG. 8A shows the chemical structures and charge properties of polyamines utilized herein. Note that the amination of the backbone induces an intramolecular isomerization of the repeating unit, aspartamide, generating two isomers (Nakanishi M et al. (2007) *React Funct Polym* 67:1361-1372). Charge units on each side chain are estimated by taking into account the numbers of primary and secondary amines and the protonation degree at pH 7.4, 150 mM NaCl, 37° C., which was determined by a potentiometric titration. FIGS. 8B-8E are bar graphs collectively showing that siRNA/Ago2 complexed with polyamines induces structure-dependent gene silencing. FIGS. 8B-8D are bar graphs showing that codelivery of 100 nM ds siGFP/Ago2 resulted in enhanced GFP silencing in 293Td2GFP cells compared with siGFP alone in a polyamine side-chain-dependent manner. GFP expression was quantified via flow cytometer at (FIG. 8B) 24, (FIG. 8C) 48, and (FIG. 8D) 72 h after transfection, and was normalized to that of nontransfected 293Td2GFP cells. FIG. 8E is a bar graph showing that an increased side-chain protonation from N2 (DET) to N2 (DPT) augments GFP knockdown with siGFP and Ago2. The estimated protonated structures of N2 (DET) and N2 (DPT) at pH 7.4 are shown at the top. ss siLuc and ds siLuc was used as a nontargeting control. Mean fluorescence intensity of GFP expression was quantified via flow cytometry and normalized to that of 293Td2GFP cells. Data are represented as the mean±SEM (n=3). *P<0.05, **P<0.01, ns, no significance.

Figure 9:
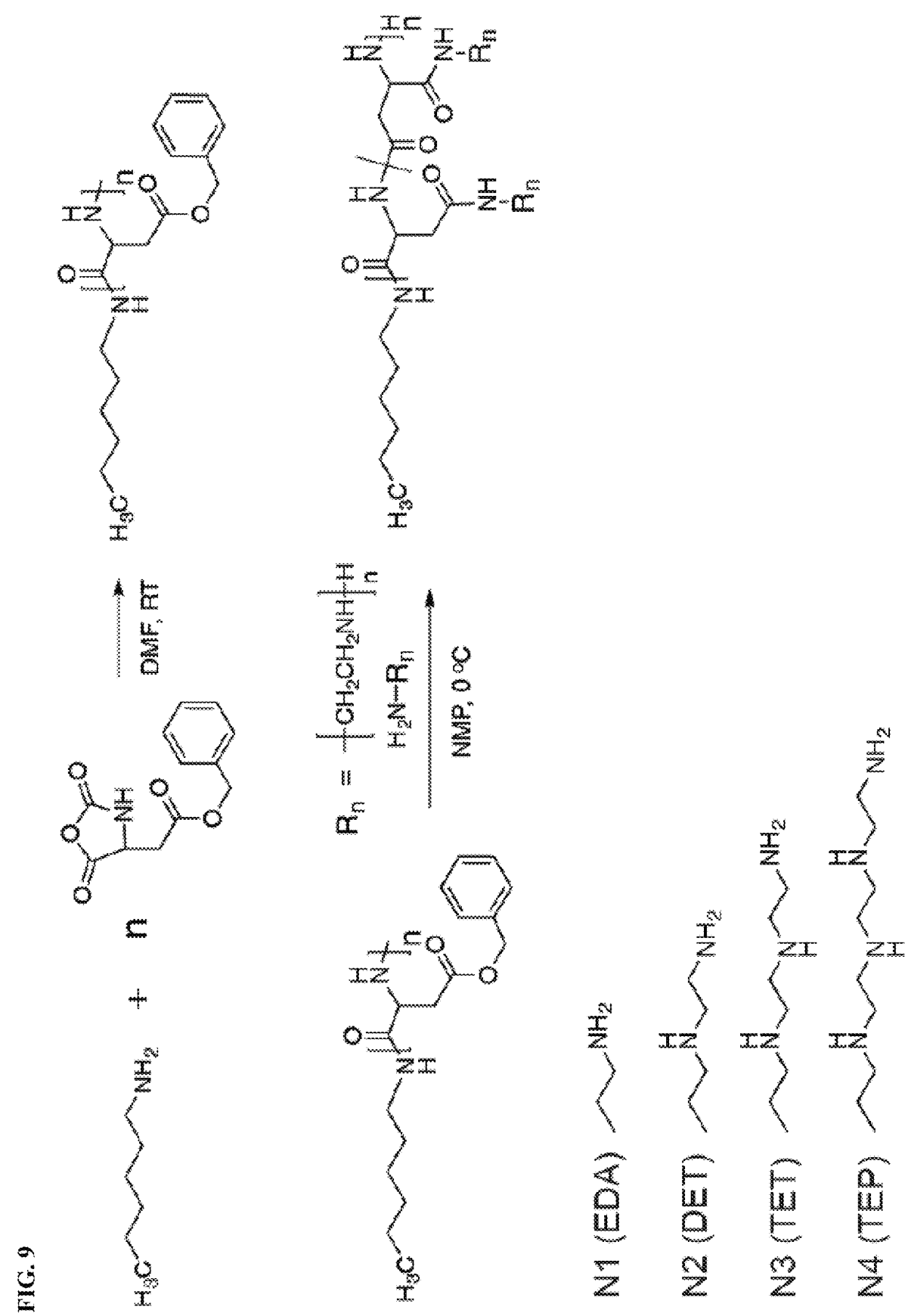

FIG. 9 shows the chemical structures and derivations of the N-substituted polyamines. Polyamines were derived using Ncarboxyanhydride polymerization of L-benzyl aspartate, followed by exhaustive amination of the side chain with various N-amine substituents bearing one to four aminoethylene repeats in the side chain. During the amination, an intramolecular isomerization of the repeating unit, aspartamide, generates two isomers according to a previous study (Nakanishi M et al. (2007) *React Funct Polym* 67:1361-1372).

Figure 10A:
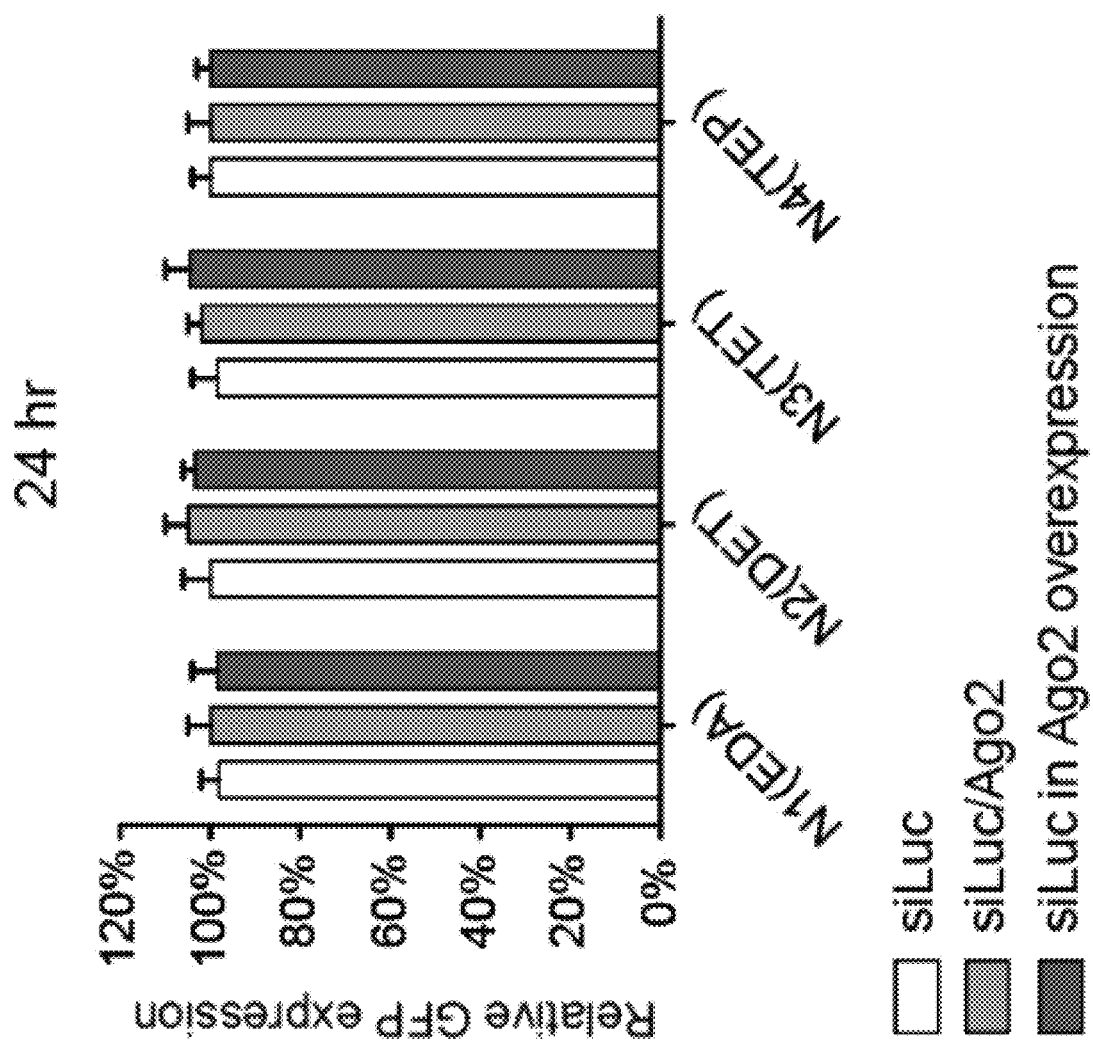
Figure 10B:
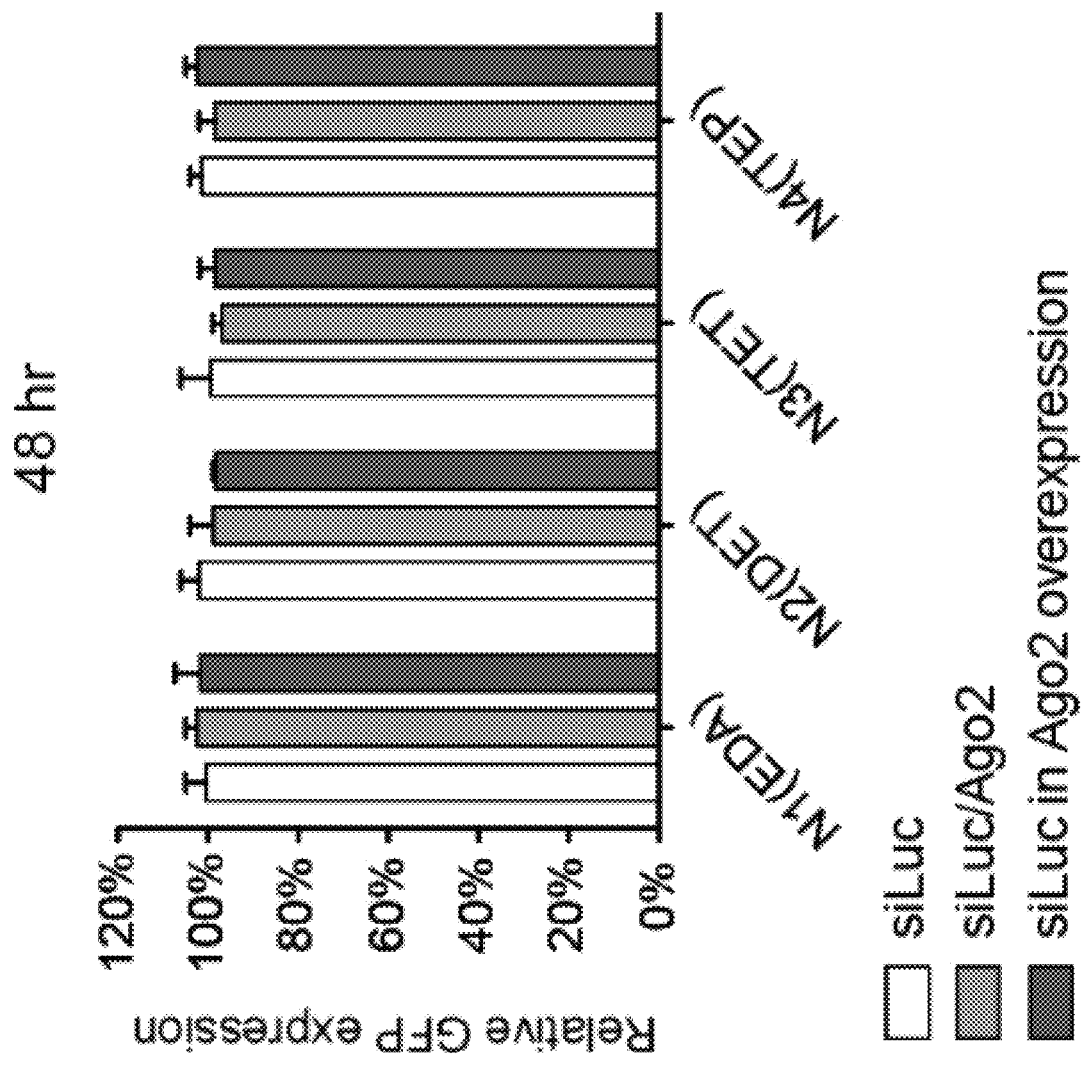
Figure 10C:
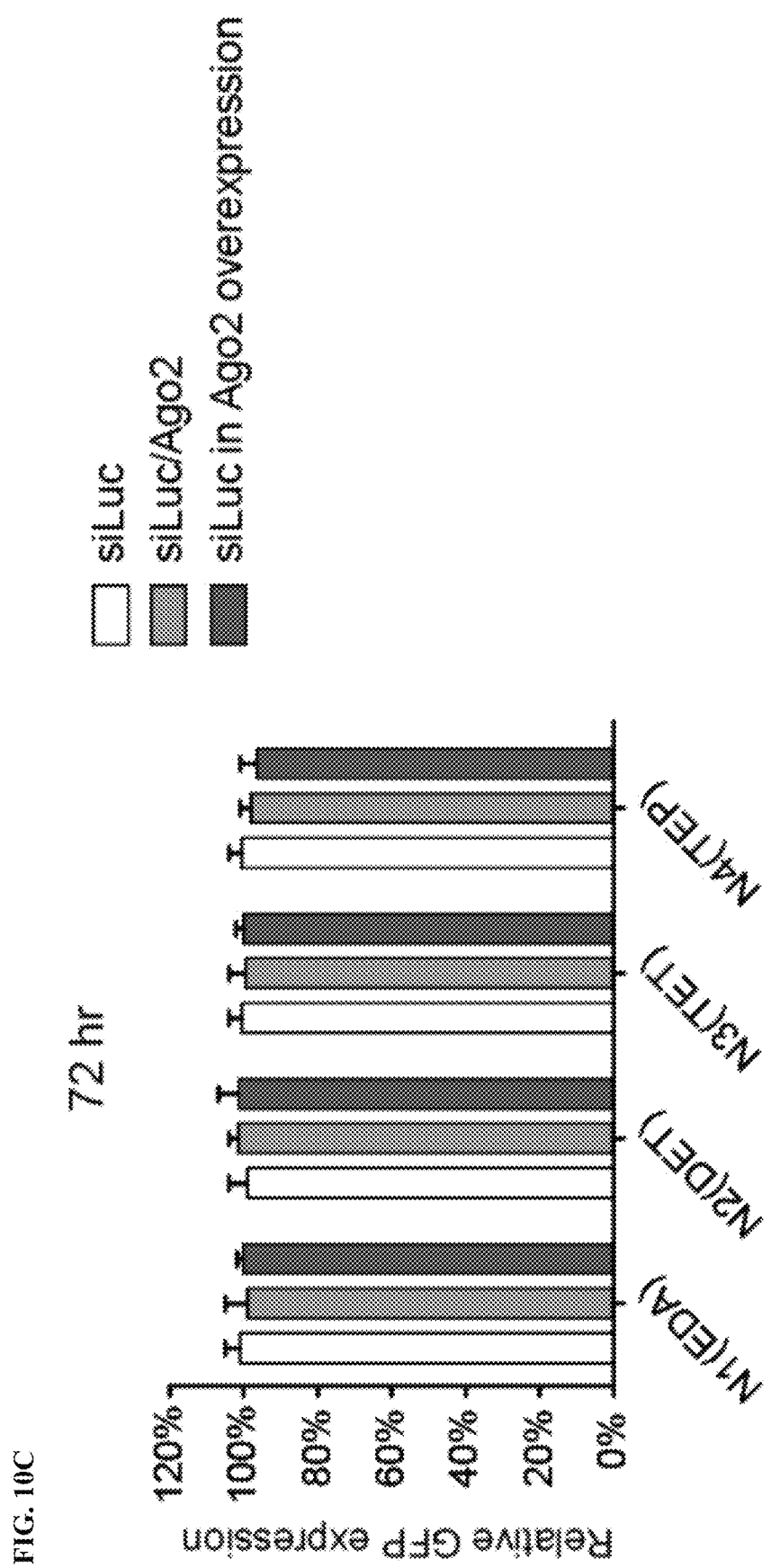
Figure 11A:
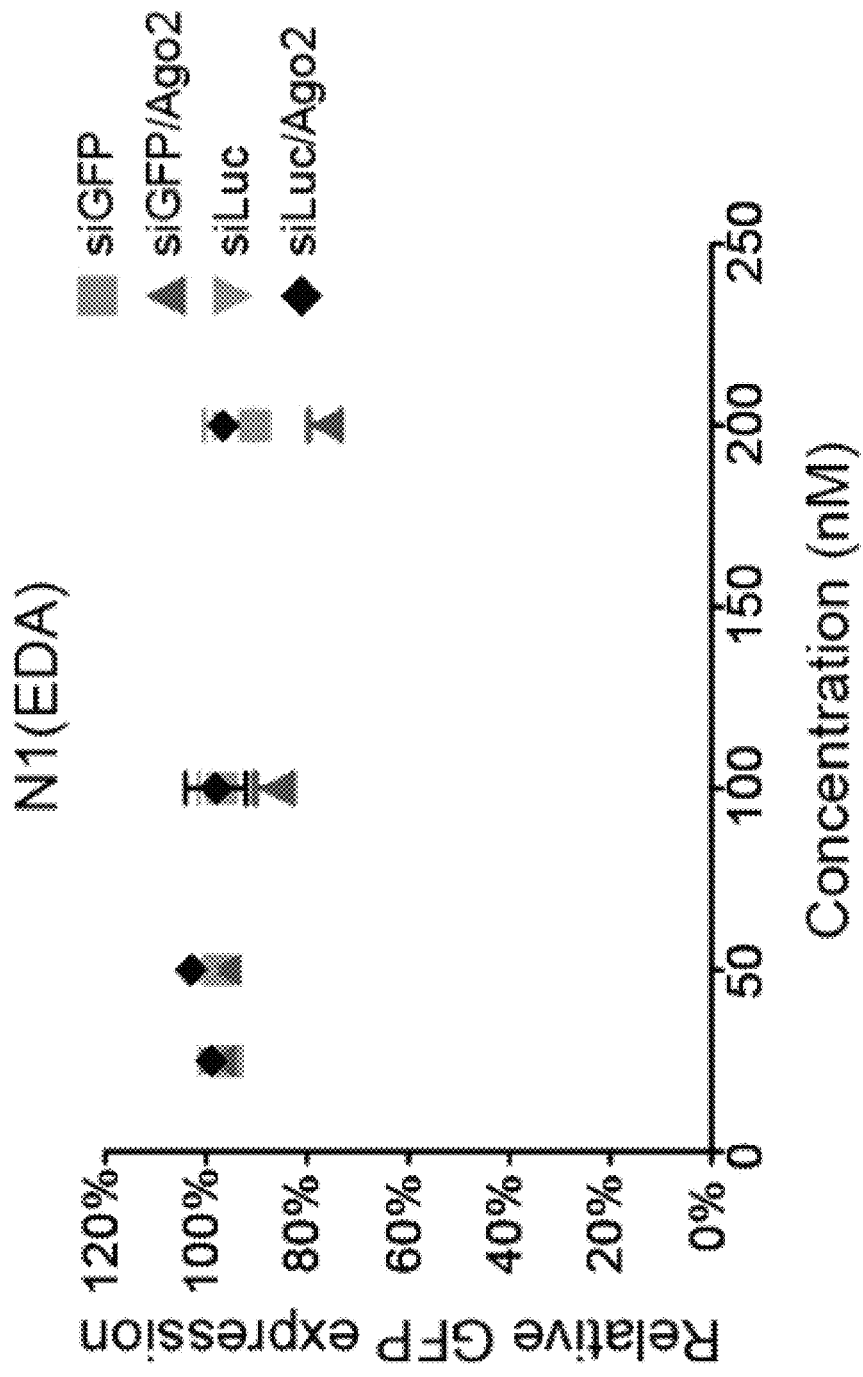
Figure 11B:
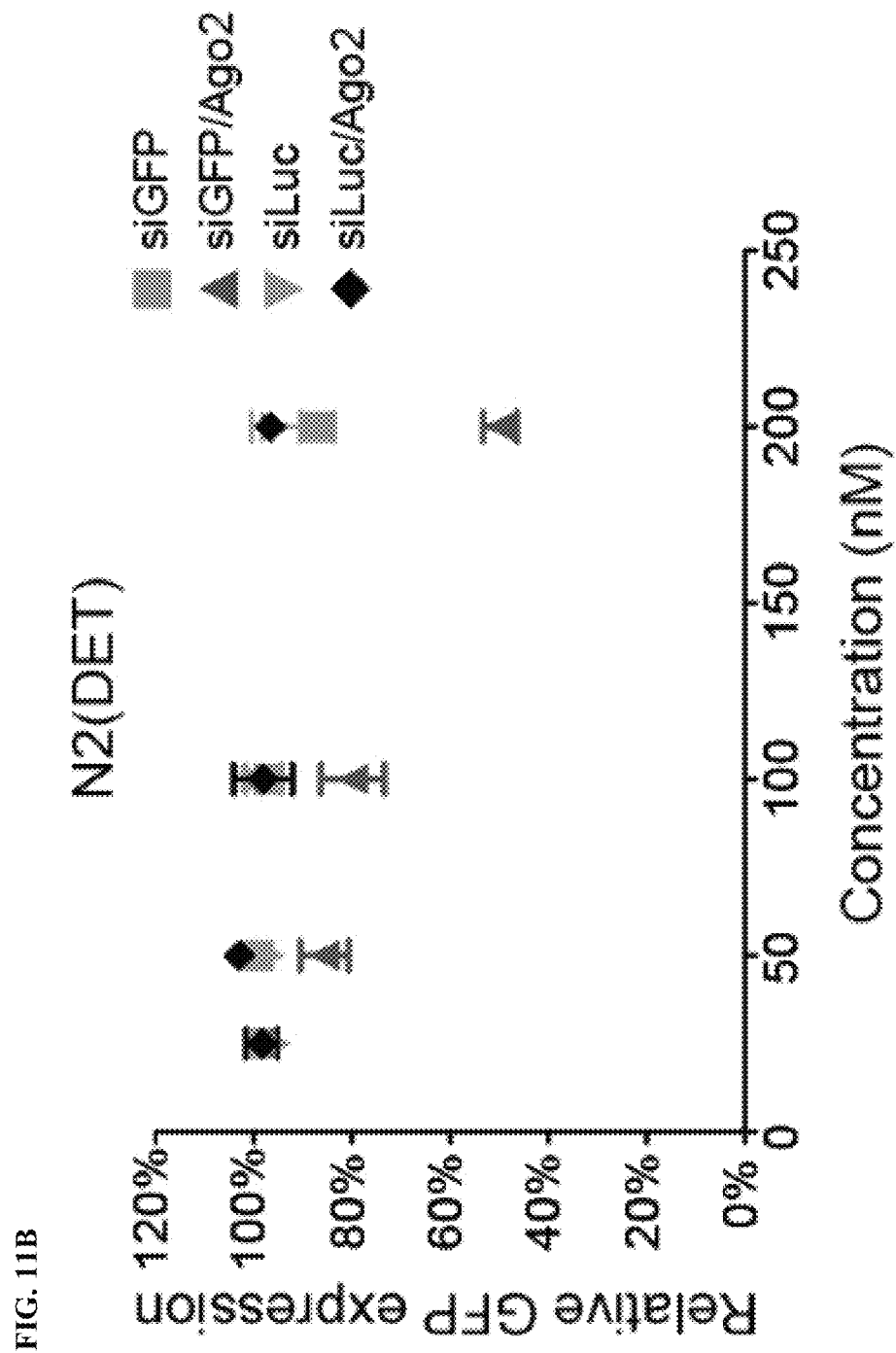
Figure 11C:
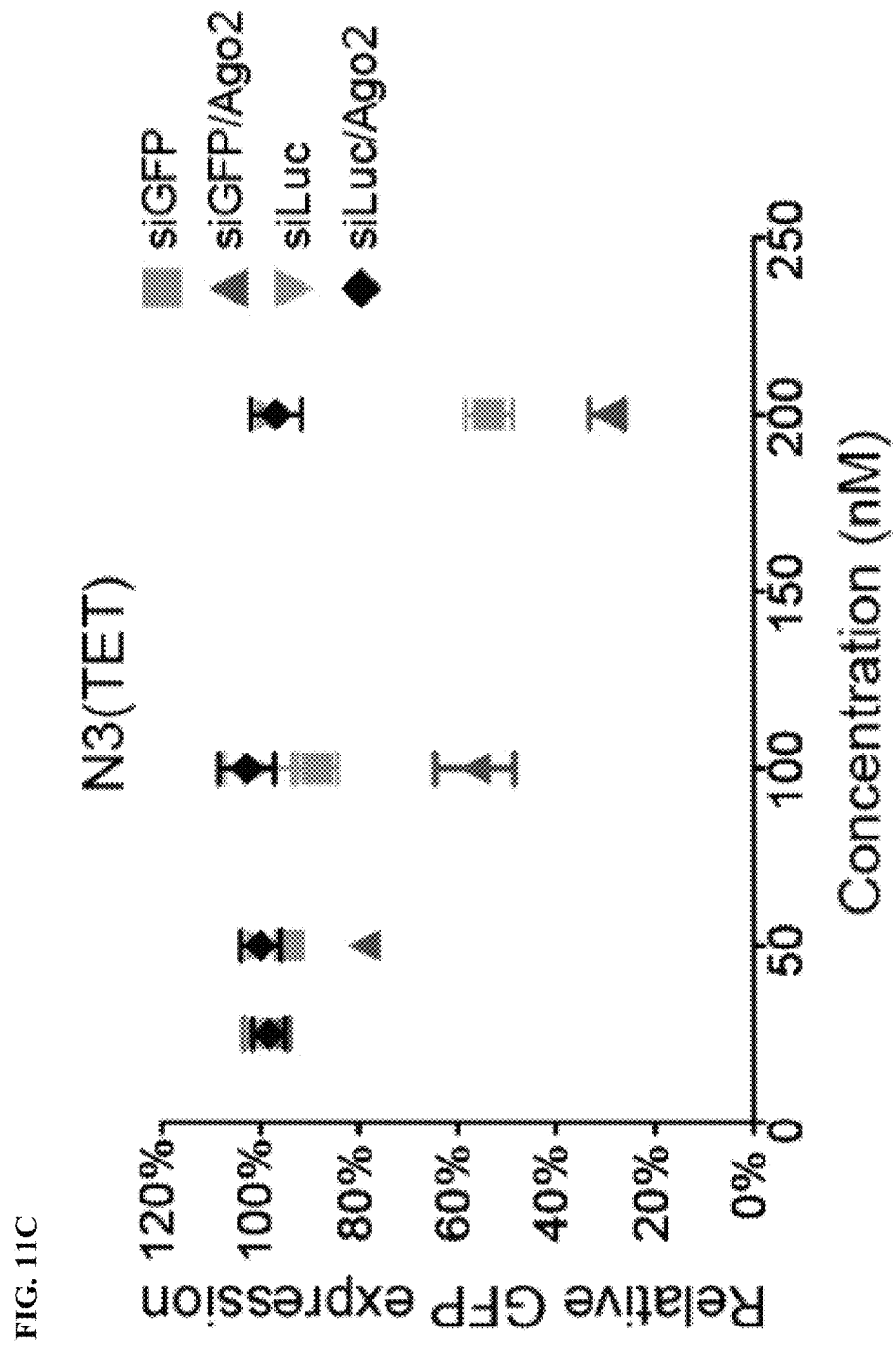
Figure 11D:
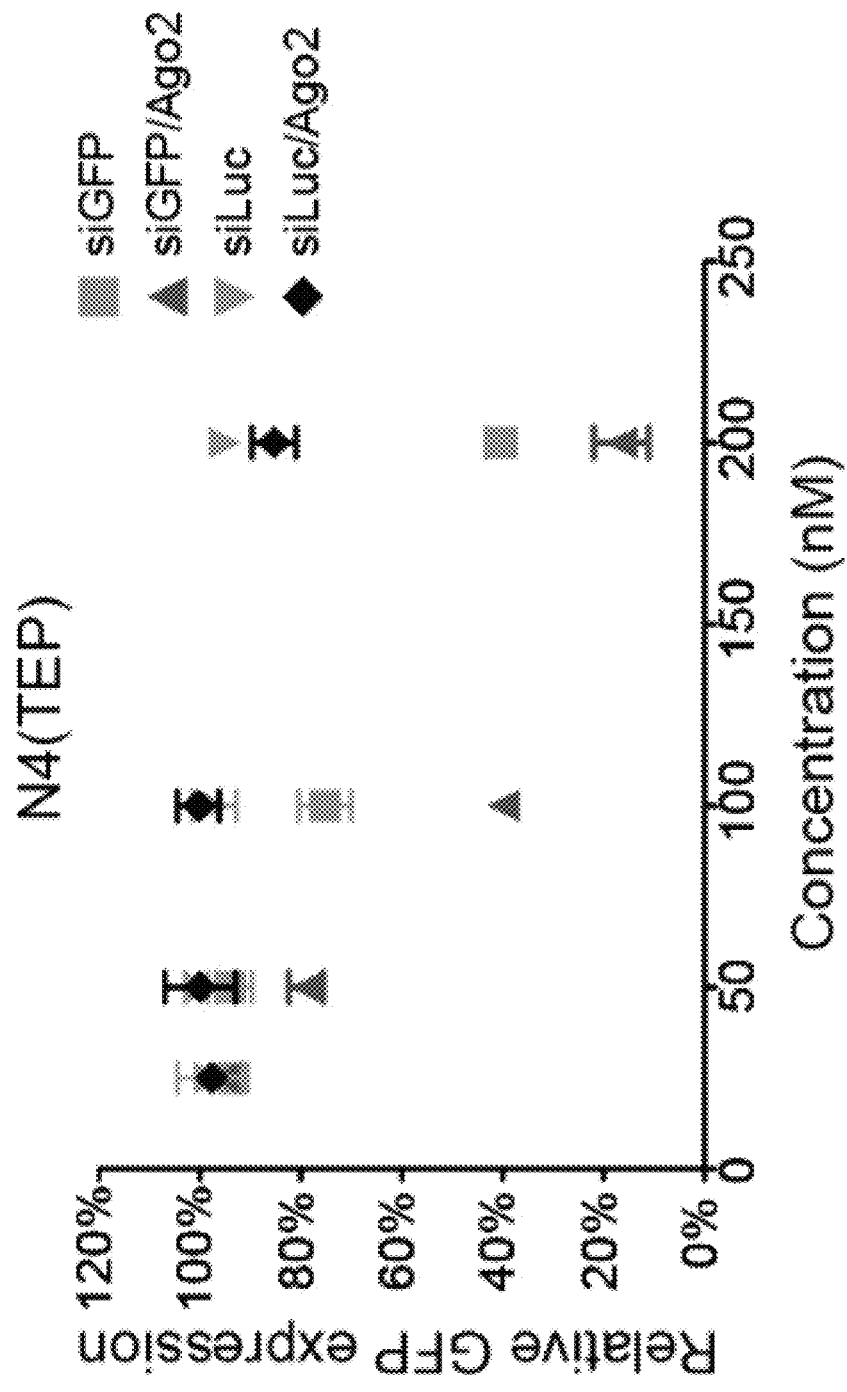

FIGS. 10A-10C are bar graphs collectively depicting the lack of off-target silencing in co-transfection of Ago2 protein or Ago2 overexpression. Transfection of 100 nM double stranded anti-luciferase siRNA (siLuc) alone, siLuc/Ago2 (1:1 molar ratio) or transfection of siLuc in Ago2-overexpressing cells did not result in GFP silencing in 293Td2GFP cells. GFP expression was quantified via flow cytometer at (FIG. 10A) 24, (FIG. 10B) 48, and (FIG. 10C) 72 hours after transfection. Data are represented as the mean±SEM (n=3) relative to nontransfected 293Td2GFP cells.

FIGS. 11A-11D are plots of relative GFP expression collectively depicting the effect of Ago2 incorporation on silencing by siRNA via polyamines over a range of concentrations. Transfection of 25, 50, 100 and 200 nM double stranded anti-GFP siRNA (siGFP) alone, siGFP/Ago2 (1:1 molar ratio), siLuc (negative control) and siLuc/Ago2 (1:1 molar ratio) in 293Td2GFP cells. GFP expression was quantified via flow cytometer at 48 hours after transfection. Data are represented as the mean±SEM (n=3) relative to nontransfected 293Td2GFP cells.

Figure 12A:
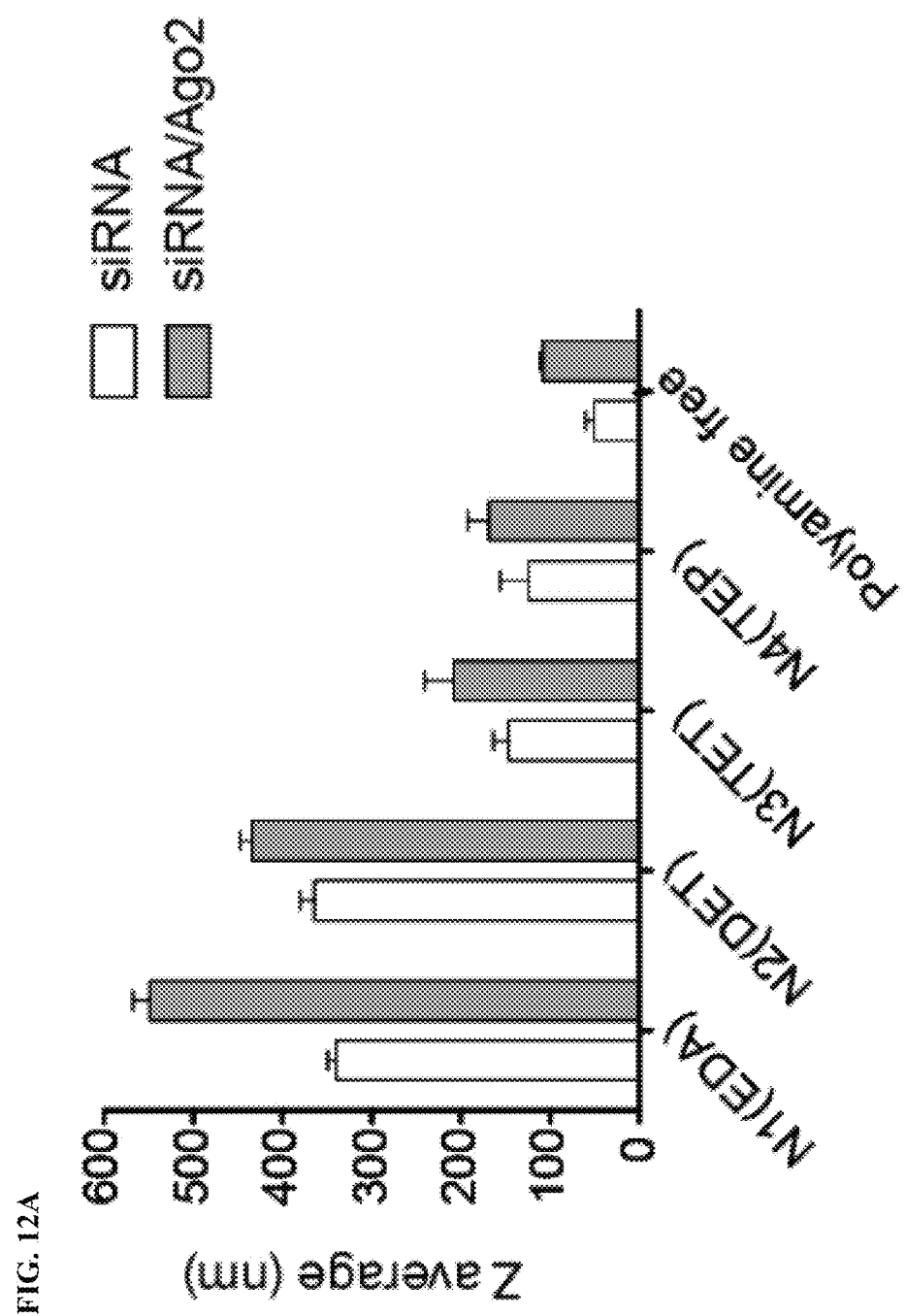
Figure 12B:
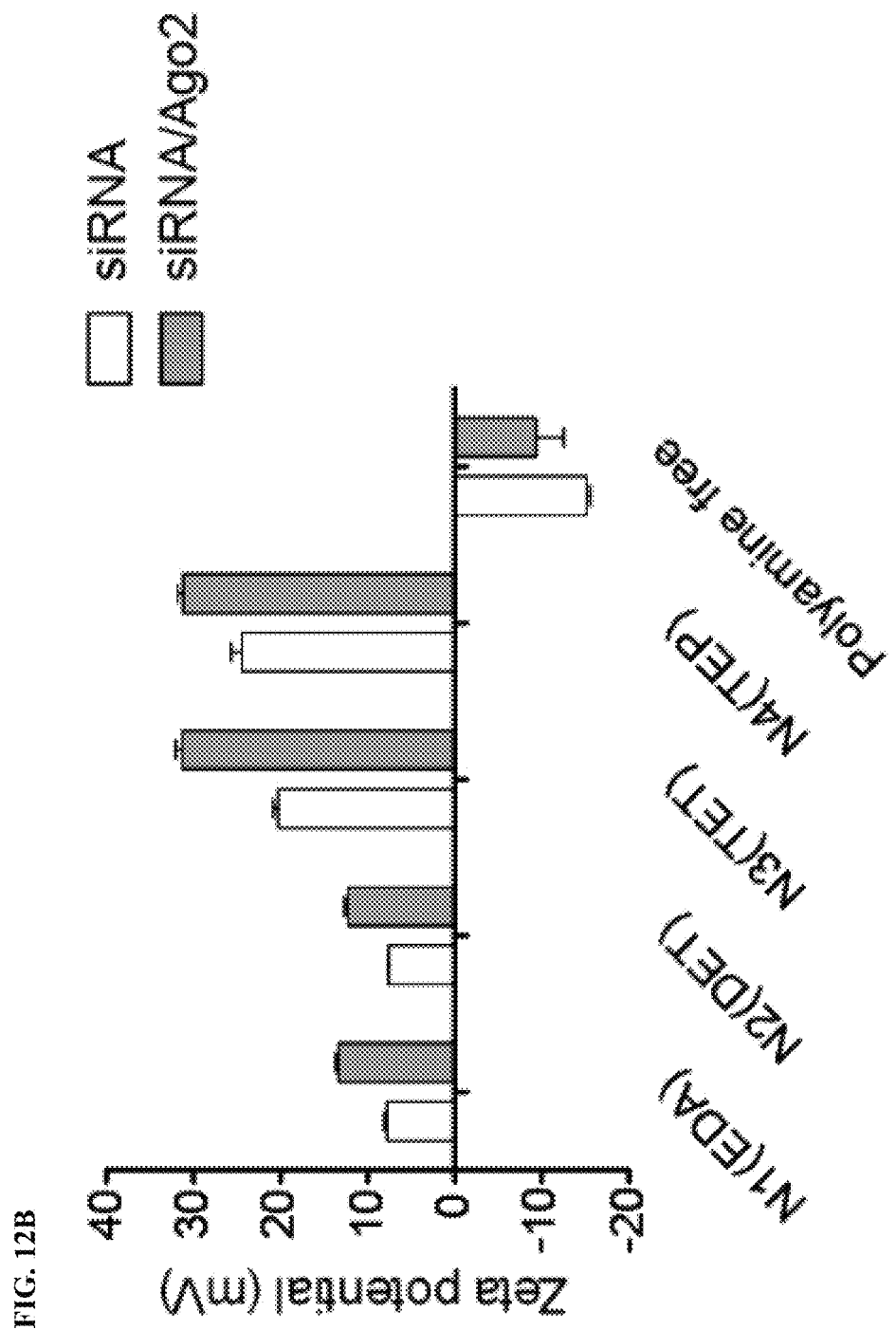
Figure 12C:
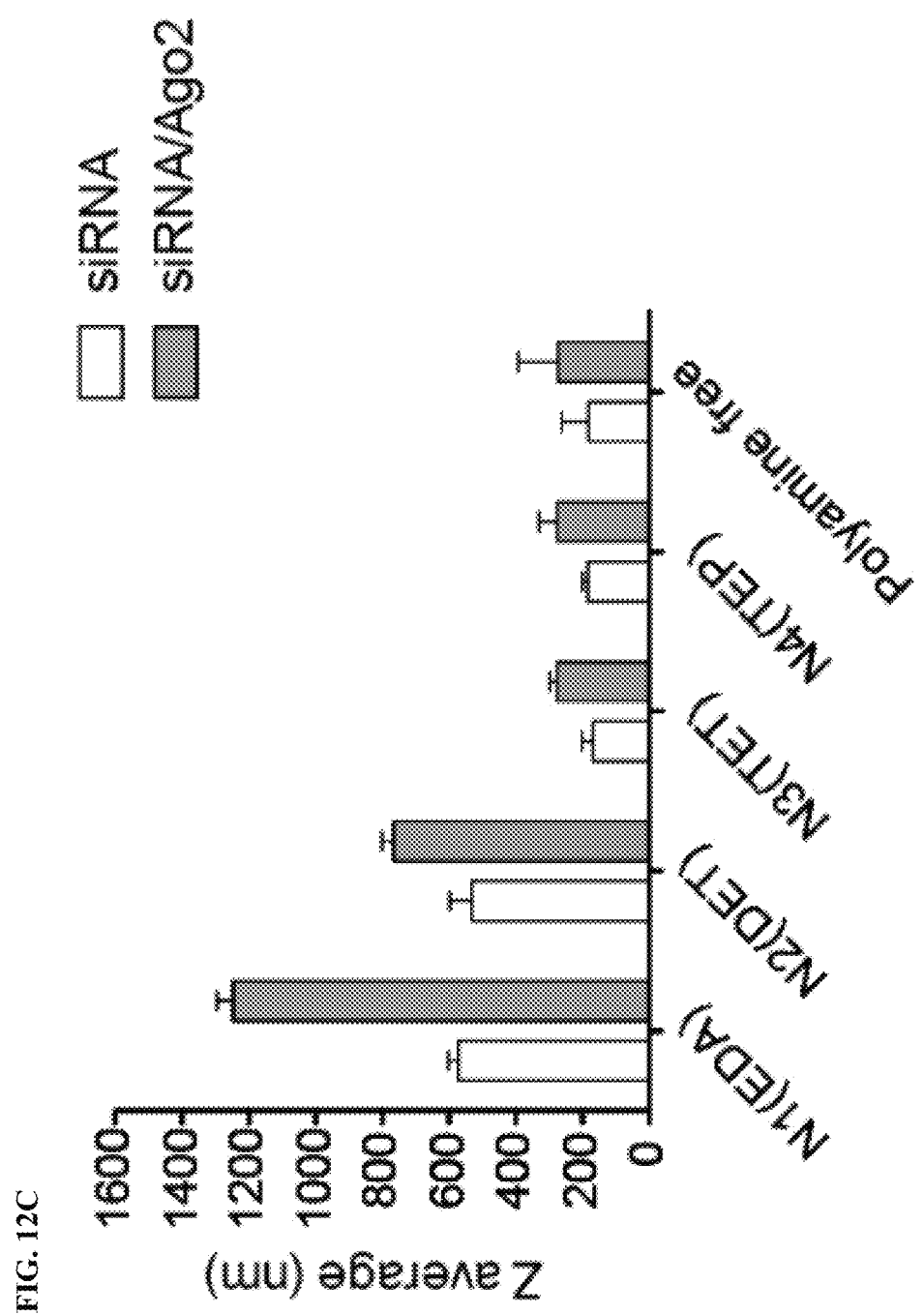
Figure 12D:
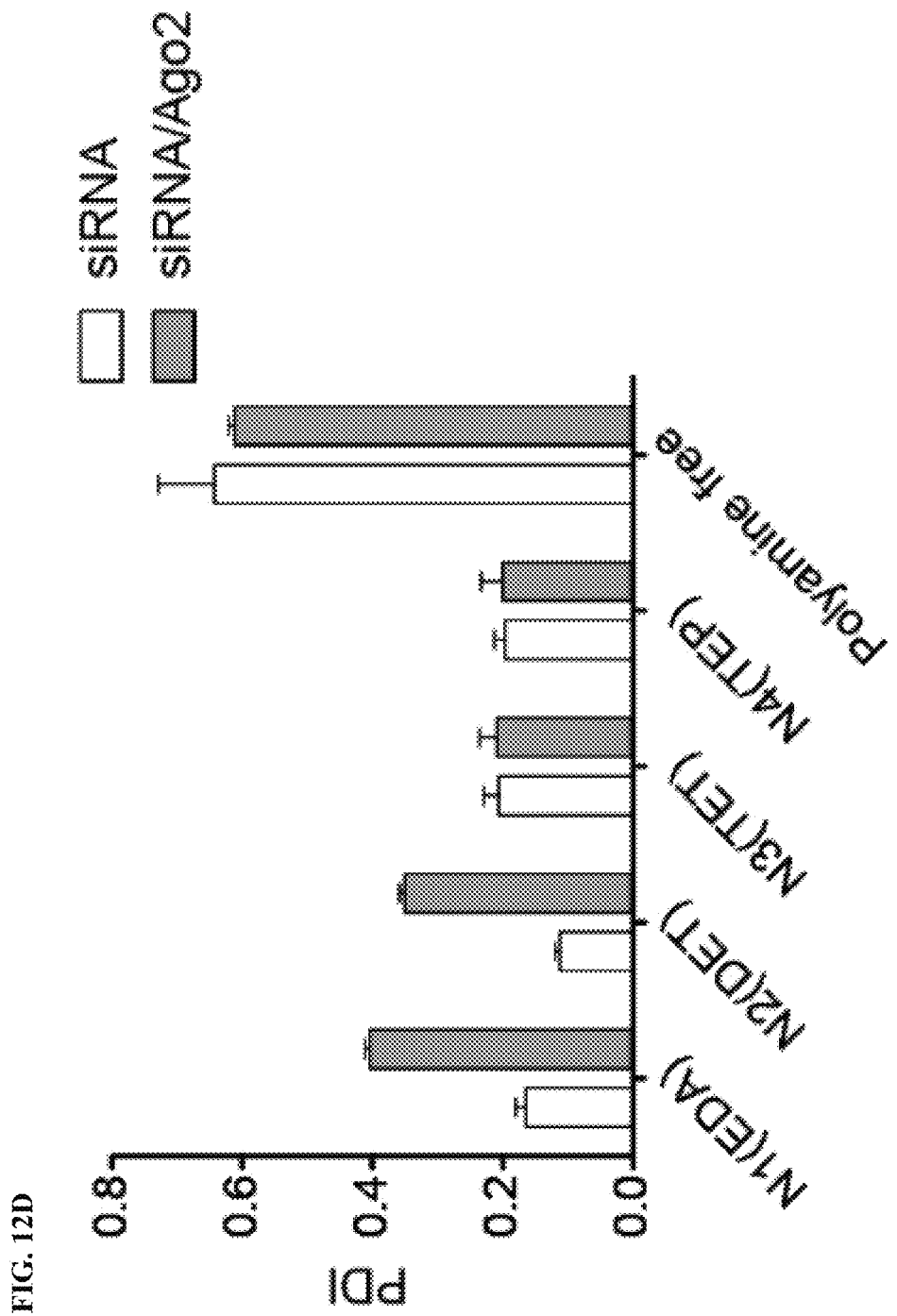

FIGS. 12A-12D are bar graphs collectively depicting the physiochemical properties of siRNA/Ago2 complexes characterized by dynamic light scattering. FIG. 12A and FIG. 12B are bar graphs showing the sizes (FIG. 12A) and zeta potentials (FIG. 12B) of siRNA/polyamines and siRNA/Ago2/polyamines at a concentration of 5 μg/ml siRNA in 20 mM HEPES buffer. FIG. 12C and FIG. 12D are bar graphs showing the sizes (FIG. 12C) and polydispersity indices (PDI) (FIG. 12D) of complexes in 20 mM HEPES buffer containing 10% fetal bovine serum.

Figure 13:
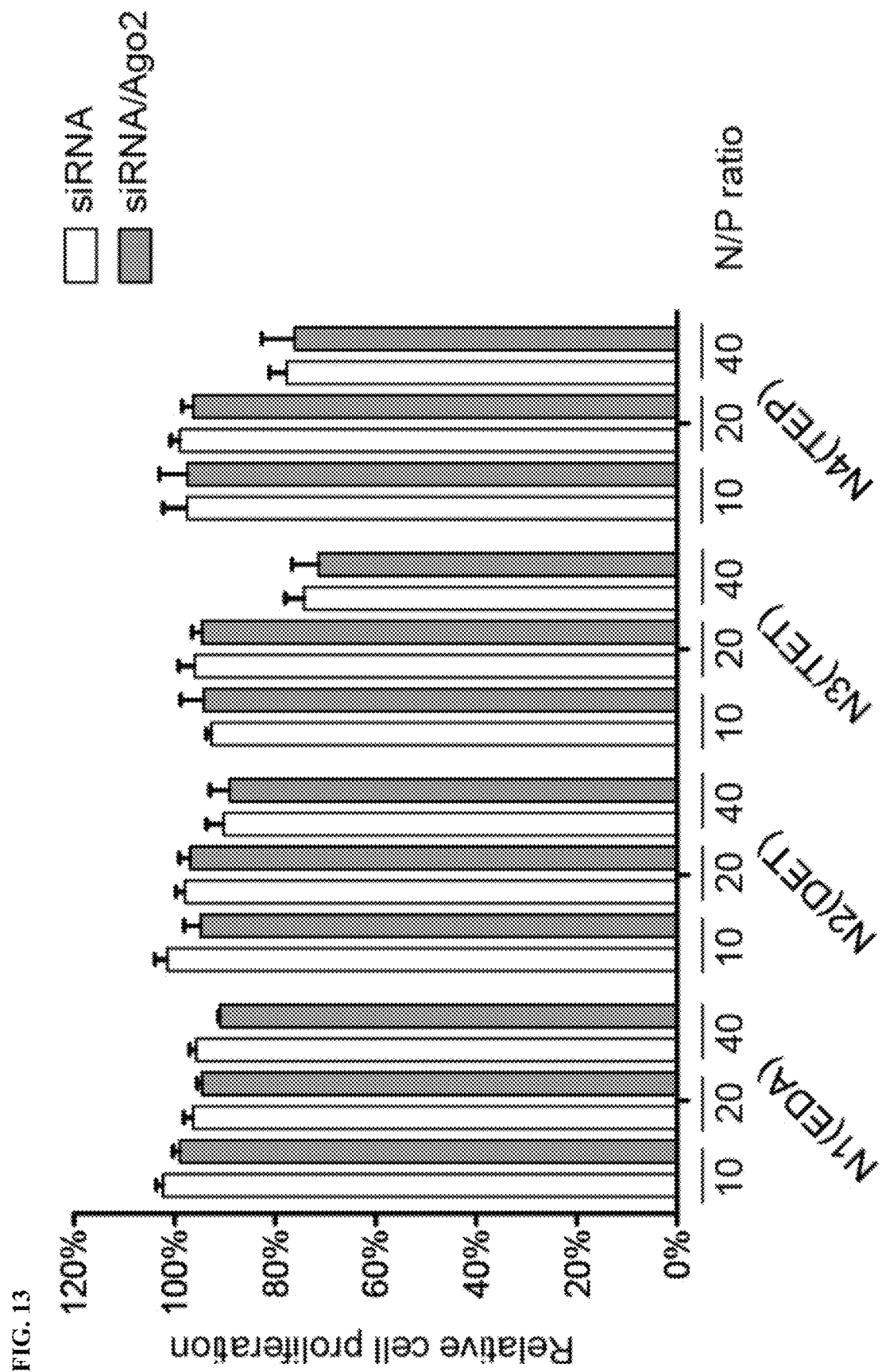

FIG. 13 is a bar graph depicting the effect of polyamines on proliferation of fibroblast cells. 100 nM siRNA or siRNA/Ago2 (1:1 molar ratio) was transfected into mouse fibroblast cells at N/P ratios (number of protonatable amine on polyamine relative to that of phosphate on siRNA) of 10:1, 20:1 and 40:1. Cells were seeded at 20000 cells per well in 96-well plates. 48 hours after transfection, a MTT assay was performed to measure cell proliferation relative to nontransfected NIH3T3 cells.

Figure 14A:
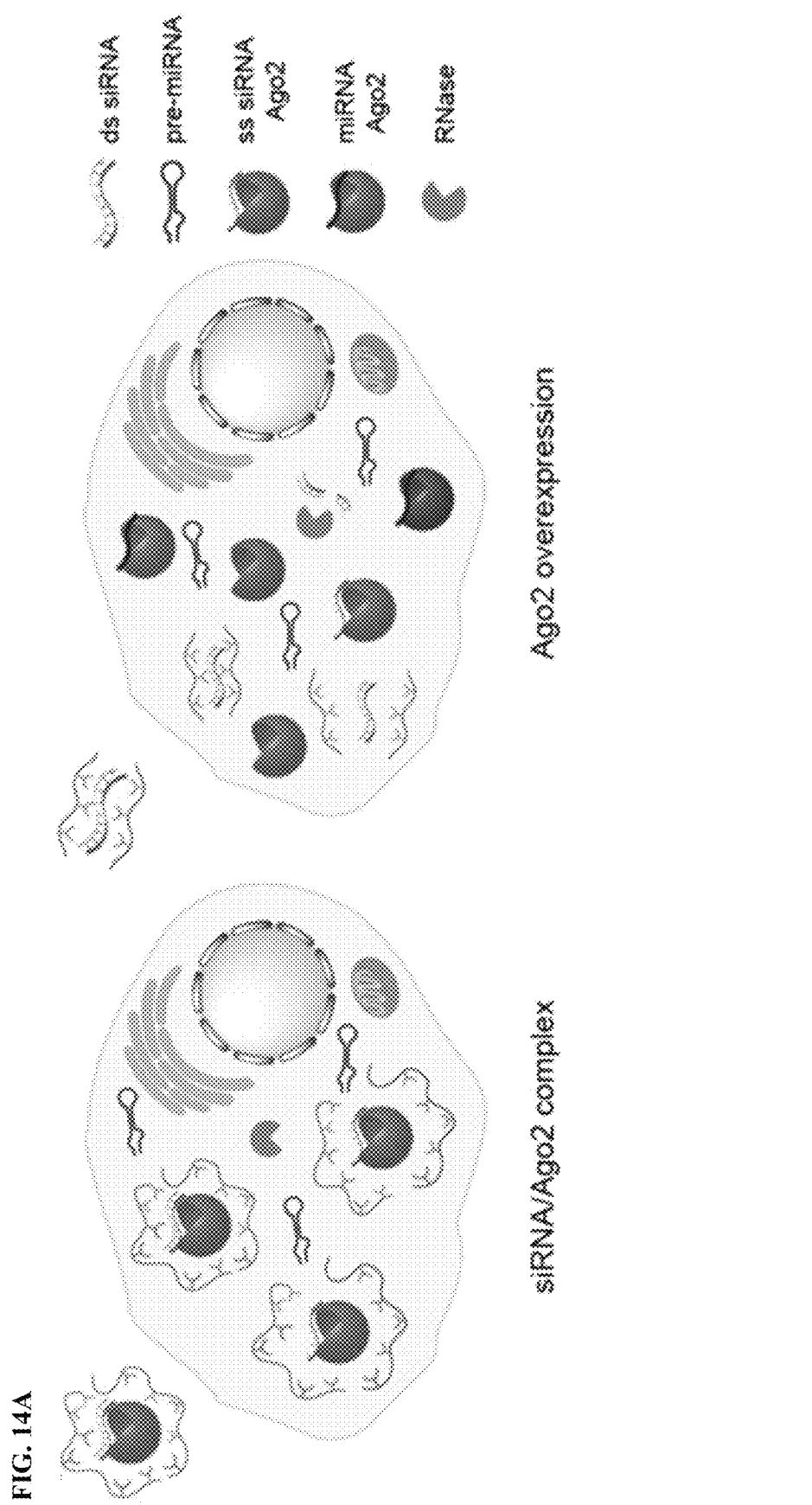
Figure 14B:
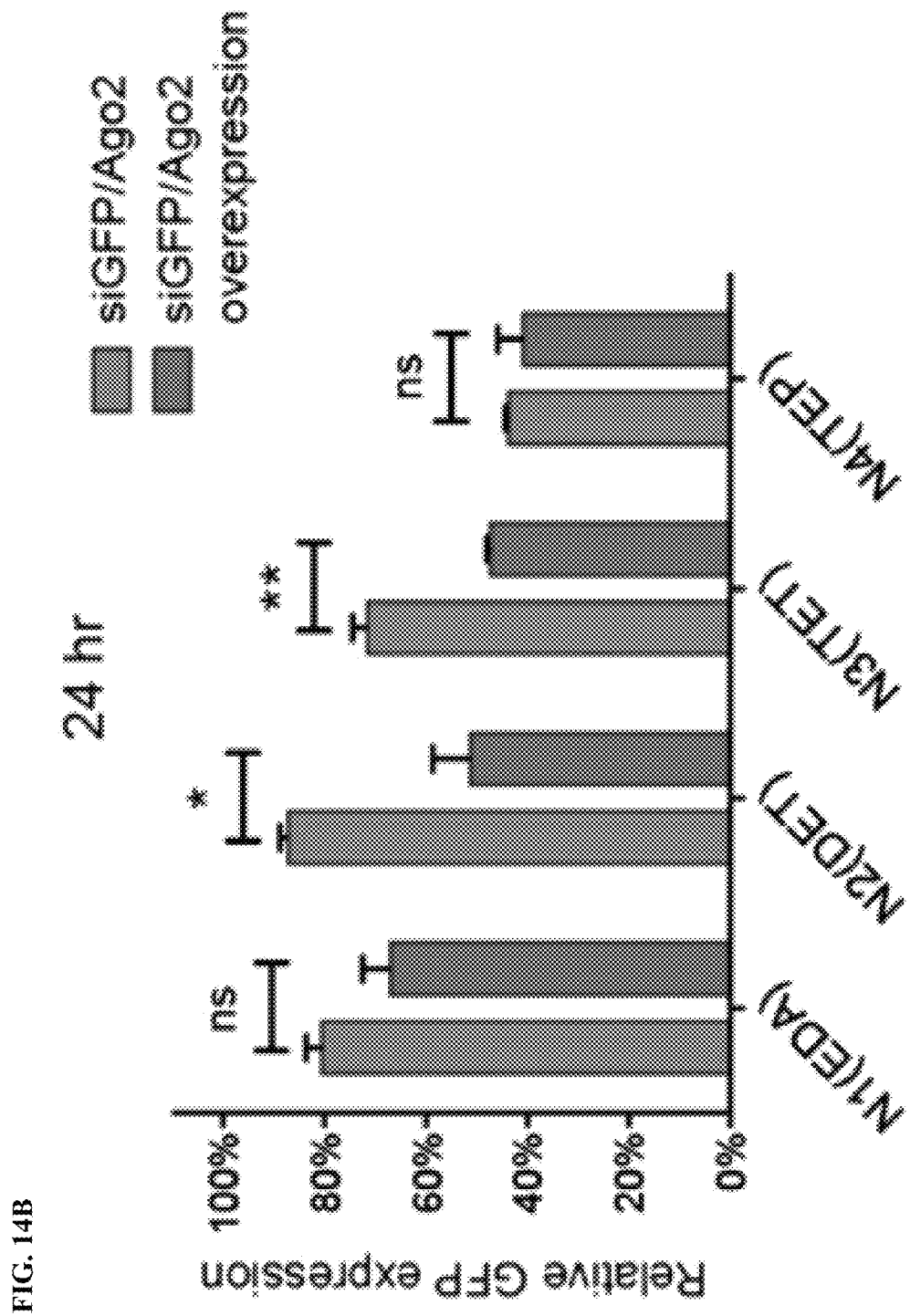
Figure 14C:
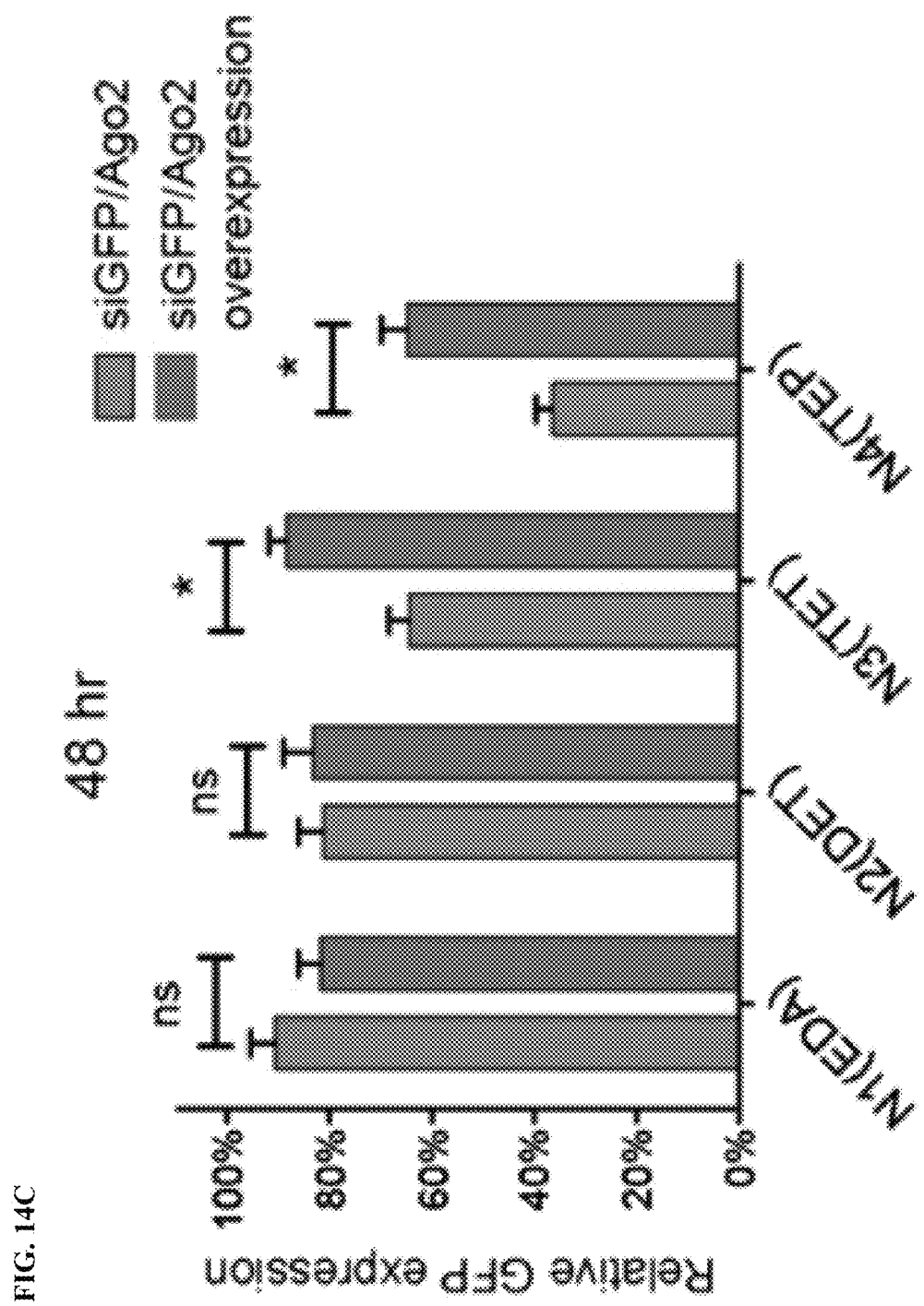
Figure 14D:
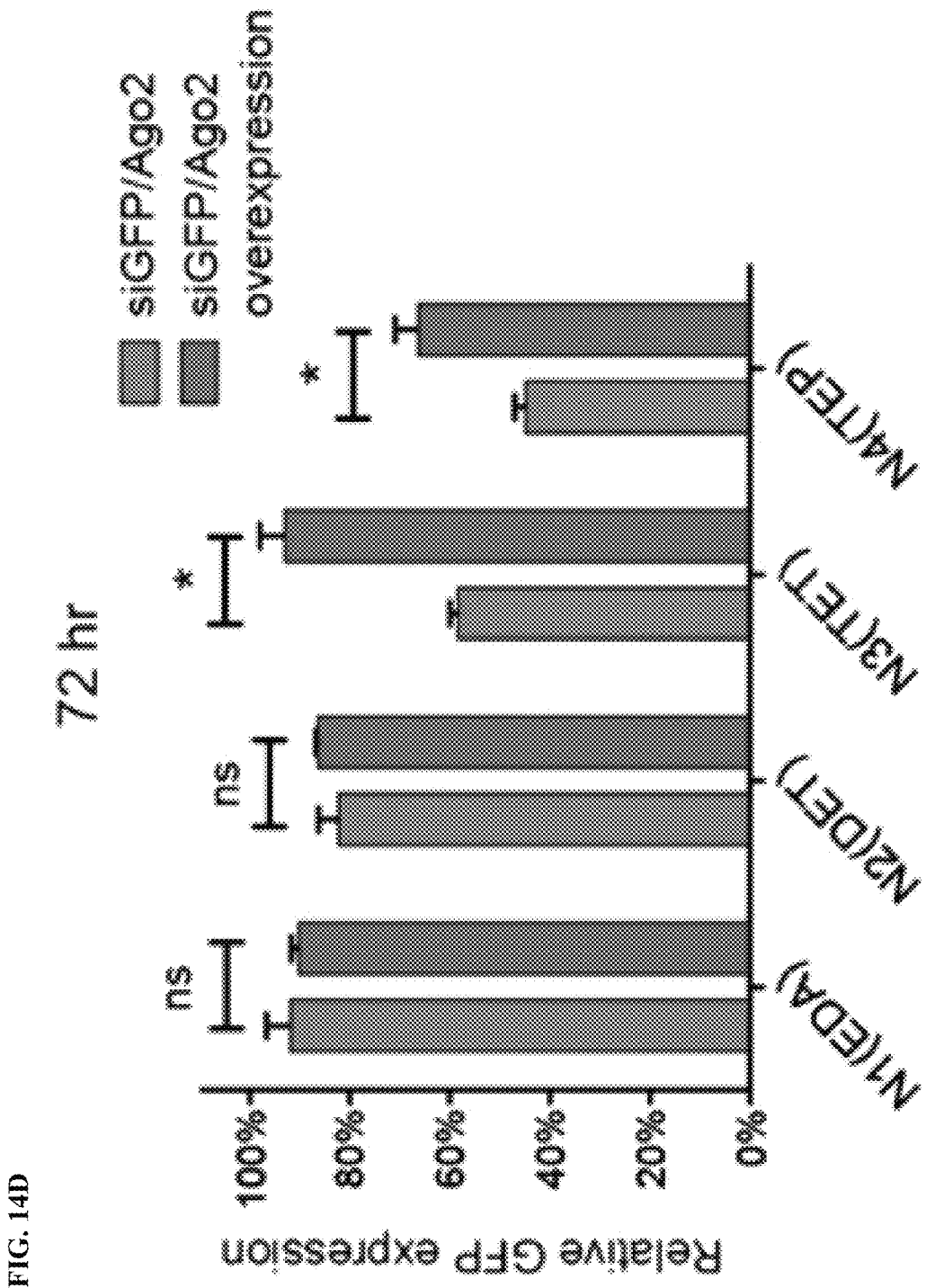
Figure 14E:
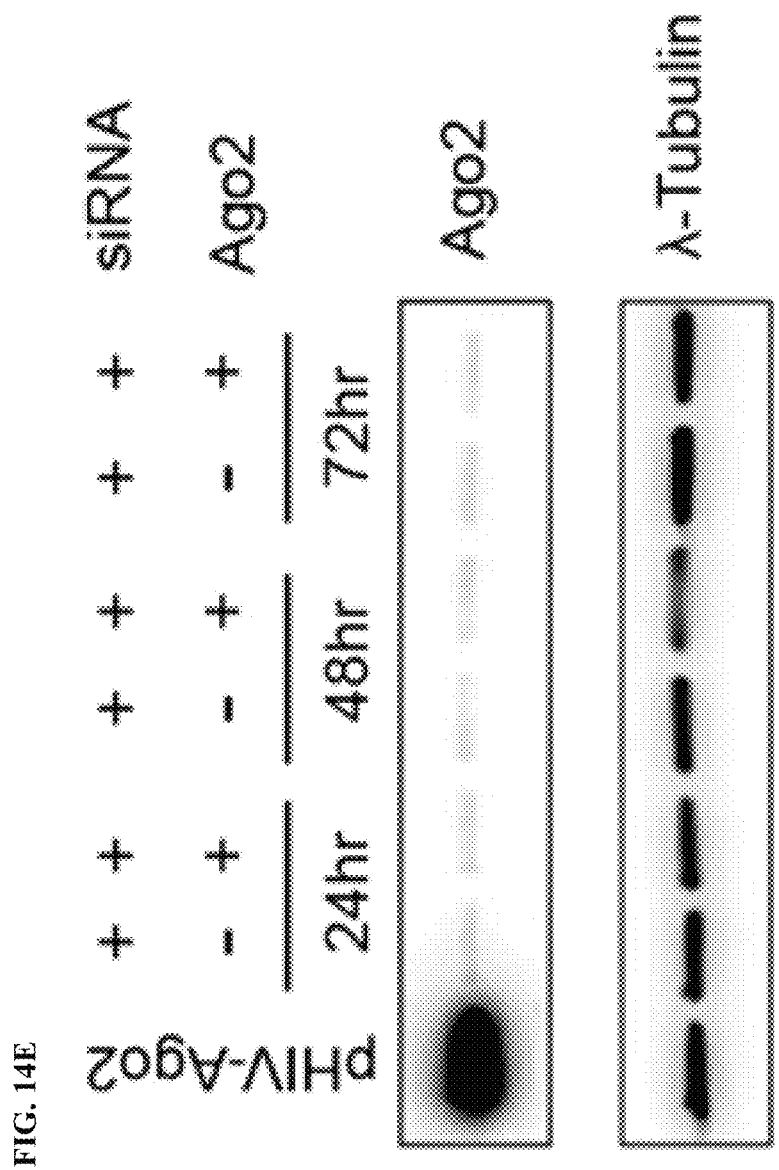

FIG. 14A is a cartoon schematic showing two different siRNA delivery schemes. Physical coassembly of duplex siRNA and Ago2 may promote intracellular formation of RISC comprising ss antisense RNA and Ago2 (Left), whereas transfection of siRNA into cells overexpressing Ago2 does not facilitate loading of siRNA to Ago2 due to potential competition with endogenous miRNA species or RNA degradation (Right). FIGS. 14B-14E are bar graphs (FIGS. 14B-14D) and a photograph (FIG. 14E) collectively depicting that preassembly of the siRNA/Ago2 complex is indispensable for sustained gene silencing. FIG. 14B is a bar graph showing relative GFP expression of experiments where stable overexpression of Ago2 in 293Td2GFP transiently resulted in lower GFP expression 24 h after transfection of 100 nM siGFP, compared with transfection of 100 nM siGFP/Ago2 in 293Td2GFP cells. FIG. 14(C) and FIG. 14D are bar graphs showing relative GFP expression of experiments at 48 h (FIG. 14C) and 72 h (FIG. 14D) after transfection. However, siGFP/Ago2 complexes demonstrated greater GFP silencing than siGFP alone in 293Td2GFP cells overexpressing Ago2 via N3 (TET) and N4 (TEP). Data are represented as the mean±SEM (n=3). *P<0.05, ns, no significance. FIG. 14E is a photograph of a western blot of total Ago2 levels from cells transduced with lentivirus pHIV-Ago2, transfected with siRNA alone or siRNA/Ago2 protein via N4 (TEP) polyamine for different hours (24, 48, and 72 h). While delivery of siRNA/Ago2 protein did not raise Ago2 level relative to siRNA-transfected cells, genetic overexpression substantially increased Ago2 level.

Figure 15A:
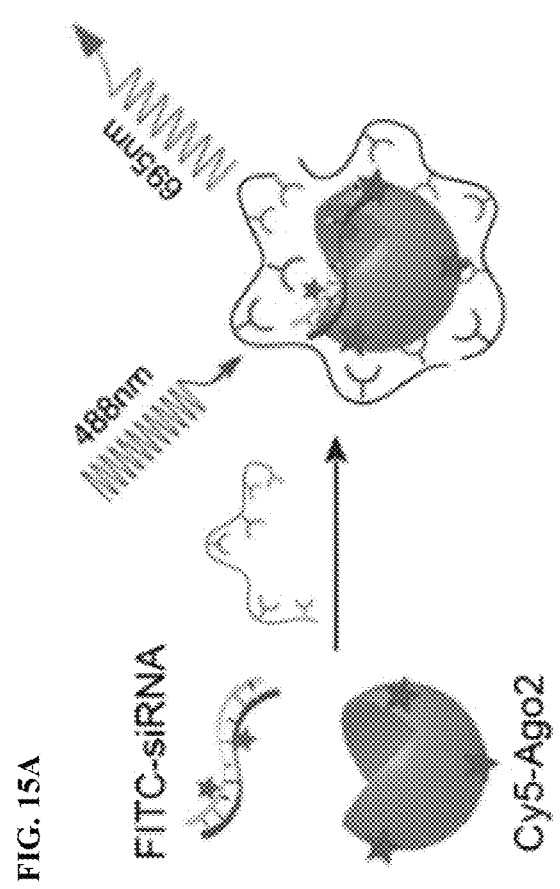
Figure 15B:
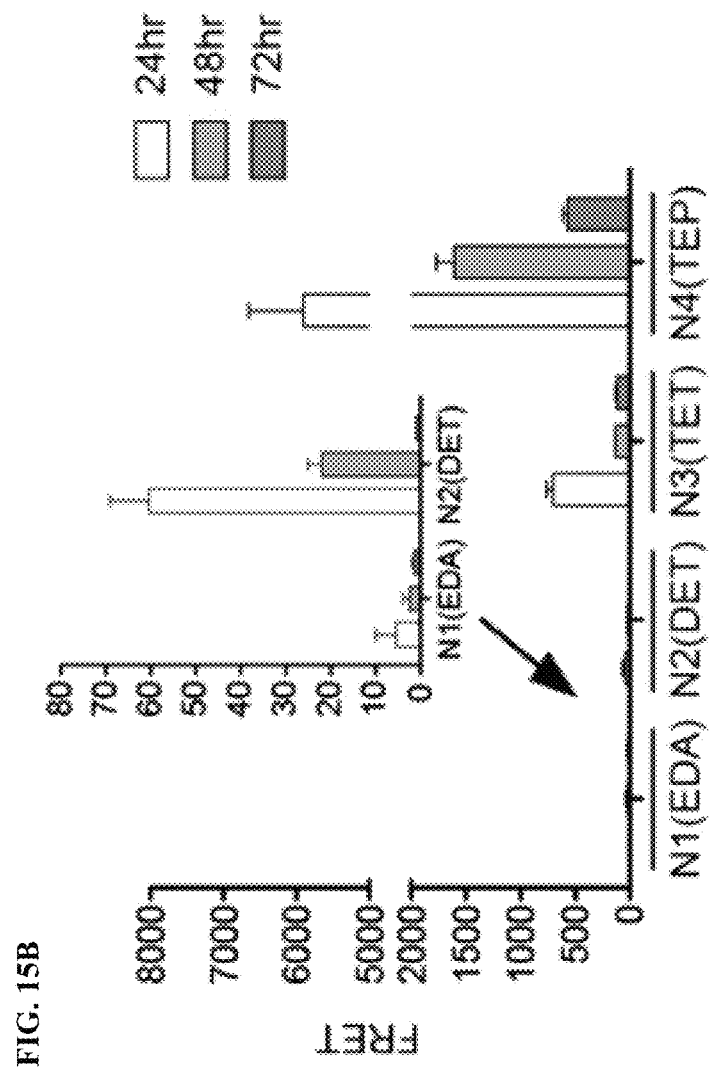
Figure 15C:
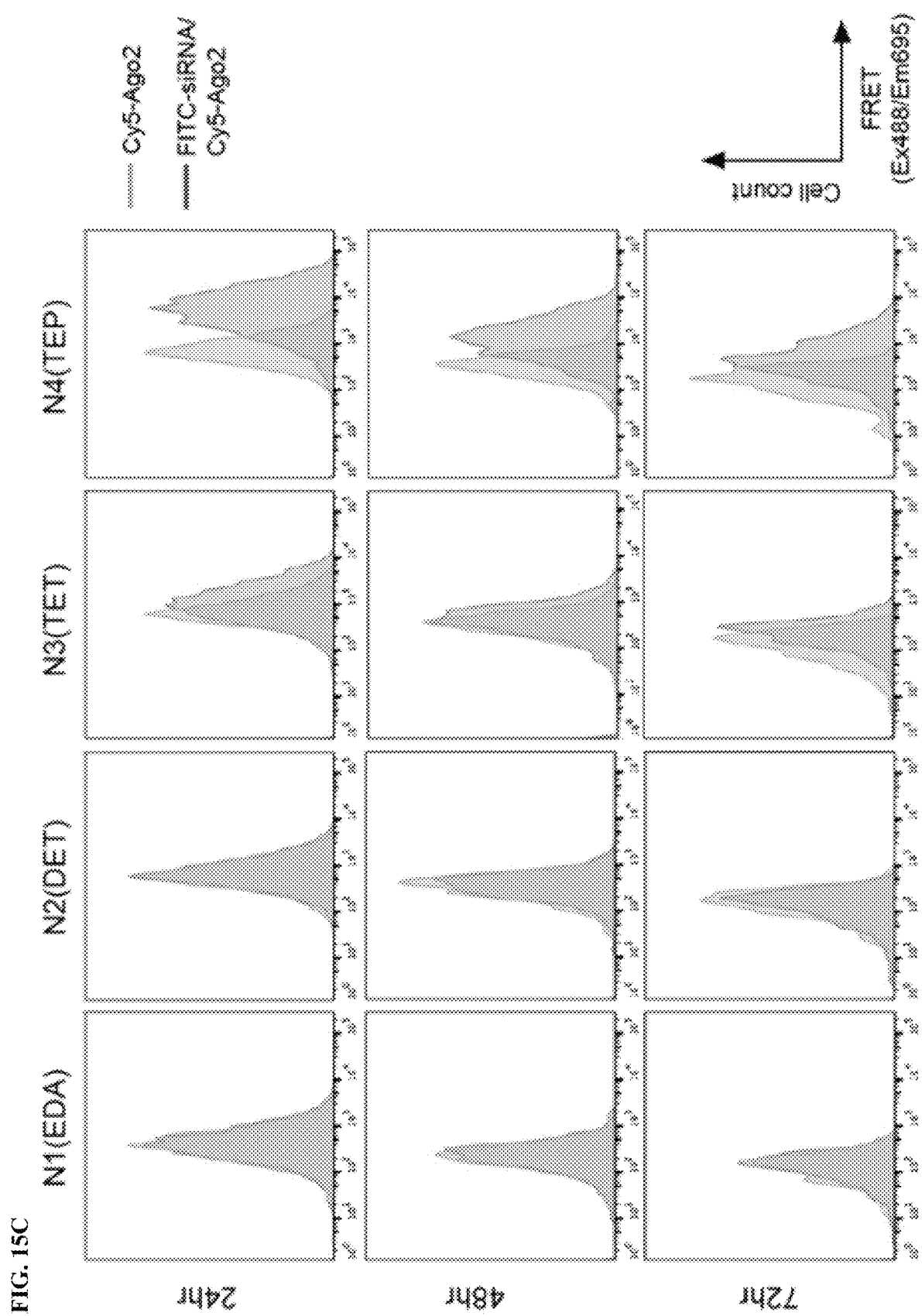

FIG. 15A is a cartoon schematic depicting polyamine-stabilized siRNA/Ago2 complex formation by FRET. FIG. 15B and FIG. 15C are plots collectively depicting that the polyamine side-chain structure stabilizes nanoscale interactions between siRNA and Ago2. FIG. 15A is a graph showing mean FRET intensity in experiments to measure the degree of colocalization between FITC-siRNA and Cy5-Ago2. At 24, 48, and 72 h after transfection of Cy5-Ago2 or FITC-siRNA/Cy5-Ago2 into HEK293T cells with each polyamine, cells were analyzed by flow cytometry with a 488-nm laser and 695-nm detector with a 40-nm bandwidth. FRET values were calculated by subtracting the fluorescence signal of Cy5-Ago2-transfected cells from that of FITC-siRNA/Cy5-Ago2-transfected cells. Data are represented as the mean±SEM (n=3). FIG. 15C are plots showing representative histograms of intracellular FRET assays at 24-, 48-, and 72-h posttransfection.

Figure 16A:
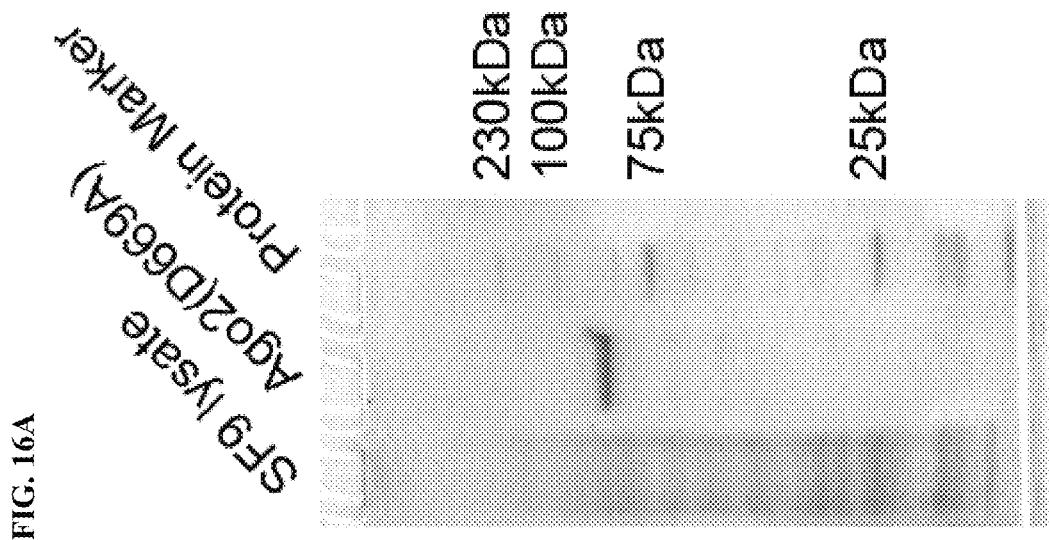
Figure 16B:
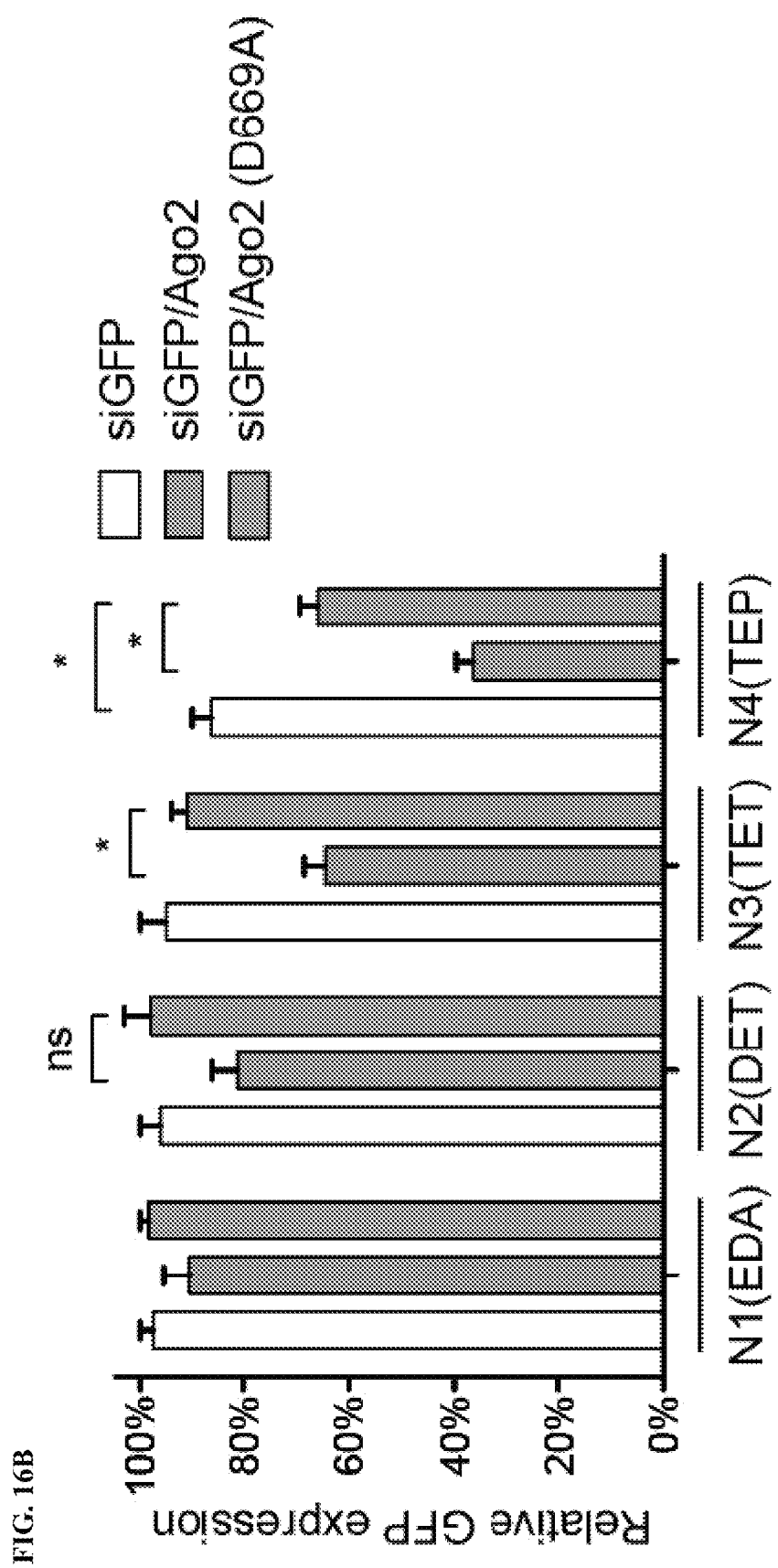

FIG. 16A and FIG. 16B collectively depict the slicing activity of Ago2 is primarily responsible for enhanced silencing via co-delivery of siGFP/Ago2. FIG. 16A is a photograph of a SDS-PAGE of purified recombinant human Ago2 mutant from SF9 insect cells. FIG. 16B is a bar graph of relative GFP expression in experiments where 100 nM siGFP, siGFP/Ago2, or siGFP/Ago2 (D669A) were transfected into 293Td2GFP cells. 48 hours after transfection, mean fluorescence intensity (MFI) of GFP expression was quantified via flow cytometry and normalized to that of scrambled control siRNA-treated cells. Data are represented as the mean±SEM (n=3). *, P<0.05; ns, no significance.

Figure 17A:
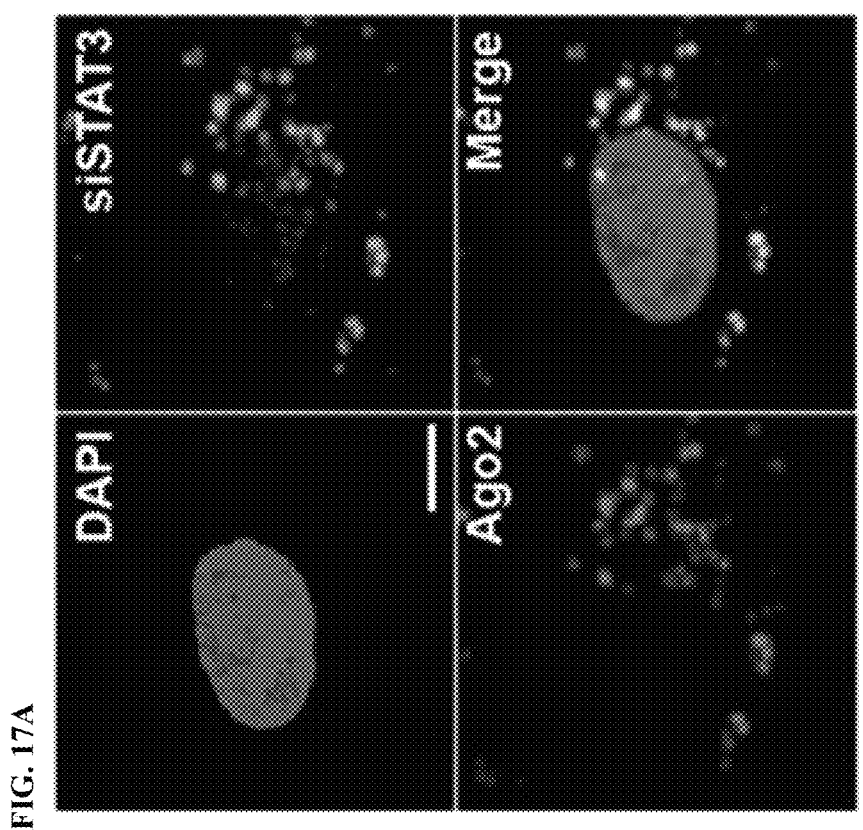
Figure 17B:
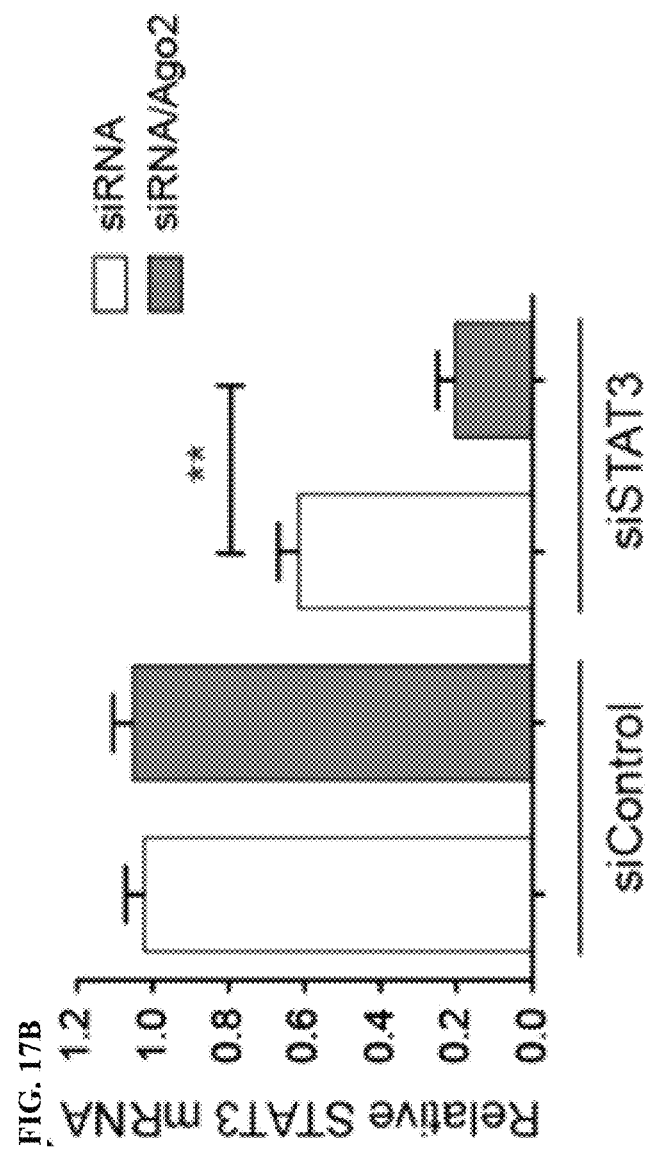
Figure 17C:
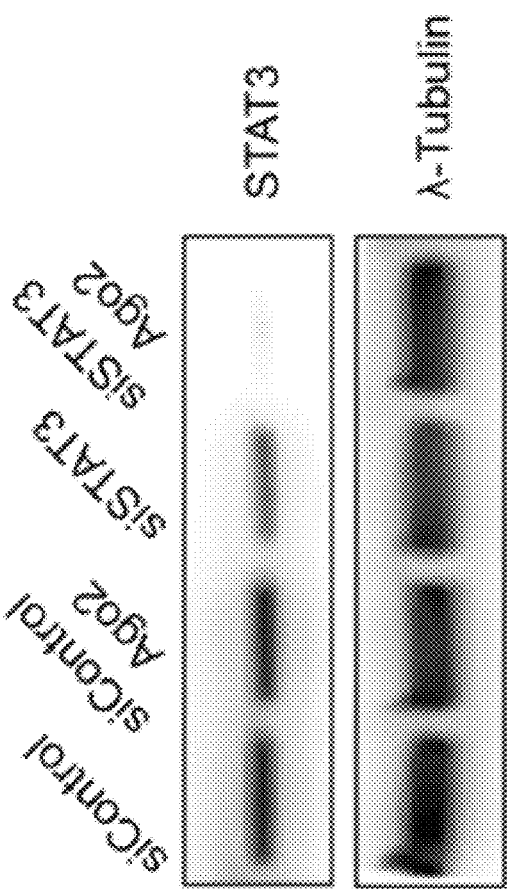
Figure 17D:
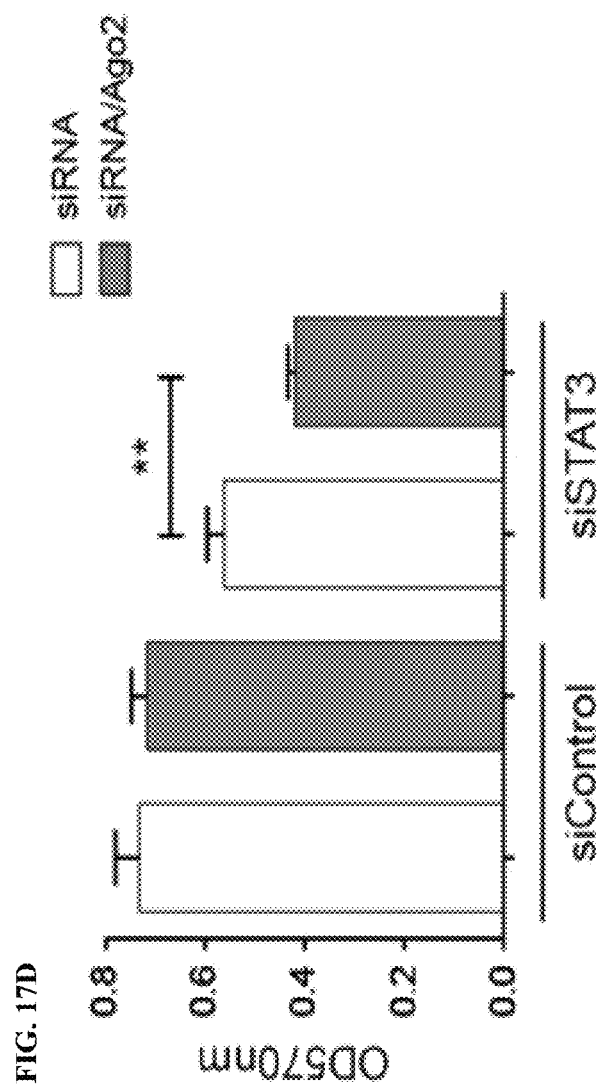

FIG. 17A-17D collectively depict cytosolic delivery of siSTAT3/Ago2 inhibits proliferation of melanoma cells in vitro. FIG. 17A is a photograph showing colocalization of siSTAT3 and Ago2 in B16F10 cells. FITCsiSTAT3 (100 nM)/Cy5-Ago2 (1:1 molar ratio) were transfected into B16F10 cells via N4 (TEP). At 24-h posttransfection, cells were imaged with confocal microscopy. Nuclei were stained with DAPI. (Scale bar: 10 µm). FIG. 17B depicts a bar graph showing the relative STAT3 mRNA from in vitro silencing experiments where B16F10 cells were transfected with 100 nM siRNA/Ago2 or siRNA alone for 48 h. The siSTAT3/Ago2 significantly enhanced gene silencing over siSTAT3 alone detected at the mRNA level. FIG. 17C is a photograph of a Western blot showing the STAT3 protein levels from in vitro silencing experiments where B16F10 cells were transfected with 100 nM siRNA/Ago2 or siRNA alone for 48 h. siControl represents an siRNA with a scrambled sequence. FIG. 17D is a bar graph showing the OD measurements of siSTAT3/Ago2 reduced cell proliferation in comparison with siSTAT3 at 120 h after a single transfection. Cell proliferation was measured by an MTT assay. Data are represented as the mean±SEM (n=3). **P<0.01.

Figure 18:
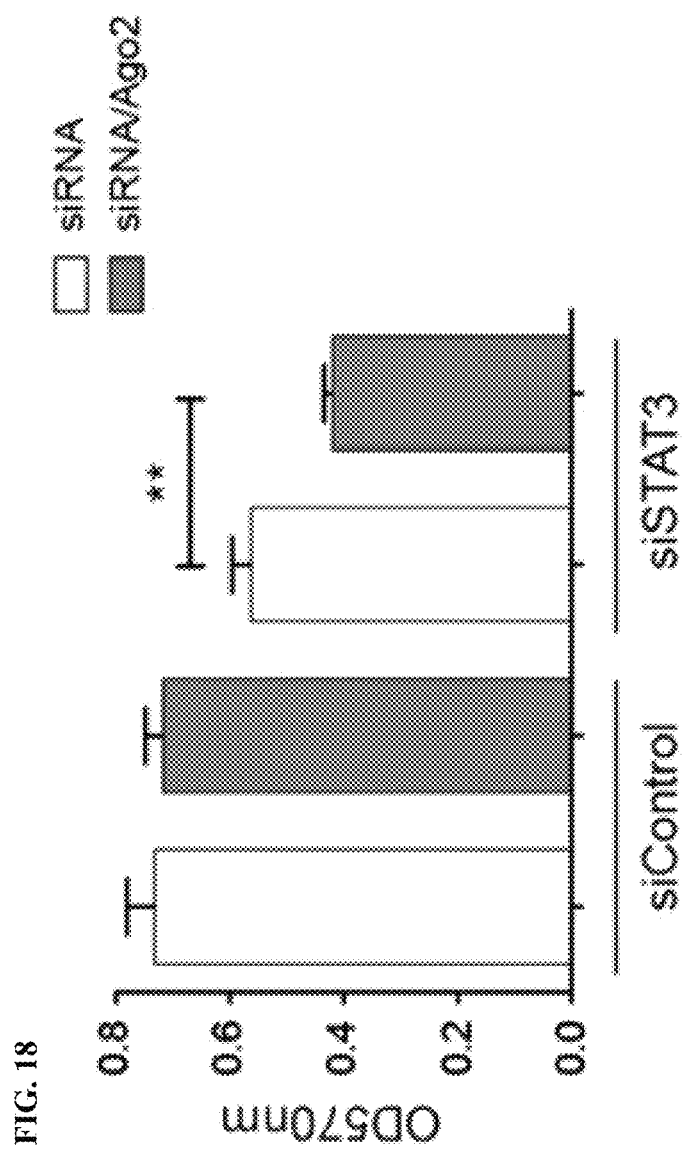

FIG. 18 are photographs showing intracellular fate of transfected Ago2 proteins. 100 nM siSTAT3 and Cy5-labelled Ago2 (1:1 molar ratio) were transfected into B16F10 cells via polyamine-N4 (TEP). At 24 hours post-transfection, cells were imaged with confocal microscopy. Nuclei were stained with DAPI, and a monoclonal antibody, anti-Rab7 was used to locate late endosomes and lysosomes. Scale bar=10 µm.

Figure 19C:
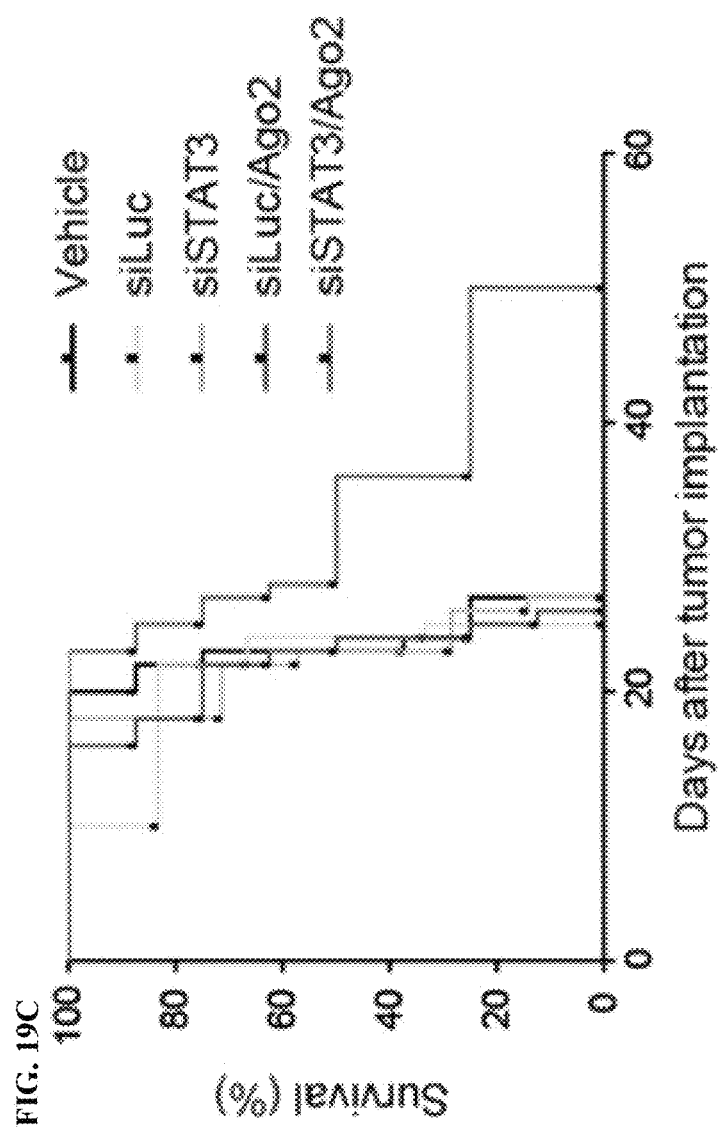
Figure 19D:
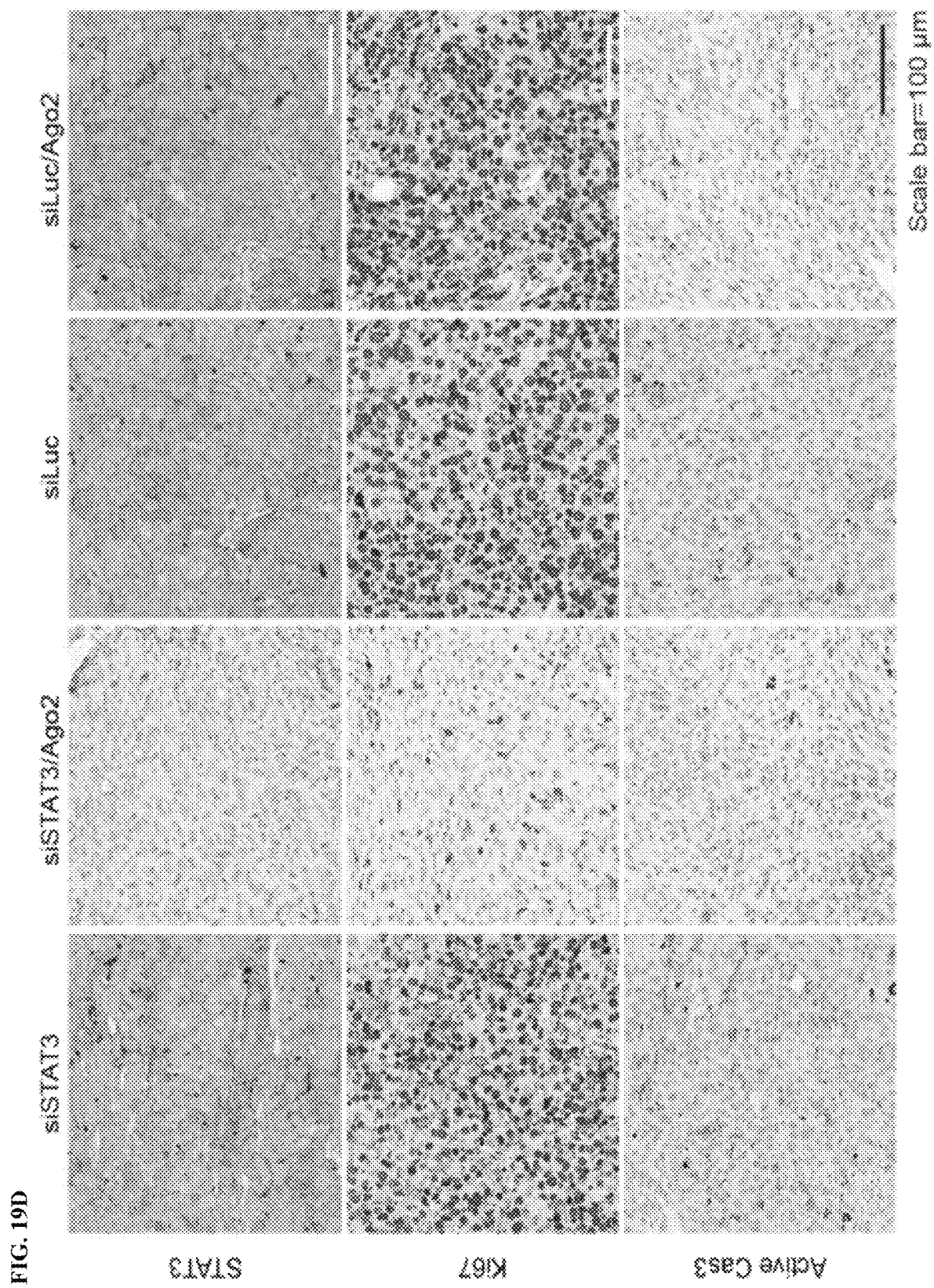

FIG. 19A shows a schedule of tumor inoculation and therapeutic treatment. B16F10 cells (0.5 million) were implanted s.c. in C57BL/6 mice. Mice received intratumoral injections of nanoplexes containing 5 µg siRNA against luciferase (siLuc), siSTAT3, or siRNA with equimolar amounts of Ago2, which were packaged with N4 (TEP) at a 20:1 N/P ratio. FIG. 19B-19D collectively depict therapeutic efficacy of siSTAT3/Ago2 in melanoma model. FIG. 19B is a plot showing tumor size measurements taken every 3 d before each injection on the same day and discontinued when some mice in the control groups were euthanized due to large tumor burden. FIG. 19C shows a graphs of the Kaplan-Meier survival curve for different treatment regimes. siSTAT3/Ago2 significantly extended the survival of B116F10-challenged mice. Vehicle control, siLuc/Ago2, and siSTAT3 (n=7); siLuc (n=6), and siSTAT3/Ago2 (n=8). *P<0.05. FIG. 19D are photographs depicting the expression of STAT3, Ki-67 (cell proliferation marker), and active caspase 3 (apoptotic marker) in tumor samples detected by immunohistological staining 48 h after the last administration of four treatments in a separate study.

DETAILED DESCRIPTION OF THE INVENTION

1. Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

As used herein, the term "administering," refers to the placement of a composition as disclosed herein into a subject by a method or route which results in at least partial localization of the compositions at a desired site.

The term "Ago2" or "Ago-2," unless otherwise specified, refers to Argonaute 2, RISC catalytic component, as well as its isoforms and homologs, including functional equivalents, variants, derivatives, and biologically active fragments thereof. Ago2 is also known in the art as eukaryotic translation initiation factor 2C, Subunit 2 or PAZ Piwi Domain Protein. Other acronyms used for Ago2 may include, AG02; ago; AGO 2; ago-2; Ago-2; ago2; Ago2; CG13452; CG7439; dAgo2; dAGO2; Dm Ago2; DmAgo2; Dmel\CG7439; eIF2C2. The Ago2 gene encodes a member of the Argonaute family of proteins which play a role in RNA interference. The encoded protein is highly basic, and contains a PAZ domain and a PIWI domain. Multiple transcript variants encoding different isoforms have been found for this gene. Ago2 is a core RISC component that has both mRNA inhibition and degradation functions (O'Carroll et al. *Genes Dev.* 21: 1999-2004, 2007). Ago2 may be required for RNA-mediated gene silencing (RNAi) by the RNA-induced silencing complex (RISC). The minimal RISC appears to include AGO2 bound to a short guide RNA such as a microRNA (miRNA) or short interfering RNA (siRNA). These guide RNAs direct RISC to complementary mRNAs that are targets for RISC-mediated gene silencing. The precise mechanism of gene silencing depends on the degree of complementarity between the miRNA or siRNA and its target. Binding of RISC to a perfectly complementary mRNA generally results in silencing due to endonucleolytic cleavage of the mRNA specifically by AGO2. Binding of RISC to a partially complementary mRNA results in silencing through inhibition of translation, and this is independent of endonuclease activity. Ago2 may inhibit translation initiation by binding to the 7-methylguanosine cap, thereby preventing the recruitment of the translation initiation factor eIF4-E. Ago2 may also inhibit translation initiation via interaction with EIF6, which itself binds to the 60S ribosomal subunit and prevents its association with the 40S ribosomal subunit. The inhibition of translational initiation leads to the accumulation of the affected mRNA in cytoplasmic processing bodies (P-bodies), where mRNA degradation may subsequently occur. In some cases, RISC-mediated translational repression is also observed for miRNAs that perfectly match the 3 untranslated region (3-UTR). Ago2 can also up-regulate the translation of specific mRNAs under certain growth conditions. Ago2 may bind to the AU element of the 3-UTR of the TNF (TNF-α) mRNA and up-regulates translation under conditions of serum starvation. Ago2 may also be required for transcriptional gene silencing (TGS), in which short RNAs known as antigene RNAs or agRNAs direct the transcriptional repression of complementary promoter regions. (Martinez J. et al. *Genes Dev.* 18:975-980 (2004); Meister G. et al. *Mol. Cell* 15:185-197 (2004); Pillai R. S. et al. *RNA* 10:1518-1525 (2004); Liu J. et al. *Science* 305:1437-1441 (2004); Gregory R. I. et al. *Cell* 123:631-640 (2005); Meister G. et al. *Curr. Biol.* 15:2149-2155 (2005); Haase A. D. et al. *EMBO Rep.* 6:961-967 (2005); Maniataki E. et al. *Genes Dev.* 19:2979-2990 (2005); Rivas F. V. et al. *Nat. Struct. Mol. Biol.* 12:340-349 (2005); Pillai R. S. et al. *Science* 309:1573-1576 (2005); Janowski B. A. et al. *Nat. Struct. Mol. Biol.* 13:787-792 (2006); Chu C.-Y. et al. *PLoS Biol.* 4:E210-E210 (2006); Vasudevan S. et al. *Cell* 128:1105-1118 (2007); Kiriakidou M. et al. *Cell* 129:1141-1151 (2007); Hoeck J. et al. *EMBO Rep.* 8:1052-1060 (2007); Robb G. B. et al. *Mol. Cell* 26:523-537 (2007); Chendrimada T. P. et al. *Nature* 447:823-828 (2007); Vasudevan S. et al. *Science* 318:1931-1934 (2007); Wu L. et al. *Curr. Biol.* 18:1327-1332 (2008); Qi H. H. et al. *Nature* 455:421-424 (2008); MacRae I. J. et al. *Proc. Natl. Acad. Sci. U.S.A.* 105:512-517 (2008); Weinmann L. et al. *Cell* 136:496-507 (2009); Faehnle C. R. et al. *Cell Rep.* 3:1901-1909 (2013))

In certain embodiments, the Ago2 comprises the polypeptide sequence having the amino acid sequences set forth in SEQ ID NO: 1, 2, or 3.

```
Human Ago2 (recombinant sequence)
                                                               (SEQ ID NO: 1)
Gly Ala Met Tyr Ser Gly Ala Gly Pro Ala Leu Ala Pro Pro Ala Pro
1               5                   10                  15

Pro Pro Pro Ile Gln Gly Tyr Ala Phe Lys Pro Pro Arg Pro Asp
            20                  25                  30

Phe Gly Thr Ser Gly Arg Thr Ile Lys Leu Gln Ala Asn Phe Phe Glu
            35                  40                  45

Met Asp Ile Pro Lys Ile Asp Ile Tyr His Tyr Glu Leu Asp Ile Lys
    50                  55                  60

Pro Glu Lys Cys Pro Arg Arg Val Asn Arg Glu Ile Val Glu His Met
65                  70                  75                  80

Val Gln His Phe Lys Thr Gln Ile Phe Gly Asp Arg Lys Pro Val Phe
                85                  90                  95

Asp Gly Arg Lys Asn Leu Tyr Thr Ala Met Pro Leu Pro Ile Gly Arg
                100                 105                 110

Asp Lys Val Glu Leu Glu Val Thr Leu Pro Gly Glu Gly Lys Asp Arg
            115                 120                 125

Ile Phe Lys Val Ser Ile Lys Trp Val Ser Cys Val Ser Leu Gln Ala
            130                 135                 140

Leu His Asp Ala Leu Ser Gly Arg Leu Pro Ser Val Pro Phe Glu Thr
145                 150                 155                 160

Ile Gln Ala Leu Asp Val Val Met Arg His Leu Pro Ser Met Arg Tyr
                165                 170                 175
```

-continued

```
Thr Pro Val Gly Arg Ser Phe Phe Thr Ala Ser Glu Gly Cys Ser Asn
            180                 185                 190

Pro Leu Gly Gly Arg Glu Val Trp Phe Gly Phe His Gln Ser Val
        195                 200                 205

Arg Pro Ser Leu Trp Lys Met Met Leu Asn Ile Asp Val Ser Ala Thr
    210                 215                 220

Ala Phe Tyr Lys Ala Gln Pro Val Ile Glu Phe Val Cys Glu Val Leu
225                 230                 235                 240

Asp Phe Lys Ser Ile Glu Glu Gln Lys Pro Leu Thr Asp Ser Gln
                245                 250                 255

Arg Val Lys Phe Thr Lys Glu Ile Lys Gly Leu Lys Val Glu Ile Thr
                260                 265                 270

His Cys Gly Gln Met Lys Arg Lys Tyr Arg Val Cys Asn Val Thr Arg
                275                 280                 285

Arg Pro Ala Ser His Gln Thr Phe Pro Leu Gln Gln Glu Ser Gly Gln
        290                 295                 300

Thr Val Glu Cys Thr Val Ala Gln Tyr Phe Lys Asp Arg His Lys Leu
305                 310                 315                 320

Val Leu Arg Tyr Pro His Leu Pro Cys Leu Gln Val Gly Gln Glu Gln
                325                 330                 335

Lys His Thr Tyr Leu Pro Leu Glu Val Cys Asn Ile Val Ala Gly Gln
                340                 345                 350

Arg Cys Ile Lys Lys Leu Thr Asp Asn Gln Thr Ser Thr Met Ile Arg
        355                 360                 365

Ala Thr Ala Arg Ser Ala Pro Asp Arg Gln Glu Glu Ile Ser Lys Leu
    370                 375                 380

Met Arg Ser Ala Ser Phe Asn Thr Asp Pro Tyr Val Arg Glu Phe Gly
385                 390                 395                 400

Ile Met Val Lys Asp Glu Met Thr Asp Val Thr Gly Arg Val Leu Gln
                405                 410                 415

Pro Pro Ser Ile Leu Tyr Gly Gly Arg Asn Lys Ala Ile Ala Thr Pro
                420                 425                 430

Val Gln Gly Val Trp Asp Met Arg Asn Lys Gln Phe His Thr Gly Ile
        435                 440                 445

Glu Ile Lys Val Trp Ala Ile Ala Cys Phe Ala Pro Gln Arg Gln Cys
    450                 455                 460

Thr Glu Val His Leu Lys Ser Phe Thr Glu Gln Leu Arg Lys Ile Ser
465                 470                 475                 480

Arg Asp Ala Gly Met Pro Ile Gln Gly Gln Pro Cys Phe Cys Lys Tyr
                485                 490                 495

Ala Gln Gly Ala Asp Ser Val Glu Pro Met Phe Arg His Leu Lys Asn
                500                 505                 510

Thr Tyr Ala Gly Leu Gln Leu Val Val Ile Leu Pro Gly Lys Thr
        515                 520                 525

Pro Val Tyr Ala Glu Val Lys Arg Val Gly Asp Thr Val Leu Gly Met
    530                 535                 540

Ala Thr Gln Cys Val Gln Met Lys Asn Val Gln Arg Thr Thr Pro Gln
545                 550                 555                 560

Thr Leu Ser Asn Leu Cys Leu Lys Ile Asn Val Lys Leu Gly Gly Val
                565                 570                 575

Asn Asn Ile Leu Leu Pro Gln Gly Arg Pro Pro Val Phe Gln Gln Pro
                580                 585                 590

Val Ile Phe Leu Gly Ala Asp Val Thr His Pro Pro Ala Gly Asp Gly
                595                 600                 605
```

-continued

```
Lys Lys Pro Ser Ile Ala Ala Val Val Gly Ser Met Asp Ala His Pro
            610             615                 620

Asn Arg Tyr Cys Ala Thr Val Arg Val Gln Gln His Arg Gln Glu Ile
625                 630                 635                 640

Ile Gln Asp Leu Ala Ala Met Val Arg Glu Leu Leu Ile Gln Phe Tyr
                645                 650                 655

Lys Ser Thr Arg Phe Lys Pro Thr Arg Ile Ile Phe Tyr Arg Asp Gly
            660                 665                 670

Val Ser Glu Gly Gln Phe Gln Gln Val Leu His His Glu Leu Leu Ala
            675                 680                 685

Ile Arg Glu Ala Cys Ile Lys Leu Glu Lys Asp Tyr Gln Pro Gly Ile
            690                 695                 700

Thr Phe Ile Val Val Gln Lys Arg His His Thr Arg Leu Phe Cys Thr
705                 710                 715                 720

Asp Lys Asn Glu Arg Val Gly Lys Ser Gly Asn Ile Pro Ala Gly Thr
                725                 730                 735

Thr Val Asp Thr Lys Ile Thr His Pro Thr Glu Phe Asp Phe Tyr Leu
                740                 745                 750

Cys Ser His Ala Gly Ile Gln Gly Thr Ser Arg Pro Ser His Tyr His
            755                 760                 765

Val Leu Trp Asp Asp Asn Arg Phe Ser Ser Asp Glu Leu Gln Ile Leu
            770                 775                 780

Thr Tyr Gln Leu Cys His Thr Tyr Val Arg Cys Thr Arg Ser Val Ser
785                 790                 795                 800

Ile Pro Ala Pro Ala Tyr Tyr Ala His Leu Val Ala Phe Arg Ala Arg
                805                 810                 815

Tyr His Leu Val Asp Lys Glu His Asp Ser Ala Glu Gly Ser His Thr
            820                 825                 830

Ser Gly Gln Ser Asn Gly Arg Asp His Gln Ala Leu Ala Lys Ala Val
            835                 840                 845

Gln Val His Gln Asp Thr Leu Arg Thr Met Tyr Phe Ala
            850                 855                 860

Human Ago2 (UniprotKB Q9UKV8-1 isoform 1 (accession numbers Q8TCZ5, Q8WV58,
Q96ID1)
                                                              (SEQ ID NO: 2)
Met Tyr Ser Gly Ala Gly Pro Ala Leu Ala Pro Pro Ala Pro Pro Pro
1               5                   10                  15

Pro Ile Gln Gly Tyr Ala Phe Lys Pro Pro Pro Arg Pro Asp Phe Gly
                20                  25                  30

Thr Ser Gly Arg Thr Ile Lys Leu Gln Ala Asn Phe Phe Glu Met Asp
            35                  40                  45

Ile Pro Lys Ile Asp Ile Tyr His Tyr Glu Leu Asp Ile Lys Pro Glu
50                  55                  60

Lys Cys Pro Arg Arg Val Asn Arg Glu Ile Val Glu His Met Val Gln
65              70                  75                  80

His Phe Lys Thr Gln Ile Phe Gly Asp Arg Lys Pro Val Phe Asp Gly
            85                  90                  95

Arg Lys Asn Leu Tyr Thr Ala Met Pro Leu Pro Ile Gly Arg Asp Lys
            100                 105                 110

Val Glu Leu Glu Val Thr Leu Pro Gly Glu Gly Lys Asp Arg Ile Phe
            115                 120                 125

Lys Val Ser Ile Lys Trp Val Ser Cys Val Ser Leu Gln Ala Leu His
            130                 135                 140

Asp Ala Leu Ser Gly Arg Leu Pro Ser Val Pro Phe Glu Thr Ile Gln
145                 150                 155                 160
```

-continued

```
Ala Leu Asp Val Val Met Arg His Leu Pro Ser Met Arg Tyr Thr Pro
            165                 170                 175
Val Gly Arg Ser Phe Phe Thr Ala Ser Glu Gly Cys Ser Asn Pro Leu
            180                 185                 190
Gly Gly Gly Arg Glu Val Trp Phe Gly Phe His Gln Ser Val Arg Pro
            195                 200                 205
Ser Leu Trp Lys Met Met Leu Asn Ile Asp Val Ser Ala Thr Ala Phe
        210                 215                 220
Tyr Lys Ala Gln Pro Val Ile Glu Phe Val Cys Glu Val Leu Asp Phe
225                 230                 235                 240
Lys Ser Ile Glu Glu Gln Gln Lys Pro Leu Thr Asp Ser Gln Arg Val
            245                 250                 255
Lys Phe Thr Lys Glu Ile Lys Gly Leu Lys Val Glu Ile Thr His Cys
            260                 265                 270
Gly Gln Met Lys Arg Lys Tyr Arg Val Cys Asn Val Thr Arg Arg Pro
            275                 280                 285
Ala Ser His Gln Thr Phe Pro Leu Gln Gln Glu Ser Gly Gln Thr Val
            290                 295                 300
Glu Cys Thr Val Ala Gln Tyr Phe Lys Asp Arg His Lys Leu Val Leu
305                 310                 315                 320
Arg Tyr Pro His Leu Pro Cys Leu Gln Val Gly Gln Glu Gln Lys His
            325                 330                 335
Thr Tyr Leu Pro Leu Glu Val Cys Asn Ile Val Ala Gly Gln Arg Cys
            340                 345                 350
Ile Lys Lys Leu Thr Asp Asn Gln Thr Ser Thr Met Ile Arg Ala Thr
            355                 360                 365
Ala Arg Ser Ala Pro Asp Arg Gln Glu Glu Ile Ser Lys Leu Met Arg
            370                 375                 380
Ser Ala Ser Phe Asn Thr Asp Pro Tyr Val Arg Glu Phe Gly Ile Met
385                 390                 395                 400
Val Lys Asp Glu Met Thr Asp Val Thr Gly Arg Val Leu Gln Pro Pro
            405                 410                 415
Ser Ile Leu Tyr Gly Gly Arg Asn Lys Ala Ile Ala Thr Pro Val Gln
            420                 425                 430
Gly Val Trp Asp Met Arg Asn Lys Gln Phe His Thr Gly Ile Glu Ile
            435                 440                 445
Lys Val Trp Ala Ile Ala Cys Phe Ala Pro Gln Arg Gln Cys Thr Glu
            450                 455                 460
Val His Leu Lys Ser Phe Thr Glu Gln Leu Arg Lys Ile Ser Arg Asp
465                 470                 475                 480
Ala Gly Met Pro Ile Gln Gly Gln Pro Cys Phe Cys Lys Tyr Ala Gln
            485                 490                 495
Gly Ala Asp Ser Val Glu Pro Met Phe Arg His Leu Lys Asn Thr Tyr
            500                 505                 510
Ala Gly Leu Gln Leu Val Val Ile Leu Pro Gly Lys Thr Pro Val
            515                 520                 525
Tyr Ala Glu Val Lys Arg Val Gly Asp Thr Val Leu Gly Met Ala Thr
            530                 535                 540
Gln Cys Val Gln Met Lys Asn Val Gln Arg Thr Thr Pro Gln Thr Leu
545                 550                 555                 560
Ser Asn Leu Cys Leu Lys Ile Asn Val Lys Leu Gly Gly Val Asn Asn
            565                 570                 575
Ile Leu Leu Pro Gln Gly Arg Pro Pro Val Phe Gln Gln Pro Val Ile
            580                 585                 590
```

-continued

```
Phe Leu Gly Ala Asp Val Thr His Pro Pro Ala Gly Asp Gly Lys Lys
            595                 600                 605

Pro Ser Ile Ala Ala Val Val Gly Ser Met Asp Ala His Pro Asn Arg
            610                 615                 620

Tyr Cys Ala Thr Val Arg Val Gln Gln His Arg Gln Glu Ile Ile Gln
625                 630                 635                 640

Asp Leu Ala Ala Met Val Arg Glu Leu Leu Ile Gln Phe Tyr Lys Ser
                645                 650                 655

Thr Arg Phe Lys Pro Thr Arg Ile Ile Phe Tyr Arg Asp Gly Val Ser
                660                 665                 670

Glu Gly Gln Phe Gln Gln Val Leu His His Glu Leu Leu Ala Ile Arg
                675                 680                 685

Glu Ala Cys Ile Lys Leu Glu Lys Asp Tyr Gln Pro Gly Ile Thr Phe
            690                 695                 700

Ile Val Val Gln Lys Arg His His Thr Arg Leu Phe Cys Thr Asp Lys
705                 710                 715                 720

Asn Glu Arg Val Gly Lys Ser Gly Asn Ile Pro Ala Gly Thr Thr Val
                725                 730                 735

Asp Thr Lys Ile Thr His Pro Thr Glu Phe Asp Phe Tyr Leu Cys Ser
                740                 745                 750

His Ala Gly Ile Gln Gly Thr Ser Arg Pro Ser His Tyr His Val Leu
            755                 760                 765

Trp Asp Asp Asn Arg Phe Ser Ser Asp Glu Leu Gln Ile Leu Thr Tyr
770                 775                 780

Gln Leu Cys His Thr Tyr Val Arg Cys Thr Arg Ser Val Ser Ile Pro
785                 790                 795                 800

Ala Pro Ala Tyr Tyr Ala His Leu Val Ala Phe Arg Ala Arg Tyr His
                805                 810                 815

Leu Val Asp Lys Glu His Asp Ser Ala Glu Gly Ser His Thr Ser Gly
                820                 825                 830

Gln Ser Asn Gly Arg Asp His Gln Ala Leu Ala Lys Ala Val Gln Val
            835                 840                 845

His Gln Asp Thr Leu Arg Thr Met Tyr Phe Ala
            850                 855

Human Ago2 (UniprotKB Q9UKV8-2 isoform 2)                    (SEQ ID NO: 3)

Met Tyr Ser Gly Ala Gly Pro Ala Leu Ala Pro Ala Pro Pro Pro Pro
1               5                   10                  15

Pro Ile Gln Gly Tyr Ala Phe Lys Pro Pro Pro Arg Pro Asp Phe Gly
                20                  25                  30

Thr Ser Gly Arg Thr Ile Lys Leu Gln Ala Asn Phe Phe Glu Met Asp
            35                  40                  45

Ile Pro Lys Ile Asp Ile Tyr His Tyr Glu Leu Asp Ile Lys Pro Glu
        50                  55                  60

Lys Cys Pro Arg Arg Val Asn Arg Glu Ile Val Glu His Met Val Gln
65                  70                  75                  80

His Phe Lys Thr Gln Ile Phe Gly Asp Arg Lys Pro Val Phe Asp Gly
                85                  90                  95

Arg Lys Asn Leu Tyr Thr Ala Met Pro Leu Pro Ile Gly Arg Asp Lys
            100                 105                 110

Val Glu Leu Glu Val Thr Leu Pro Gly Glu Gly Lys Asp Arg Ile Phe
            115                 120                 125

Lys Val Ser Ile Lys Trp Val Ser Cys Val Ser Leu Gln Ala Leu His
        130                 135                 140
```

```
Asp Ala Leu Ser Gly Arg Leu Pro Ser Val Pro Phe Glu Thr Ile Gln
145                 150                 155                 160

Ala Leu Asp Val Val Met Arg His Leu Pro Ser Met Arg Tyr Thr Pro
                165                 170                 175

Val Gly Arg Ser Phe Phe Thr Ala Ser Glu Gly Cys Ser Asn Pro Leu
            180                 185                 190

Gly Gly Gly Arg Glu Val Trp Phe Gly Phe His Gln Ser Val Arg Pro
        195                 200                 205

Ser Leu Trp Lys Met Met Leu Asn Ile Asp Val Ser Ala Thr Ala Phe
    210                 215                 220

Tyr Lys Ala Gln Pro Val Ile Glu Phe Val Cys Glu Val Leu Asp Phe
225                 230                 235                 240

Lys Ser Ile Glu Glu Gln Gln Lys Pro Leu Thr Asp Ser Gln Arg Val
                245                 250                 255

Lys Phe Thr Lys Glu Ile Lys Gly Leu Lys Val Glu Ile Thr His Cys
            260                 265                 270

Gly Gln Met Lys Arg Lys Tyr Arg Val Cys Asn Val Thr Arg Arg Pro
        275                 280                 285

Ala Ser His Gln Thr Phe Pro Leu Gln Gln Glu Ser Gly Gln Thr Val
    290                 295                 300

Glu Cys Thr Val Ala Gln Tyr Phe Lys Asp Arg His Lys Leu Val Leu
305                 310                 315                 320

Arg Tyr Pro His Leu Pro Cys Leu Gln Val Gly Gln Glu Gln Lys His
                325                 330                 335

Thr Tyr Leu Pro Leu Glu Val Cys Asn Ile Val Ala Gly Gln Arg Cys
            340                 345                 350

Ile Lys Lys Leu Thr Asp Asn Gln Thr Ser Thr Met Ile Arg Ala Thr
        355                 360                 365

Ala Arg Ser Ala Pro Asp Arg Gln Glu Glu Ile Ser Lys Leu Met Arg
    370                 375                 380

Ser Ala Ser Phe Asn Thr Asp Pro Tyr Val Arg Glu Phe Gly Ile Met
385                 390                 395                 400

Val Lys Asp Glu Met Thr Asp Val Thr Gly Arg Val Leu Gln Pro Pro
                405                 410                 415

Ser Ile Leu Tyr Gly Gly Arg Asn Lys Ala Ile Ala Thr Pro Val Gln
            420                 425                 430

Gly Val Trp Asp Met Arg Asn Lys Gln Phe His Thr Gly Ile Glu Ile
        435                 440                 445

Lys Val Trp Ala Ile Ala Cys Phe Ala Pro Gln Arg Gln Cys Thr Glu
    450                 455                 460

Val His Leu Lys Ser Phe Thr Glu Gln Leu Arg Lys Ile Ser Arg Asp
465                 470                 475                 480

Ala Gly Met Pro Ile Gln Gly Gln Pro Cys Phe Cys Lys Tyr Ala Gln
                485                 490                 495

Gly Ala Asp Ser Val Glu Pro Met Phe Arg His Leu Lys Asn Thr Tyr
            500                 505                 510

Ala Gly Leu Gln Leu Val Val Ile Leu Pro Gly Lys Thr Pro Val
        515                 520                 525

Tyr Ala Glu Val Lys Arg Val Gly Asp Thr Val Leu Gly Met Ala Thr
    530                 535                 540

Gln Cys Val Gln Met Lys Asn Val Gln Arg Thr Thr Pro Gln Thr Leu
545                 550                 555                 560

Ser Asn Leu Cys Leu Lys Ile Asn Val Lys Leu Gly Gly Val Asn Asn
                565                 570                 575
```

-continued

```
Ile Leu Leu Pro Gln Gly Arg Pro Pro Val Phe Gln Gln Pro Val Ile
            580                 585                 590
Phe Leu Gly Ala Asp Val Thr His Pro Pro Ala Gly Asp Gly Lys Lys
            595                 600                 605
Pro Ser Ile Ala Ala Val Val Gly Ser Met Asp Ala His Pro Asn Arg
            610                 615                 620
Tyr Cys Ala Thr Val Arg Val Gln Gln His Arg Gln Glu Ile Ile Gln
625                     630                 635                 640
Asp Leu Ala Ala Met Val Arg Glu Leu Leu Ile Gln Phe Tyr Lys Ser
                645                 650                 655
Thr Arg Phe Lys Pro Thr Arg Ile Ile Phe Tyr Arg Asp Gly Val Ser
            660                 665                 670
Glu Gly Gln Phe Gln Gln Val Leu His His Glu Leu Leu Ala Ile Arg
            675                 680                 685
Glu Ala Cys Ile Lys Leu Glu Lys Asp Tyr Gln Pro Gly Ile Thr Phe
            690                 695                 700
Ile Val Val Gln Lys Arg His His Thr Arg Leu Phe Cys Thr Asp Lys
705                     710                 715                 720
Asn Glu Arg Gly Thr Ser Arg Pro Ser His Tyr His Val Leu Trp Asp
                725                 730                 735
Asp Asn Arg Phe Ser Ser Asp Glu Leu Gln Ile Leu Thr Tyr Gln Leu
            740                 745                 750
Cys His Thr Tyr Val Arg Cys Thr Arg Ser Val Ser Ile Pro Ala Pro
            755                 760                 765
Ala Tyr Tyr Ala His Leu Val Ala Phe Arg Ala Arg Tyr His Leu Val
            770                 775                 780
Asp Lys Glu His Asp Ser Ala Glu Gly Ser His Thr Ser Gly Gln Ser
785                 790                 795                 800
Asn Gly Arg Asp His Gln Ala Leu Ala Lys Ala Val Gln Val His Gln
                805                 810                 815
Asp Thr Leu Arg Thr Met Tyr Phe Ala
            820                 825
```

Additional Ago2 polypeptides include, but not limited to, GenBank RefSeq NP_001158095.1, NM_001164623.2, NP_036286.2, NP_648775.1, NM_012154.4, XP_011515267.1, XP_011515268.1, XP_011515270.2, XP_559969.3, XP_016868806.1, ENSP00000220592, ENSP00000430164, ENSP00000430176, and ENSP00000431056. Ago2 biologically active fragments may comprise conserved domains, including but not limited to, the following:

1) ArgoL1: Argonaute linker 1 domain (DUF1785 (pfam08699)). ArgoL1 is a region found in argonaute proteins. It normally co-occurs with pfam02179 and pfam02171. It is a linker region between the N-terminal and the PAZ domains. It contains an alpha-helix packed against a three-stranded antiparallel beta-sheet with two long beta-strands (beta8 and beta9) of the sheet spanning one face of the adjacent N and PAZ domains. L1 together with linker 2, L2, PAZ and ArgoN forms a compact global fold.

2) Paz: Piwi Argonaut and Zwille (cl00301). PAZ domain is found in two families of proteins that are essential components of RNA-mediated gene-silencing pathways, including RNA interference, the piwi and Dicer families. PAZ functions as a nucleic-acid binding domain, with a strong preference for single-stranded nucleic acids (RNA or DNA) or RNA duplexes with single-stranded 3' overhangs. It has been suggested that the PAZ domain provides a unique mode for the recognition of the two 3'-terminal nucleotides in single-stranded nucleic acids and buries the 3' OH group, and that it might recognize characteristic 3' overhangs in siRNAs within RISC (RNA-induced silencing) and other complexes. This parent model also contains structures of an archaeal PAZ domain.

3) Piwi-like: PIWI domain (cl00628). The Paz domain is found in proteins involved in RNA silencing. RNA silencing refers to a group of related gene-silencing mechanisms mediated by short RNA molecules, including siRNAs, miRNAs, and heterochromatin-related guide RNAs. The central component of the RNA-induced silencing complex (RISC) and related complexes is Argonaute. The PIWI domain is the C-terminal portion of Argonaute and consists of two subdomains, one of which provides the 5' anchoring of the guide RNA and the other, the catalytic site for slicing. This domain is also found in closely related proteins, including the Piwi subfamily, where it is believed to perform a crucial role in germline cells, via a similar mechanism.

The term "analog" when used in conjunction with terms "nucleic acid," "DNA," "RNA," "dsRNA," and/or similar terms refers to a class of nucleic acid analogs, including but not limited to nucleic acids having non-naturally occurring nucleotides or nucleosides. Nucleic acid analogs can be produced using recombinant expression systems and optionally purified, chemically synthesized, etc. In some embodiments, a nucleic acid analog is or comprises nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine) or nucleotides (e.g., aforementioned nucleosides having 5' phosphate groups).

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy.

The term "complexing," "complexed," or "complexation" as used herein refers to any preferential or selective interacting, binding, or encapsulating of a protein (e.g., Ago2) and a nucleic acid (e.g., ds siRNA), including without limitation a covalent bond, ionic bond, salt bridge, hydrogen bond, van der Waals interaction, hydrophobic/hydrophilic interaction, electrostatic interaction, steric interaction, other associations, or any combination of any of the foregoing, to mediate the formation of a protein-nucleic acid complex (e.g., RNP). Such complexing of a protein (e.g., Ago2) and a nucleic acid (e.g., ds siRNA), to form a protein-nucleic acid complex (e.g., RNP), may facilitate co-delivery and/or pre-assembly of the protein and nucleic acid prior to or at the time of introducing said RNP to a cell, or subject in need thereof. Such pre-assembly of a protein-nucleic acid complex (e.g., RNP) may be facilitated using a cell-based process wherein the protein (e.g., Ago2) and nucleic acid (e.g., ds siRNA) are 1) introduced into a cell as components of the same vector (e.g., Bac-to-Bac™), or in separate expression vectors, constructs, or plasmids (e.g., baculovirus, lentivirus, retrovirus, or adenovirus); 2) cultured under conditions to express the protein (e.g., Ago2) and nucleic acid (e.g., ds siRNA) in the cell. The expressed protein (e.g., Ago2) and nucleic acid (e.g., ds siRNA) are assembled and complexed within the cell to form a RNP, prior to purifying and isolating the RNA. The phrases "conjoint administration" and "administered conjointly" refer to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

The phrase "disorder treatable by gene silencing" refers to a condition or disease that would benefit from reducing, decreasing, or silencing (e.g., knocking down) the excessive or undesirable expression of specific target sequence or gene, to thereby reverse, deter, manage, treat, improve, retard, slow, or eliminate the severity of the condition. Examples of disorders treatable by gene silencing, include but not limited to, cancer, infection, neurological disorder, metabolic disease, inflammation. Other diseases include, but not limited to, persistent infectious disease, proliferative diseases, neurodegenerative diseases, psychological diseases, autoimmune diseases, sexually transmitted diseases, gastro-intestinal diseases, pulmonary diseases, cardiovascular diseases, stress- and fatigue-related disorders, fungal diseases, pathogenic diseases, obesity-related disorders, viral infections, or bacterial infections. Examples of the aforementioned diseases, disorders, or conditions may be found in section "2. Protein-dsRNA complex (RNP)" below.

The term "functional" when used in conjunction with "equivalent", "derivative", "variant" or "biologically active fragment" refers to an entity or molecule which possess or retains a biological activity that is substantially similar to a biological activity of the entity or molecule in its full length or wild type form.

The term "homolog" refers to an Ago2 nucleic acid sequence, gene, or polypeptide from a different species. Ago2 homologs include, but not limited to, *D. melanogaster* (Gene ID: 39683) and *Anopheles gambiae* str. PEST (Gene ID: 3291361).

The term "modification" or "modified" as used herein refers to alterations to a "nucleic acid," "DNA," "RNA," "dsRNA," and/or similar term, including but not limited to alterations to said nucleic acid phosphate-sugar backbone, or chemical modification of bases or sugars on said nucleic acid. Such alterations can reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in dsRNA structure may be tailored to allow specific genetic inhibition while avoiding a general response to dsRNA. Likewise, bases may be modified to block the activity of adenosine deaminase. Other modifications may include biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages). In some embodiments, modifications can occur at the phosphodiester backbone linkages so as to include one or more non-phosphodiester backbone linkages such as, for example, phosphorothioate linkage and 5'-N-phosphoramidite linkage. The modified nucleic acid may be produced enzymatically, by partial/total organic synthesis, or by in vitro enzymatic or organic synthesis. A modified nucleic acid may comprise at least one, two, three, four, five, six, seven, eight, nine, or ten modifications.

Methods of chemically modifying RNA molecules can be adapted for modifying dsRNAs (see, for example, Heidenreich et al. (1997) *Nucleic Acids Res,* 25: 776-780; Wilson et al. (1994) *J. Mol Recog* 7: 89-98; Chen et al. (1995) *Nucleic Acids Res* 23: 2661-2668; Hirschbein et al. (1997) *Antisense Nucleic Acid Drug Dev* 7: 55-61). Merely to illustrate, the backbone of a dsRNA can include one or more modified internucleotidic linkage, such as phosphorothioate linkage, phosphoramidate linkage, phosphodithioate linkage, chimeric methylphosphonate-phosphodiester linkage. The dsRNA can also be derived using locked nucleic acid (LNA) nucleotides, as well as using modified ribose bases such as 2'-methoxyethoxy nucleotides; 2'-methyl-thio-ethyl nucleotides, 2'-deoxy-2'-fluoro nucleotides, 2'-deoxy-2'-chloro nucleotides, 2-azido nucleotides, 2'-O-trifluoromethyl nucleotides, 2'-O-ethyl-trifluoromethoxy nucleotides, 2'-O-difluoromethoxy-ethoxy nucleotides, 4'-thio nucleotides and 2'-O-methyl nucleotides. The dsRNA can include a terminal cap moiety at the 5'-end, the 3'-end, or both of the 5' and 3' ends. The dsRNA can include a 5'-U residue.

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA molecules, single (ssRNA) and/or double-stranded RNA (dsRNA). Nucleic acids may be a non-naturally occurring molecule, e.g., a recombinant or synthetic DNA, RNA, or DNA/RNA hybrid. Nucleic acids can be purified from natural sources, produced using recombinant expression systems and optionally purified, chemically synthesized, etc. A nucleic acid sequence is presented in the 5' to 3' direction unless otherwise indicated. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine) or nucleotides (e.g., aforementioned nucleosides having 5' phosphate groups).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "sequence identity" or "sequence homology" refers to the sequence similarity between two polypeptide molecules. When a position in both of the two compared sequences is occupied by the same base or amino acid monomer subunit, then the molecules are homologous or sequence identical at that position. The percent of homology or sequence identity between two sequences is a function of the number of matching or homologous identical positions shared by the two sequences divided by the number of positions compared×100. For example, if 6 of 10, of the positions in two sequences are the same then the two sequences are 60% homologous or have 60% sequence identity. Generally, a comparison is made when two sequences are aligned to give maximum homology. Exemplary levels of sequence identity include, but are not limited to, 80, 81, 82, 83, 84, 85, 86, 87, 88, 89, 90, 91, 92, 93, 94, 95, 96, 97, 98, 99% or more sequence identity to a given sequence.

The comparison of sequences and determination of percent homology between two sequences can be accomplished using a mathematical algorithm. The alignment can be performed using the Clustal Method, such as the CLUSTAL-W program. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

For example, the percent identity between two amino acid sequences is determined using the Needleman and Wunsch (*J. Mol. Biol.* (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online), using a NWSgapdna. CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*CABIOS*, 4:11-17 (1989)) which has been incorporated into the ALIGN program (version 2.0) (available online), using a PAM120 weight residue table, a gap length penalty of 12 and a gap penalty of 4. Other computer programs which can be used to determine identity between two sequences include, but are not limited to, the suite of BLAST programs, e.g., BLASTN, BLASTX, and TBLASTX, BLASTP and TBLASTN, publicly accessible at www.ncbi.nlm.nih.gov/BLAST.

The phrase "short double-stranded RNA", or "short dsRNA" refers to a class of double-stranded RNA (dsRNA) molecules having 25-50 nucleotides in length, or shorter. In certain embodiments, the dsRNA is 45-50 nucleotides in length, 40-45 nucleotides in length, 35-40 nucleotides in length, 30-35 nucleotides in length, 25-30 nucleotides in length, 20-25 nucleotides in length, 15-20 nucleotides in length, or 10-15 nucleotides in length. Such short dsRNA may interfere with, reduce, decrease, or silence (e.g., knockdown) the expression of specific target sequences or genes with complementary nucleotide sequences by targeting genomic DNA, resulting in no transcription, or targeting mRNA after transcription, resulting in no translation. The knockdown can be measured as an increased percent knockdown of a target sequence of about 70%, 75%, 80%, 85%, 80%, 85%, 90%, 95%, 96%, 97%, 98%, or 99% reduction in the expression of the human or non-human target gene. The knockdown activity can be measured as a sustained or prolonged silencing duration or time period of the dsRNA of up to 1, 2, 3, 4, 5, 6, 7, 8, 9, 10, 11, 12, 13, 14, or 15 days.

The term "silencing sequence," refers to a sequence within a nucleic acid molecule that is targeted by RNAi. In some embodiments, the silencing sequence comprises a RNAi target sequence that silences a human gene. In some embodiments, the silencing sequence comprises a RNAi target sequence that silences a non-human gene.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

A subject can be one who has been previously diagnosed with or identified as suffering from or having a condition in need of treatment or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. A "subject in need" of treatment for a particular condition can be a subject suspected of having that condition, diagnosed as having that condition, already treated or being treated for that condition, not treated for that condition, or at risk of developing that condition.

The term "substantial identity" of amino acid sequences (and of polypeptides having these amino acid sequences) normally means sequence identity of at least 40% compared to a reference sequence (e.g., Ago2, including homologs and isoforms thereof as set forth above) as determined using the programs described herein; preferably BLAST using standard parameters, as described. Preferred percent identity of amino acids can be any integer from 40% to 100%. More preferred embodiments include amino acid sequences that have at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity compared to a reference sequence (e.g., SEQ ID NO: 1, 2, or 3). Polypeptides that are "substantially identical" share amino acid sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

The phrase "therapeutically effective amount" as used herein refers to the concentration of an RNP that is sufficient to elicit the desired therapeutic effect. It is generally understood that the effective amount of the composition will vary according to the weight, sex, age, and medical history of the subject. Other factors which influence the effective amount may include, but are not limited to, the severity of the patient's condition, the disorder being treated, the stability of the composition, and, if desired, another type of therapeutic agent being administered with the compositions. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

2. Protein-dsRNA Complex (RNP)

One aspect of the invention relates to a RNA protein complex (RNP) comprising: (a) a short double-stranded RNA (dsRNA), or analog thereof; and (b) an Argonaute 2 protein (Ago2), or biologically active fragment or homolog thereof, wherein said Ago2 comprises a polypeptide having at least 85% sequence identity to the amino acid sequence set forth in SEQ ID NO: 1, 2, or 3. Such RNPs may be used to silence target gene expression in a host cell (such as cultured cell) or animal, including insects to mammalian hosts.

In certain embodiments, the Ago2 comprises a polypeptide having at least 86%, 87%, 88%, 89%, 90%, 91%, 92%, 93%, 94%, 95%, 96%, 97%, 98%, or 99% sequence identity to the amino acid sequence set forth in SEQ ID NO: 1, 2, or 3.

In certain embodiments, the Ago2 comprises a polypeptide having at least 86%, 87%, 88%, 89%, 90%, 91%, 92%, 93%, 94%, 95%, 96%, 97%, 98%, or 99% sequence identity to the amino acid sequence set forth in GenBank RefSeq NP_001158095.1, NM_001164623.2, NP_036286.2, NP_648775.1, NM_012154.4, XP_011515267.1, XP_011515268.1, XP_011515270.2, XP_559969.3, XP_016868806.1, ENSP00000220592, ENSP00000430164, ENSP00000430176, or ENSP00000431056. In certain embodiments, Ago2 homologs are selected from *D. melanogaster* (Gene ID: 39683) or *Anopheles gambiae* str. PEST (Gene ID: 3291361). In certain embodiments, Ago2 biologically active fragments comprise polypeptides having at least one ArgoL1 domain, Paz domain, or PIWI domain, or combinations thereof.

In certain embodiments, the dsRNA is selected from the group consisting of small interfering RNA (siRNA or ds siRNA), small hairpin RNA (shRNA), microRNA (miRNA), Piwi-interacting RNA (piRNA), heterochromatin-related guide RNAs (hc-gRNA), and antigene RNAs (agRNA). In certain embodiments, the miRNA is microRNA34a comprising a miR34a binding site (e.g., ACAACCAGCUAA-GACACUGCCA) (SEQ ID NO: 4).

In still other embodiments, multiple dsRNA (of the same or different sequence) can be provided as single concatenated nucleic acid species. In still other embodiments, the dsRNA may be operably linked to a protein, polypeptide, peptide, antibody, and the like.

In certain embodiments, the dsRNA contains a nucleotide sequence that hybridizes under physiologic conditions of the cell to the nucleotide sequence of at least a portion of a genomic sequence to reduce, decrease, or silence (e.g., knockdown) transcription at the genomic level, or an mRNA transcript for a gene to be inhibited (i.e., the "target" gene). The dsRNA need only be sufficiently similar to natural RNA that it has the ability to mediate Ago2-dependent gene silencing. Thus, the invention has the advantage of being able to tolerate sequence variations that might be expected due to genetic mutation, strain polymorphism or evolutionary divergence. The number of tolerated nucleotide mismatches between the target sequence and the dsRNA sequence is preferably no more than 1 nucleotide basepair, or no more than 2, 3, 4, or 5 nucleotide basepairs. Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 80% sequence identity, or even 100% sequence identity, between the dsRNA and the portion of the target gene is preferred. Alternatively, the dsRNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

Production of dsRNAs can be carried out by chemical synthetic methods or by recombinant nucleic acid techniques. Endogenous RNA polymerase of the treated cell may mediate transcription in vivo, or cloned RNA polymerase can be used for transcription in vitro.

The dsRNAs regulate processes essential for cell growth and development, including messenger RNA degradation, translational repression, and transcriptional gene silencing (TGS). Accordingly, the dsRNA molecules of the instant invention provide useful reagents and methods for a variety of therapeutic, prophylactic, veterinary, diagnostic, target validation, genomic discovery, genetic engineering, and pharmacogenomic applications.

The dsRNAs, or analogs thereof, described herein may complex to proteins, such as Ago2, encompassing biologically active fragment or homologue thereof, to form RNPs. In some embodiments, the dsRNA may be provided at a range of about 5 nM to about 200 nM. In some embodiments, the dsRNA may be provided at about 5 nM, about 10 nM, about 20 nM, about 30 nM, about 40 nM, about 50 nM, about 60 nM, about 70 nM, about 80 nM, about 90 nM, about 100 nM, about 110 nM, about 120 nM, about 130 nM, about 140 nM, about 150 nM, about 160 nM, about 170 nM, about 180 nM, about 190 nM, or about 200 nM. In some embodiments, the Ago2 may be provided at about 5 nM, about 10 nM, about 20 nM, about 30 nM, about 40 nM, about 50 nM, about 60 nM, about 70 nM, about 80 nM, about 90 nM, about 100 nM, about 110 nM, about 120 nM, about 130 nM, about 140 nM, about 150 nM, about 160 nM, about 170 nM, about 180 nM, about 190 nM, or about 200 nM, so as to achieve a 1:0.5, 0.5:1, 1:1, 1:2, 2:1, 1:3, 3:1, 1:4, 4:1, 1:5, or 5:1 molar ratio when complexed with the dsRNA to form an RNP. Such RNPs may be admixed, encapsulated, conjugated or otherwise associated with other molecules, molecule structures mixtures of compounds, as for example, liposomes, polymers, receptor targeted molecules, oral, rectal, topical or other formulations, for assisting in uptake, distribution and/or absorption. The subject RNPs can be provided in formulations also including penetration enhancers, carrier compounds and/or transfection agents.

Representative United States patents that teach the preparation of such uptake, distribution and/or absorption assisting formulations which can be adapted for delivery of RNPs, include, but are not limited to, U.S. Pat. Nos. 5,108,921; 5,354,844; 5,416,016; 5,459,127; 5,521,291; 51543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756.

The RNPs of the invention also encompass any pharmaceutically acceptable salts, esters or salts of such esters, or any other compound which, upon administration to an animal including a human, is capable of providing (directly or indirectly) the biologically active metabolite or residue thereof. Accordingly, for example, the disclosure is also drawn to RNPs and pharmaceutically acceptable salts of the RNPs, pharmaceutically acceptable salts of such RNPs, and other bioequivalents.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,NI-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.,* 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids.

Upon complexation or encapsulation, the RNP comprising Ago2 and dsRNA have enhanced properties when introduced in a cell or administered to a subject in need thereof. Such enhanced properties include, but not limited to, enhanced target knockdown capabilities, enhanced silencing activity, improved stability, and decreased toxicity when introduced into a cell or subject in need thereof. The enhanced target knockdown can be measured as an increased percent knockdown of a target sequence of about 70%, 75%, 80%, 85%, 80%, 85%, 90%, 95%, 96%, 97%, 98%, or 99% knockdown of the human or non-human gene. The enhanced silencing activity can be measured as a sustained or prolonged silencing duration or time period of the RNPs of up to 2, 3, 4, 5, 6, 7, 8, 9, 10, 11, 12, 13, 14, or 15 days.

The present invention encompasses the recognition that the RNPs can be designed and/or prepared to simultaneously deliver to a target site (e.g., to a cancer cell) a plurality of different nucleic acid agents (e.g., RNPs), each of which is directed to a different specific molecular target of interest.

In some embodiments, the dsRNA of the RNP described herein may comprise silencing sequences direct to any human or non-human target gene associated with a particular disease, disorder, or condition of interest (e.g., cancer, infection, neurological disorder, metabolic disease, inflammation, etc). Other diseases include, but not limited to, persistent infectious disease, proliferative diseases, neurodegenerative diseases, cancers, psychological diseases, metabolic diseases, autoimmune diseases, sexually transmitted diseases, gastro-intestinal diseases, pulmonary diseases, cardiovascular diseases, stress- and fatigue-related disorders, fungal diseases, pathogenic diseases, obesity-related disorders, viral infections, bacterial infections, or biomarkers regarding same. Viral infectious diseases including human papilloma virus (HPV), hepatitis A Virus (HAV), hepatitis B Virus (HBV), hepatitis C Virus (HCV), retroviruses such as human immunodeficiency virus (HIV-1 and HIV-2), herpes viruses such as Epstein Barr Virus (EBV), cytomegalovirus (CMV), HSV-1 and HSV-2, influenza virus, Hepatitis A and B, FIV, lentiviruses, pestiviruses, West Nile Virus, measles, smallpox, cowpox, ebola, coronavirus, retrovirus, herpesvirus, potato S virus, simian Virus 40 (SV40), Mouse Mammary Tumor Virus (MMTV) promoter, Moloney virus, ALV, Cytomegalovirus (CMV), Epstein Barr Virus (EBV), or Rous Sarcoma Virus (RSV). In addition, bacterial, fungal and other pathogenic diseases are included, such as *Aspergillus, Brugia, Candida, Chikungunya, Chlamydia, Coccidia, Cryptococcus, Dengue, Dirofilaria, Gonococcus, Histoplasma, Leishmania, Mycobacterium, Mycoplasma, Paramecium, Pertussis, Plasmodium, Pneumococcus, Pneumocystis, P. vivax* in *Anopheles* mosquito vectors, *Rickettsia, Salmonella, Shigella, Staphylococcus, Streptococcus, Toxoplasma* and *Vibriocholerae*. Exemplary species include *Neisseria gonorrhea, Mycobacterium tuberculosis, Candida albicans, Candida tropicalis, Trichomonas vaginalis, Haemophilus vaginalis*, Group B *Streptococcus* sp., *Microplasma hominis, Hemophilus ducreyi, Granuloma inguinale, Lymphopathia venereum, Treponema pallidum, Brucella abortus. Brucella melitensis, Brucella suis, Brucella canis, Campylobacter fetus, Campylobacter fetus intestinalis, Leptospira pomona, Listeria monocytogenes, Brucella ovis, Chlamydia psittaci, Trichomonas foetus, Toxoplasma gondii, Escherichia coli, Actinobacillus equuli, Salmonella abortus ovis, Salmonella abortus equi, Pseudomonas aeruginosa, Corynebacterium equi, Corynebacterium pyogenes, Actinobaccilus seminis, Mycoplasma bovigenitalium, Aspergillus fumigatus, Absidia ramosa, Trypanosoma equiperdum, Clostridium tetani, Clostridium botulinum*; or, a fungus, such as, e.g., *Paracoccidioides brasiliensis*; or other pathogen, e.g., *Plasmodium falciparum*. Also included are National Institute of Allergy and Infectious Diseases (NIAID) priority pathogens. These include Category A agents, such as variola major (smallpox), *Bacillus anthracis* (anthrax), *Yersinia pestis* (plague), *Clostridium botulinum* toxin (botulism), *Francisella tularensis* (tularaemia), filoviruses (Ebola hemorrhagic fever, Marburg hemorrhagic fever), arenaviruses (Lassa (Lassa fever), Junin (Argentine hemorrhagic fever) and related viruses); Category B agents, such as *Coxiella burnetti* (Q fever), *Brucella* species (brucellosis), *Burkholderia mallei* (glanders), alphaviruses (Venezuelan encephalomyelitis, eastern & western equine encephalomyelitis), ricin toxin from *Ricinus communis* (castor beans), epsilon toxin of *Clostridium perfringens; Staphylococcus* enterotoxin B, *Salmonella* species, *Shigella dysenteriae, Escherichia coli* strain O157:H7, *Vibrio cholerae, Cryptosporidium parvum*; Category C agents, such as nipah virus, hantaviruses, yellow fever in *Aedes* mosquitoes, and multidrug-resistant tuberculosis; helminths, such as *Schistosoma* and *Taenia*; and protozoa, such as *Leishmania* (e.g., *L. mexicana*) in sand flies, *Plasmodium*, Chagas disease in assassin bugs.

Bacterial pathogens include, but are not limited to, such as bacterial pathogenic gram-positive cocci, which include but are not limited to: pneumococci; staphylococci; and streptococci. Pathogenic gram-negative cocci include: meningococci; and gonococci. Pathogenic enteric gram-negative bacilli include: enterobacteriaceae; pseudomonas, acinetobacteria and eikenella; melioidosis; salmonella; shigellosis; hemophilus; chancroid; brucellosis; tularemia; yersinia (pasteurella); streptobacillus moniliformis and spirilum; *Listeria monocytogenes*; erysipelothrix rhusiopathiae; diphtheria; cholera; anthrax; and donovanosis (granuloma inguinale). Pathogenic anaerobic bacteria include; tetanus; botulism; other clostridia; tuberculosis; leprosy; and other mycobacteria. Pathogenic spirochetal diseases include: syphilis; treponematoses: yaws, pinta and endemic syphilis; and leptospirosis. Other infections caused by higher pathogen bacteria and pathogenic fungi include: actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include rickettsial and rickettsioses. Examples of mycoplasma and chlamydial infections include: Mycoplasma pneumoniae; lymphogranuloma venereum; psittacosis; and perinatal chlamydial infections. Pathogenic protozoans and helminths and infections eukaryotes thereby include: amebiasis; malaria; leishmaniasis; trypanosomiasis; toxoplasmosis; Pneumocystis carinii; giardiasis; trichinosis; filariasis; schistosomiasis; nematodes; trematodes or flukes; and cestode (tapeworm) infections.

The term "cancer" as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

Additional non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, lung cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, Wilms tumor.

The terms "metabolic disorder" and "obesity related disorders" are used interchangeably herein and include a disorder, disease or condition which is caused or characterized by an abnormal metabolism (i.e., the chemical changes in living cells by which energy is provided for vital processes and activities) in a subject. Metabolic disorders include diseases, disorders, or conditions associated with aberrant thermogenesis or aberrant adipose cell (e.g., brown or white adipose cell) content or function. Metabolic disorders can detrimentally affect cellular functions such as cellular proliferation, growth, differentiation, or migration, cellular regulation of homeostasis, inter- or intra-cellular communication; tissue function, such as liver function, muscle function, or adipocyte function; systemic responses in an organism, such as hormonal responses (e.g., insulin response). Examples of metabolic disorders include obesity, including insulin resistant obesity, diabetes, hyperphagia, endocrine abnormalities, triglyceride storage disease, dyslipidemia, Bardet-Biedl syndrome, Lawrence-Moon syndrome, Prader-Labhart-Willi syndrome, anorexia, and cachexia. Other examples, include, bulimia, polycystic ovarian disease, craniopharingioma, the Prader-Willi Syndrome, Frohlich's syndrome, Type II diabetics, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia.

The term "neurological disease" refers to a condition having as a component a central or peripheral nervous system malfunction. A neurological disease may cause a disturbance in the structure or function of the nervous system resulting from developmental and functional abnormalities, disease, genetic defects, injury or toxin. These disorders may affect the central nervous system (e.g., the brain, brainstem and cerebellum), the peripheral nervous system (e.g., the cranial nerves, spinal nerves, and sympathetic and parasympathetic nervous systems) and/or the autonomic nervous system (e.g., the part of the nervous system that regulates involuntary action and that is divided into the sympathetic and parasympathetic nervous systems). Examples of neurological disorders, include but not limited to, familial and sporadic amyotrophic lateral sclerosis (FALS and ALS, respectively), familial and sporadic Parkinson's disease, Huntington's disease, familial and sporadic Alzheimer's disease, Fragile X syndrome, multiple sclerosis, olivopontocerebellar atrophy, multiple system atrophy, progressive supranuclear palsy, diffuse Lewy body disease, corticodentatonigral degeneration, progressive familial myoclonic epilepsy, strionigral degeneration, torsion dystonia, familial tremor, Down's syndrome, Gilles de la Tourette syndrome, Hallervorden-Spatz disease, dementia pugilistica, AIDS dementia, age related dementia, age associated memory impairment, and amyloidosis-related neurodegenerative diseases such as those caused by the prion protein (PrP) which is associated with transmissible spongiform encephalopathy (Creutzfeldt-Jakob disease, Gerstmann-Straussler-Scheinker syndrome, scrapie, and kuru), and those caused by excess cystatin C accumulation (hereditary cystatin C angiopathy); and (ii) acute neurodegenerative disorders such as traumatic brain injury (e.g., surgery-related brain injury), cerebral edema, peripheral nerve damage, spinal cord injury, Leigh's disease, Guillain-Barre syndrome, lysosomal storage disorders such as lipofuscinosis, Alper's disease, vertigo as result of CNS degeneration; pathologies arising with chronic alcohol or drug abuse including, for example, the degeneration of neurons in locus coeruleus and cerebellum; pathologies arising with aging including degeneration of cerebellar neurons and cortical neurons leading to cognitive and motor impairments; and pathologies arising with chronic amphetamine abuse including degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor) and Wernicke-Korsakoff s related dementia.

In certain embodiments, the silencing sequence of the dsRNA may target sequences or genes, including but not limited to, kinases, phosphatases, lipid signaling molecules, adaptor/scaffold proteins, GTPase activating proteins, isomerases, deacetylases, methylases, demethylases, tumor suppressor genes, caspases, proteins involved in apoptosis, cell cycle regulators, molecular chaperones, metabolic enzymes, vesicular transport proteins, cytokines, cytokine regulators, ubiquitination enzymes, adhesion molecules, cytoskeletal/contractile proteins, heterotrimeric G proteins, small molecular weight GTPases, guanine nucleotide exchange factors, hydroxylases, proteases, ion channels, molecular transporters, transcription factors/DNA binding factors, regulators of transcription, and regulators of translation. Target sequences or genes may be members of any cell signaling pathway, including but not limited to MAP kinase, PI3K/Akt, NFkB, WNT, RAS/RAF/MEK/ERK, JNK/SAPK, p38 MAPK, Src Family Kinases, JAK/STAT and/or PKC signaling pathways. Examples of signaling molecules include, but are not limited to, HER receptors, PDGF receptors, Kit receptor, FGF receptors, Eph receptors, Trk receptors, IGF receptors, Insulin receptor, Met receptor, Ret, VEGF receptors, TIE1, TIE2, FAK, Jak1, Jak2, Jak3, Tyk2, Src, Lyn, Fyn, Lck, Fgr, Yes, Csk, Abl, Btk, ZAP70, Syk, IRAKs, cRaf, ARaf, BRAF, Mos, Lim kinase, ILK, Tpl, ALK, TGFβ receptors, BMP receptors, MEKKs, ASK, MLKs, DLK, PAKs, Mek 1, Mek 2, MKK3/6, MKK4/7, ASK1, Cot, NIK, Bub, Myt 1, Wee1, Casein kinases, PDK1, SGK1, SGK2, SGK3, Akt1, Akt2, Akt3, p90Rsks, p70S6 Kinase, Prks, PKCs, PKAs, ROCK 1, ROCK 2, Auroras, CaMKs, MNKs, AMPKs, MELK, MARKs, Chk1, Chk2, LKB-1, MAPKAPKs, Pim1, Pim2, Pim3, IKKs, Cdks, Jnks, Erks, IKKs, GSK3α, GSK3β, Cdks, CLKs, PKR, PI3-Kinase class 1, class 2, class 3, mTor, SAPK/JNK1,2,3, p38s, PKR, DNA-PK, ATM, ATR, Receptor protein tyrosine phosphatases (RPTPs), LAR phosphatase, CD45, Non receptor tyrosine phosphatases (NPRTPs), SHPs, MAP kinase phosphatases (MKPs), Dual Specificity phosphatases (DUSPs), CDC25 phosphatases, Low molecular weight tyrosine phosphatase, Eyes absent (EYA) tyrosine phosphatases, Slingshot phosphatases (SSH), serine phosphatases, PP2A, PP2B, PP2C, PP1, PP5, inositol phosphatases, PTEN, SHIPs, myotubularins, phosphoinositide kinases, phopsholipases, prostaglandin synthases, 5-lipoxygenase, sphingosine kinases, sphingomyelinases, adaptor/scaffold proteins, Shc, Grb2, BLNK, LAT, B cell adaptor for PI3-kinase (BCAP), SLAP, Dok, KSR, MyD88, Crk, CrkL, GAD, Nck, Grb2 associated binder (GAB), Fas associated death domain (FADD), TRADD, TRAF2, RIP, T-Cell leukemia family, IL-2, IL-4, IL-8, IL-6, interferon-β, interferon-α, suppressors of cytokine signaling (SOCs), Cbl, SCF ubiquitination ligase complex, APC/C, adhesion molecules, integrins, Immunoglobulin-like adhesion molecules, selectins, cadherins, catenins, focal adhesion kinase, p130CAS, fodrin, actin, paxillin, myosin, myosin binding proteins, tubulin, eg5/KSP, CENPs, β-adrenergic receptors, muscarinic receptors, adenylyl cyclase receptors, small molecular weight GTPases, H-Ras, K-Ras, N-Ras, Ran, Rac, Rho, Cdc42, Arfs, RABs, RHEB, Vav, Tiam, Sos, Dbl, PRK, TSC1,2, Ras-GAP, Arf-GAPs, Rho-GAPs, caspases, Caspase 2, Caspase 3, Caspase 6, Caspase 7, Caspase 8, Caspase 9, Bcl-2, Mcl-1, Bcl-XL, Bcl-w, Bcl-B, A1, Bax, Bak, Bok, Bik, Bad, Bid, Bim, Bmf, Hrk, Noxa, Puma, IAPB, XIAP, Smac, survivin, Plk1, Cdk4, Cdk 6, Cdk 2, Cdk1, Cdk 7, Cyclin D, Cyclin E, Cyclin A, nucleoside transporters, Ets, Elk, SMADs, Rel-A (p65-NFKB), CREB, NFAT, ATF-2, AFT, Myc, Fos, Spl, Egr-1, T-bet, β-catenin, HIFs, FOXOs, E2Fs, SRFs, TCFs, Egr-1, β-catenin, STAT1, STAT 3, STAT 4, STAT 5, STAT 6, Cyclin B, Rb, p16, p14Arf, p27KIP, p21CIP, molecular chaperones, Hsp90s, Hsp70, Hsp27, metabolic enzymes, Acetyl-CoA Carboxylase, ATP citrate lyase, nitric oxide synthase, caveolins, endosomal sorting complex required for transport (ESCRT) proteins, vesicular protein sorting (Vsps), hydroxylases, prolyl-hydroxylases PHD-1, 2 and 3, asparagine hydroxylase FIH transferases, Pin1 prolyl isomerase, topoisomerases, deacetylases, Histone deacetylases, sirtuins, histone acetylases, CBP/P300 family, MYST family, ATF2, DNA methyl transferases, DMNT1, DMNT3a, DMNT3b, Histone H3K4 demethylases, H3K27, JHDM2A, UTX, VHL, WT-1, p53, Hdm, PTEN, ubiquitin proteases, urokinase-type plasminogen activator (uPA) and uPA receptor (uPAR) system, cathepsins, metalloproteinases, esterases, hydrolases, separase, potassium channels, sodium channels, multi-drug resistance proteins, P-Gycoprotein, p53, WT-1, HMGA, pS6, 4EPB-1, eIF4E-binding protein, RNA polymerase, initiation factors, elongation factors.

3. Method and Uses of the RNPs

The RNPs described herein can elicit higher and superior silencing of target gene expression over conventional siRNA methods. The subject RNPs can induce transcriptional and/or post-transcriptional gene silencing of the target gene. Accordingly, one aspect of the invention relates to methods for silencing the expression of a target gene in a host cell (such as cultured cell). In one embodiment, the method for silencing the expression of a target gene in a cell comprises the steps of: (i) providing a dsRNA, or analog thereof; (ii) complexing the dsRNA to an Ago2, or biologically active fragment or homolog thereof; (iii) forming an Ago2 protein-dsRNA complex (RNP) comprising the dsRNA and the Ago2; (iv) introducing into the cell the RNP; and (v) inducing gene silencing of the target gene.

Such pre-assembled or encapsulated RNPs comprising the dsRNA and the Ago2, when co-delivered, or upon introduction to a cell, have enhanced properties. Such enhanced properties include, but not limited to, enhanced target knockdown capabilities, enhanced silencing activity, improved stability, and decreased toxicity when introduced into a cell or subject in need thereof. The enhanced target knockdown can be measured as an increased percent knockdown of a target sequence of about 70%, 75%, 80%, 85%, 80%, 85%, 90%, 95%, 96%, 97%, 98%, or 99% knockdown of the human or non-human gene. The enhanced silencing activity can be measured as a sustained or prolonged silencing duration or time period of the RNPs of up to 2, 3, 4, 5, 6, 7, 8, 9, 10, 11, 12, 13, 14, or 15 days.

Another aspect of the invention relates a method of gene silencing comprising administering the RNPs described herein to treat a subject in need thereof. In some embodiments of the methods of gene silencing, a therapeutically effective amount of the RNP is administered. In some embodiments, the subject is a mammal. For example, the subject may be a mouse or a human. In some embodiments, a plurality of RNPs are delivered to the target site.

In some embodiments, a plurality of RNP comprises one or more dsRNA that targets one or more genes associated with a particular disease, disorder, or condition of interest (e.g., cancer, infection, neurological disorder, metabolic disease, inflammation, etc).

The present invention encompasses the recognition that the RNPs can be designed and/or prepared to simultaneously deliver to a target site (e.g., to a diseased cell) a plurality of different dsRNAs, each of which is directed to a different specific molecular target of interest. To give but one example, RNPs can be designed and/or pre-assembled with desired relative numbers of copies of different sequences of interest (e.g., complementary to different dsRNAs of interest), so as to achieve precise control over the stoichiometry of delivered dsRNA(s). In some embodiments, such control achieves synergistic effects (e.g., with respect to inhibiting tumor growth). In some embodiments, the RNPs comprise a plurality of dsRNAs, each of which targets a different cancer pathway, for example, as an dsRNA that inhibits expression of a protein whose activity contributes to or supports the pathway.

In some embodiments, provided pharmaceutical compositions are administered or implanted using methods known in the art, including invasive, surgical, minimally invasive and non-surgical procedures, depending on the subject, target sites, and agent(s) to be delivered. Pharmaceutical compositions described herein can be delivered to a cell, tissue, organ of a subject. Examples of target sites include but are not limited to the eye, pancreas, kidney, liver, stomach, muscle, heart, lungs, lymphatic system, thyroid gland, pituitary gland, ovaries, prostate, skin, endocrine glands, ear, breast, urinary tract, brain or any other site in a subject.

Typical dosages of a therapeutically effective amount of the RNPs can be in the ranges recommended by the manufacturer where known therapeutic compositions are used, and also as indicated to the skilled artisan by the in vitro responses in cells or in vivo responses in animal models. Such dosages typically can be reduced by up to about an order of magnitude in concentration or amount without losing relevant biological activity. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models. In various embodiments, the RNP may be administered once a day (SID/QD), twice a day (BID), three times a day (TID), four times a day (QID), or more, so as to administer a therapeutically effective amount of the RNP to the subject, where the therapeutically effective amount is any one or more of the doses described herein.

In some embodiments, the RNP is administered at about 0.001 to 0.01 mg/kg, 0.01 to 0.1 mg/kg, 0.1 to 0.5 mg/kg, 0.5 to 5 mg/kg, 5 to 10 mg/kg, 10 to 20 mg/kg, 20 to 50 mg/kg, 50 to 100 mg/kg, 100 to 200 mg/kg, 200 to 300 mg/kg, 300 to 400 mg/kg, 400 to 500 mg/kg, 500 to 600 mg/kg, 600 to 700 mg/kg, 700 to 800 mg/kg, 800 to 900 mg/kg, or 900 to 1000 mg/kg. In some embodiments, the RNP is administered 1-3 times per day or 1-7 times per week. Still some embodiments, the RNP is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. Here, "mg/kg" refers to mg per kg body weight of the subject. In certain embodiments, the RNP is administered to a human.

In some embodiments, the therapeutically effective amount of the RNP is any one or more of about 0.01 to 0.05 µg/kg/day, 0.05-0.1 µg/kg/day, 0.1 to 0.5 µg/kg/day, 0.5 to 5 µg/kg/day, 5 to 10 µg/kg/day, 10 to 20 µg/kg/day, 20 to 50 µg/kg/day, 50 to 100 µg/kg/day, 100 to 150 µg/kg/day, 150 to 200 µg/kg/day, 200 to 250 µg/kg/day, 250 to 300 µg/kg/day, 300 to 350 µg/kg/day, 350 to 400 µg/kg/day, 400 to 500 µg/kg/day, 500 to 600 µg/kg/day, 600 to 700 µg/kg/day, 700 to 800 µg/kg/day, 800 to 900 µg/kg/day, 900 to 1000 µg/kg/day, 0.01 to 0.05 mg/kg/day, 0.05-0.1 mg/kg/day, 0.1 to 0.5 mg/kg/day, 0.5 to 1 mg/kg/day, 1 to 5 mg/kg/day, 5 to 10 mg/kg/day, 10 to 15 mg/kg/day, 15 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day, 900 to 1000 mg/kg/day or a combination thereof. Here, "µg/kg/day" or "mg/kg/day" refers to g or mg per kg body weight of the subject per day.

In some embodiments, the RNP is administered at about 0.01 to 0.1 mcg/kg, 0.1 to 0.5 mcg/kg, 0.5 to 5 mcg/kg, 5 to 10 mcg/kg, 10 to 20 mcg/kg, 20 to 50 mcg/kg, 50 to 100 mcg/kg, 100 to 200 mcg/kg, 200 to 300 mcg/kg, 300 to 400 mcg/kg, 400 to 500 mcg/kg, 500 to 600 mcg/kg, 600 to 700 mcg/kg, 700 to 800 mcg/kg, 800 to 900 mcg/kg, or 900 to 1000 mcg/kg. In some embodiments, the RNP is administered 1-3 times per day or 1-7 times per week. Still in some embodiments, the RNP is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. Here, "mcg/kg" refers to mcg per kg body weight of the subject. In certain embodiments, the RNP is administered to a human.

In accordance with the invention, various routes may be utilized to administer the RNP of the claimed methods, including but not limited to aerosol, nasal, oral, transmucosal, transdermal, parenteral, implantable pump, continuous infusion, topical application, capsules and/or injections. In various embodiments, the RNP are administered intravenously, intramuscularly, subcutaneously, intraperitoneally, orally or via inhalation. The RNP may be administered via the same or separate routes.

In various embodiments, the RNP are administered concomitantly, concurrently or sequentially with other therapeutic agents. In some embodiments, a therapeutic agent is or comprises a small molecule and/or organic compound with pharmaceutical activity. In some embodiments, a therapeutic agent is a clinically-used drug. In some embodiments, a therapeutic agent is or comprises an antibiotic, anti-viral agent, anesthetic, anticoagulant, anti-cancer agent, inhibitor of an enzyme, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, anti-glaucoma agent, neuroprotectant, angiogenesis inhibitor, etc.

In some embodiments, a therapeutic agent may be a mixture of pharmaceutically active agents. For example, a local anesthetic may be delivered in combination with an anti-inflammatory agent such as a steroid. Local anesthetics may also be administered with vasoactive agents such as epinephrine. To give but another example, an antibiotic may be combined with an inhibitor of the enzyme commonly produced by bacteria to inactivate the antibiotic (e.g., penicillin and clavulanic acid).

In some embodiments, a therapeutic agent may be an antibiotic. Exemplary antibiotics include, but are not limited to, β-lactam antibiotics, macrolides, monobactams, rifamycins, tetracyclines, chloramphenicol, clindamycin, lincomycin, fusidic acid, novobiocin, fosfomycin, fusidate sodium, capreomycin, colistimethate, gramicidin, minocycline, doxycycline, bacitracin, erythromycin, nalidixic acid, vancomycin, and trimethoprim. For example, β-lactam antibiotics can be ampicillin, aziocillin, aztreonam, carbenicillin, cefoperazone, ceftriaxone, cephaloridine, cephalothin, cloxacillin, moxalactam, penicillin G, piperacillin, ticarcillin and any combination thereof.

An antibiotic used in accordance with the present disclosure may be bacteriocidial or bacteriostatic. Other antimicrobial agents may also be used in accordance with the present disclosure. For example, anti-viral agents, anti-protazoal agents, anti-parasitic agents, etc. may be of use.

In some embodiments, a therapeutic agent may be or comprise an anti-inflammatory agent. Anti-inflammatory agents may include corticosteroids (e.g., glucocorticoids), cycloplegics, non-steroidal anti-inflammatory drugs (NSAIDs), immune selective anti-inflammatory derivatives (ImSAIDs), and any combination thereof. Exemplary NSAIDs include, but not limited to, celecoxib (Celebrex®); rofecoxib (Vioxx®), etoricoxib (Arcoxia®), meloxicam (Mobic®), valdecoxib, diclofenac (Voltaren®, Cataflam®), etodolac (Lodine®), sulindac (Clinori®), aspirin, alclofenac, fenclofenac, diflunisal (Dolobid®), benorylate, fosfosal, salicylic acid including acetylsalicylic acid, sodium acetylsalicylic acid, calcium acetylsalicylic acid, and sodium salicylate; ibuprofen (Motrin), ketoprofen, carprofen, fenbufen, flurbiprofen, oxaprozin, suprofen, triaprofenic acid, fenoprofen, indoprofen, piroprofen, flufenamic, mefenamic, meclofenamic, niflumic, salsalate, rolmerin, fentiazac, tilomisole, oxyphenbutazone, phenylbutazone, apazone, feprazone, sudoxicam, isoxicam, tenoxicam, piroxicam (Feldene®), indomethacin (Indocin®), nabumetone (Relafen®), naproxen (Naprosyn®), tolmetin, lumiracoxib, parecoxib, licofelone (ML3000), including pharmaceutically acceptable salts, isomers, enantiomers, derivatives, prodrugs, crystal polymorphs, amorphous modifications, co-crystals and combinations thereof.

In various embodiments, the RNP is administered before, during or after administering the therapeutic agent. As a non-limiting example, the RNP may be administered, for example, daily at the aforementioned dosages, and the therapeutic agent may be administered, for example, daily, weekly, biweekly, every fortnight and/or monthly at the aforementioned dosages. As another non-limiting example, the RNP may be administered, for example, daily, weekly, biweekly, every fortnight and/or monthly, at the aforementioned dosages, and the therapeutic agent may be administered, for example, daily at the aforementioned dosages. Further, each of the RNP and therapeutic agent may be administered daily, weekly, biweekly, every fortnight and/or monthly, wherein the RNP is administered at the aforementioned dosages on a day different than the day on which the therapeutic agent is administered at the aforementioned dosages.

4. Pharmaceutical RNPs

The RNPs, compositions, and methods of the present invention may be utilized to treat a subject in need thereof. In certain embodiments, the individual is a mammal such as a human, or a non-human mammal. When administered to an animal, such as a human, the RNPs are preferably administered in a pharmaceutical composition comprising, for example, the RNP and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The pharmaceutical composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a composition. Such physiologically acceptable agents include, for example, carbohydrates, such as glucose, sucrose or dextrans, antioxidants, such as ascorbic acid or glutathione, chelating agents, low molecular weight proteins or other stabilizers or excipients. In some embodiments the proteins are polypeptides such as polyamines. In some embodiments, the polyamines may comprise the polyamines depicted in FIG. 8A. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, the RNP. Liposomes, for example, which comprise phospholipids or other lipids, are nontoxic, physiologically acceptable and metabolizable carriers that are relatively simple to make and administer.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The composition may also be formulated for inhalation. In certain embodiments, a composition may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the composition which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active composition, such as the RNP with the carrier and, optionally, one or more accessory ingredients. In general, the formulations are prepared by uniformly and intimately bringing into association the RNP with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of the RNP as an active ingredient. Compositions may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered composition moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compositions, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compositions with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active composition.

Formulations of the pharmaceutical compositions for administration to the mouth may be presented as a mouthwash, or an oral spray, or an oral ointment.

Alternatively, or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active composition may be mixed under sterile conditions with a pharmaceutically acceptable carrier, and with any preservatives, buffers, or propellants that may be required.

The ointments, pastes, creams and gels may contain, in addition to an active composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active composition, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a composition to the body. Such dosage forms can be made by dissolving or dispersing the active composition in the proper medium. Absorption enhancers can also be used to increase the flux of the composition across the skin. The rate of such flux can be controlled by either providing a rate controlling membrane or dispersing the composition in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more RNP in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compositions in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compositions can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a composition at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular composition or combination of compositions employed, or the ester, salt or amide thereof, the route of administration, the time of administration, the rate of excretion of the particular composition(s) being employed, the duration of the treatment, other drugs, compositions and/or materials used in combination with the particular composition(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition at levels lower than that required in order to achieve the desired therapeutic effect and gradually increase the dosage until the desired effect is achieved.

In general, a suitable daily dose of an active composition used in the methods of the invention will be that amount of the composition that is the lowest dose effective to produce a therapeutic effect. Such a therapeutically effective dose will generally depend upon the factors described above.

If desired, the therapeutically effective daily dose of the active composition may be administered as one, two, three, four, five, six or more sub-doses administered separately at appropriate intervals throughout the day, optionally, in unit dosage forms. In certain embodiments of the present invention, the active composition may be administered two or three times daily. In preferred embodiments, the active composition will be administered once daily.

The patient receiving this treatment may be any animal in need, including primates, in particular humans, and other mammals such as equines, cattle, swine and sheep; and poultry and pets in general.

In certain embodiments, the RNP, may be conjointly administered with another type of therapeutic agent.

This invention includes the use of pharmaceutically acceptable salts of the RNPs and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

The term "pharmaceutically acceptable basic addition salt" as used herein means any non-toxic organic or inorganic base addition salt of any acid compounds. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

The invention now being generally described, it will be more readily understood by reference to the following examples which are included merely for purposes of illustration of certain aspects and embodiments of the present invention, and are not intended to limit the invention.

EXEMPLIFICATION

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1: Materials and Methods

Chemicals and Antibodies

β-benzyl-L-aspartate and triphosgene were purchased from Chem-Impex (Wood Dale, Ill., USA) and used without further purification. Diethylenetriamine, triethylenetetraamine, tetraethylenepentamine, and pentaethylenehexamine were respectively purchased from Alfa Aesar (Haverhill, Mass., USA), MP Biomedicals (Santa Ana, Calif., USA), TCI America (Portland, Oreg., USA), and Acros Organics (Pittsburgh, Pa., USA) and used as received. N, N-Dimethylformamide (DMF) was dried and stored over 3 Å molecular sieves under an argon atmosphere prior to use. All other reagents were purchased from Sigma-Aldrich (St. Louis, Mo., USA) and used as received. Cyanine 5 succinimidyl esters (potassium salt) were purchased from AAT bioquest (Sunnyvale, Calif., USA). CFSE cell proliferation kit was from Invitrogen (Grand Island, N.Y., USA). Primary antibodies used in this study were: β Tubulin (G-8), eIF4E (P-2) are from Santa Cruz Biotech (Dallas, Tex., USA). APC anti-mouse CD8a and TruStain fcX™ (anti-mouse CD16/32) antibodies were from Biolegend (San Diego, Calif., USA). siRNA sequences are shown below in Table 1.

TABLE 1 siRNA sequences

| siRNA target | Sense sequence | Antisense sequence |
| --- | --- | --- |
| d2GFP | 5'pGCACCAUCUUCUUCAAGGAdTdT (SEQ ID NO: 5) | 5'pUCCUUGAAGAAGAUGGUGCdTdT (SEQ ID NO: 6) |
| miR34a mimic# | 5'pAmCAAmCmCAGmCmUAAGAmCAmCm UGmCmCA (SEQ ID NO: 7) | 5'pUGGmCAGUGUCUmUAGCUGGU UGU (SEQ ID NO: 8) |
| firefly luciferase | 5'pGGACGAGGACGAGCACUUCdTdT (SEQ ID NO: 9) | 5'pGAAGUGCUCGUCCUCGUCCdTd T (SEQ ID NO: 10) |
| Mouse STAT3## | 5'pCAGGGUGUCAGAUCACAUGGGCUAAd TdT (SEQ ID NO: 11) | 5'pUUAGCCCAUGUGAUCUGACACC CUGdTdT (SEQ ID NO: 12) |

The mA, mG, mC, and mU are 2'O-methyl RNA (Uchida, H. et al. (2014) *J Am Chem Soc* 136(35):12396-405; Elkayam, E. et al. (2012) *Cell* 150(1):100-10). The miR34a mimic was purchased from Dharmacon. All siRNAs were synthesized by Sigma Aldrich.

Cell Lines and Mice

HEK293T, NIH3T3, and B16F10 cells were obtained from American Type Culture Collection (ATCC, Rockville, Md., USA) and cultured in DMEM (Invitrogen, Grand Island, N.Y., USA) with 10% FBS and 1% Penicillin/Streptomycin. Cells were tested to be *mycoplasma*-free by the High Throughput Screening Facility at The Koch Institute for Integrative Cancer Research at MIT (Cambridge, Mass., USA). C57BL/6 mice (Jackson Laboratory, Bar Harbor, Me., USA) were housed in the MIT Animal Facility. All mouse studies were performed in the context of an animal protocol approved by the MIT Division of Comparative Medicine following federal, state, and local guidelines.

Synthesis and Characterization of poly(β-benzyl-L-aspartate) PBLD

A flame dried 100 mL Schlenk flask equipped with a magnetic stir bar and rubber septum was charged with NCA (3.28 g, 13.2 mmol) and DMF (30 mL). Hexylamine (17.4 μL, 0.132 mmol) was added via micropipette with stirring and the reaction was sparged with a steady stream of argon at RT for 48 hr. The reaction was added to water, and the resulting precipitate was collected by centrifugation, washed 3 times with water, and dried in vacuo to give a white powder (2.44 g, 11.9 mmol repeat units, 90%).

$^1$H NMR (400 MHz, DMSO): δ 8.37-7.98 (m, 1H), 7.51-7.08 (m, 5H), 5.21-4.92 (m, 2H), 4.74-4.48 (m, 1H), 2.98-2.54 (m, 2H).

Synthesis and Characterization of Polyamines

Polyamines were synthesized according to a modified procedure of Uchida and the coworkers (Uchida, H. et al. (2014) *J Am Chem Soc* 136(35): 12396-405). Briefly, to a chilled solution of PBLD in N-Methyl-2-pyrrolidone (NMP) (2 mL), 50 equivalents of polyamine diluted two-fold with NMP was added dropwise with stirring. After stirring for 2 hours at 0° C., the pH was adjusted to 1 with dropwise addition while stirring of cold 6 N HCl. The resulting solution was dialyzed from a regenerated cellulose membrane bag (Spectrum Laboratories, 1 kDa MWCO) against 0.01N HCl followed by mQ water, frozen, and lyophilized to give a white powder.

N1 (EDA): $^1$H NMR (400 MHz, D2O) δ 4.74 (s, 1H), 3.56 (s, 2H), 3.19 (s, 2H), 2.88 (s, 2H).

N2 (DET): $^1$H NMR (400 MHz, D2O) δ 4.71 (s, 1H), 3.45 (s, 2H), 3.22 (s, 2H), 3.11 (s, 2H), 2.97 (s, 2H), 2.83 (s, 2H).

N3 (TET): $^1$H NMR (400 MHz, D2O) δ 3.70-3.50 (m, 7H), 3.49-3.41 (m, 2H), 3.35 (s, 2H), 3.23-2.62 (m, 4H).

N4 (TEP): $^1$H NMR (400 MHz, D2O) δ 4.72 (s, 1H), 3.64-3.39 (m, 9H), 3.37-3.05 (m, 5H), 3.00-2.62 (m, 4H).

$^1$H NMR spectra were obtained in CDCl3, dimethyl sulfoxide-d$_6$ or deuterium oxide (Cambridge Isotope Laboratories) using a Bruker Avance 400 MHz NMR spectrometer at 25° C.

Generation of Lentiviral Vectors and Stable Cell Lines pHIV-d2GFP was generated by replacing EGFP in pHIV-EGFP (Welm, B E et al. (2008) *Cell Stem Cell* 2(1):90-102) with a destabilized variant, d2GFP (Clontech, Mountain View, Calif., USA). For construction of the miR-34a reporter vector, 2 repeats of miR-34a binding sites were cloned into pHIVd2EGFP using BamH I and Kpn I. For the human Ago2 overexpression vector, the hAgo2 cDNA amplified from a human cDNA library was cloned into a pFUW lentiviral vector (Addgene, Cambridge, Mass., USA) using Xba I and BamH I. The lentiviral vectors were then transfected into HEK293T cells along with the helper plasmids psPAX2 and pMD2.G (Addgene). The viral supernatant was collected 48 hours after transfection and used to infect HEK293T and NIH3T3 for generation of stable cell lines.

Production and Purification of Recombinant Human Ago2

RNA-free hAgo2 was expressed and purified as previously described (Elkayam, E. et al. (2012) *Cell* 150(1):100-10). Briefly, 10 liters of SF9 insect cells infected with baculovirus expressing Strep-sumo-hAgo2 for 72 hours. Initial purification using Strep-Tactin resin (IBA life sciences) was followed by tag removal with TEV protease. RNA-free hAgo2 was separated from the endogenous RNA loaded hAgo2 using a Mono S column and further purified on a superdex 200 increase column concentrated to 0.5 mg/ml and stored at −80° C. in 50 mM Tris, 100 mM KCI and 10% glycerol.

Dynamic Light Scattering (DLS) Measurements of Nanoplexes

5 μg siRNA or siRNA/Ago2 (1:1) complexes were mixed with each polyamine at a 20 to 1 (N/P) ratio in a 50 μl assembly buffer (20 mM HEPES, 150 mM KCI, 2 mM MgCI2, pH 7.4) for 30 min, and then were diluted to 1 ml with 20 mM HEPES as previously described (Troiber, C. et al. (2013) *Eur J Pharm Biopharm* 84(2):255-64). Final siRNA concentration in DLS measurements was 5 μg/ml. Hydrodynamic size was measured using dynamic light scattering (Malvern ZS90 particle analyzer, λ=633 nm). Zeta potential measurements were made using laser Doppler electrophoresis with the Malvern ZS90. From the obtained electrophoretic mobility, zeta potential was calculated by the Smoluchowski equation: $\zeta=4\pi\eta\upsilon/\varepsilon$, where η is the viscosity of the solvent, υ is the electrophoretic mobility, and ε is the dielectric constant of the solvent. To examine how serum proteins affect the stability of nanoplexes, fetal bovine serum (FBS) was added to the mixture to achieve 10% FBS by volume. potential was calculated by the Preparation of Nanoplexes for Transfection Polyamines were dissolved in 10 mM HEPES buffer (pH7.4) and adjusted to 10 mg/ml. For each well of a 96-well plate, siRNA diluted in 5 μl assembly buffer (20 mM HEPES, 150 mM KCI, 2 mM MgCI2, pH 7.4) was mixed with 5 μl assembly buffer containing recombinant Ago2 at the desired molar ratio at room temperature for 30 min. Afterwards, polyamine diluted in 5 μl assembly buffer was added and incubated at room temperature for 15 min prior to transfection. Polyamine was adjusted to obtain a 20:1 N/P ratio for transfection studies. For in vitro transfection of siSTAT3, cells were transfected in serum-free media for 6 hr before supplementation with serum. For other transfection studies, serum-containing media were included from the beginning. For Lipofectamine® RNAiMAX (Thermofisher, Waltham, Mass., USA) and TransIT-X2 (Mirus Bio LLC, Madison, Wis., USA), the final siRNA and miRNA mimics concentration was 25 nM. For polyamines, 100 nM siRNA was used.

Cell Proliferation Assay

Cells were seeded at 20000 cells per well in 96-well plates one day before transfection. 48 hours after transfection, cells in a 96-well plate were incubated with MTT at a concentration of 0.5 mg/mL, at 37° C. for 1 hr. The purple MTT product was solubilized with DMSO and measured at 570 nm using a Tecan plate reader.

Quantitative PCR

Forty-eight hours after transfection, total RNA was extracted by an RNeasy Plus Mini kit (Qiagen, Hilden, Germany) and converted to cDNA with an Ecodry cDNA synthesis kit (Clontech, Mountain View, Calif., USA). cDNA was amplified with a LightCycler® 480 SYBR Green I Master reagent and quantified by a Roche LightCycler 480 Real-Time PCR System. Primer sequences used for detection are available in supporting information. A common 2-ΔΔCT method was applied to data with automatic removal of background fluorescence by the qPCR-associated software. qPCR primers used in this study are provided below in Table 2.

TABLE 2 qPCR primers

| Target | Forward primer | Reverse primer |
|---|---|---|
| Human β actin | TCCCTGGAGAAGAGCTACGA (SEQ ID NO: 13) | AGCACTGTGTTGGCGTACAG (SEQ ID NO: 14) |
| Mouse β actin | TGGCGCTTTTGACTCAGGAT (SEQ ID NO: 15) | GGGATGTTTGCTCCAACCAA (SEQ ID NO: 16) |
| Mouse STAT3 | GGATCGCTGAGGTACAACCC (SEQ ID NO: 17) | GTCAGGGGTCTCGACTGTCT (SEQ ID NO: 18) |
| Human c-MET | TGCAGCGCGTTGACTTATTCATGG (SEQ ID NO: 19) | GAAACCACAACCTGCATGAAGCGA (SEQ ID NO: 20) |
| Human CDK | CAGATGGCACTTACACCCGTG (SEQ ID NO: 21) | GCAGCCCAATCAGGTCAAAGA (SEQ ID NO: 22) |
| Ago2 (D669A) | TTCTACCGCGcCGGTGTCTCTG (SEQ ID NO: 23) | GATGATGCGGGTGGGCTT (SEQ ID NO: 24) |

Western Blot

Cells were lysed in a lysis buffer (20 mM Tris pH 7.5, 150 mM NaCl, 1% Nonidet P-40, 0.5% Sodium Deoxycholate, 1 mM EDTA, 0.1% SDS, protease inhibitors). Proteins were first separated by 4-15% SDS-PAGE and then transferred to a nitrocellulose membrane (ThermoFisher). The membranes were incubated with primary antibodies: anti-tubulin (clone G-8, 1:1000, Santa Cruz), anti-STAT3 (clone 124H6, 1:2000, Cell Signaling), and anti-c-MET (clone D1C2, 1:2000, Cell signaling) in 5% milk/TBS buffer (25 mM Tris pH 7.4, 150 mM NaCl, 2.5 mM KCl) at 4° C. overnight, and then probed for 1 hour with secondary horseradish peroxidase (HRP)-conjugated anti-mouse or anti-rabbit IgG (Santa Cruz). After extensive wash with TBS containing 0.05% Tween-20, the target proteins were detected on membrane by enhanced chemiluminescence (Pierce).

Intracellular Förster Resonance Energy Transfer (FRET)

Ago2 protein was labeled with Cy5-NHS (AAT bioquest, Sunnyvale, Calif., USA) at a 5:1 (dye/protein) molar ratio directly in the protein storage buffer (50 mM Tris, 100 mM KCl and 10% glycerol) at room temperature for one hour. Protein-dye conjugates were separated from free dyes using 0.5 ml Zeba™ Spin Desalting Columns, 7K MWCO (Thermofisher). siRNAs were labeled with fluorescein using a Label IT® nucleic acid labeling kit (Mirus Bio LLC) at a 10:1 (dye:mRNA) molar ratio per the provider's instruction. Labeled RNAs were purified by ammonia acetate/ethanol precipitation. In a 96-well plate, 104 HEK293T were seeded in 100 μl growth medium per well 24 hours before transfection. On the day of transfection, FITC-siRNA (100 nM final concentration) alone or 100 nM FITC-mRNA/Cy5-Ago2 (1:1 siRNA:Ago2 molar ratio) were transfected with polyamines at N/P 20 into cells. Cells were harvested at 24, 48 and 72 hours posttransfection. Fluorescence intensity of the cells was monitored and evaluated with a FACSCelesta (BD Biosciences) equipped with Diva software (BD Biosciences), using a 488 laser for excitation and a 695/40 nm filter.

Immunocytochemistry

Transfection and immune staining were performed in Millicell® EZ chamber slides (Milliporesigma, Temecula, Calif., USA). Cells were fixed by 4% formaldehyde in PBS for 15 min, permeabilized by 0.4% Triton X-100 on ice for 10 min, and stained with a rabbit anti-Rab7 antibody (1:400, #9367, Cell signaling) overnight at 4° C. After washing with PBS containing 0.05% Tween-20, cells were stained with an Alexa 568-conjugated goat anti-rabbit antibody (4 μg/ml, #A-11011, ThermoFisher). Nuclei were counterstained with DAPI. Cells were imaged with an Inverted Olympus IX83 microscope equipped with a Hamamatsu ImagEM high sensitivity camera at the Swanson Biotechnology Center (MIT).

Animal Experiments

Mouse care and experimental procedures were performed under pathogen-free conditions in accordance with established institutional guidelines and approved protocols from the MIT Division of Comparative Medicine. For s.c. tumor challenge, we injected 0.5 million B16F10 cells (ATCC) into 7-8 week-old C57BL/6. After tumors reached an average size of ~3 mm (day 7 post tumor inoculation), mice were injected intratumorally four times every three days with nanocomplexes containing 5 μg siRNA against luciferase (negative control), siSTAT3 or siRNA with an equimolar amount of Ago2 in the assembly buffer (20 mM HEPES, 150 mM KCl, 2 mM MgCl2, pH 7.4). The vehicle control group received the assembly buffer only. Each group included eight mice at the start of the treatment. The nanocomplexes were prepared in the same way as in in vitro transfection studies, except that a 50 μl final volume was used for each injection. Tumor size measurements were taken every three days right before each injection and discontinued when some mice in the control groups were euthanized due to large tumor burden. Tumor volume was calculated using V=(L×W×W)/2, where V is tumor volume, W is tumor width, and L is tumor length. Survival studies were completed when the last mouse was euthanized, and a Kaplan-Meier survival curve was plotted to evaluate the efficacies of different treatments.

Immunohistochemistry Staining

Tumor samples were obtained at 48 hours following the last treatment in C57BL/6 mice. Tumors were formalin-fixed for 24 hours and paraffin-embedded afterwards. All formalin fixed paraffin embedded slides were antigen retrieved using heat induced epitope retrieval at 97° C. for 20 minutes using citrate buffer (pH 6). An automated machine (ThermoScientific IHC Autostainer 360) run consisted of: endogenous peroxidase blocking (10 minutes), protein block (30 minutes), primary antibody (60 minutes), labeled polymer (15 minutes) and DAB (10 minutes). The entire IHC was processed by the Swanson Biotechnology Center (MIT). Primary antibodies used for immunohistological staining were: STAT3 (Cell Signalling, Catalog #9139, 1:600 dilution), Ki-67 (BD, Catalog #550609, 1:50 dilution), Cleaved Caspase-3 (Cell Signalling, Catalog #9664, 1:100 dilution). Mouse on Mouse polymer was used a secondary antibody (catalog #MM620. Biocare Medical, Pacheco, Calif., USA). Images were acquired by a Leica Aperio Slide Scanner (Leica Biosystems, Buffalo Grove, Ill., USA) and processed by ImageScope (Leica Biosystems).

Statistical Analysis

All statistical analyses were performed using GraphPad Prism 5.0a for Mac OS X (San Diego, Calif., USA). A one-way ANOVA followed by a Tukey post test or Student's t test was used to determine statistical significance in the studies.

Example 2: Preassembling Double-Stranded Short Interference RNA (ds siRNA) with Ago2Protein Elicited a Much Higher Gene Silencing Effect than Conventional siRNA Delivery Methods Inside Cells This study demonstrates that preassembling Ago2 protein with ds siRNA beforehand results in maximal activation of Ago2-mediated mRNA cleavage and degradation (FIG. 1). These results were surprising and unexpected.

The recombinant Ago2 protein was produced in an insect cell line, SF9, transfected with a baculoviral vector, pFL_SST_hAgo2, which was provided by Prof Leemor Joshua-Tor at Cold Spring Harbor laboratory. The protein was purified by Strep-Tactin® Sepharose resin. Following cleavage by TEV protease, the final version of recombinant protein, Ago2 contains two amino acids (Glycine and Alanine) at the N terminus (in bold letters) and the natural amino acid sequence found in human Ago2 (SEQ ID NO: 1).

20 nM ds siRNA against GFP (siGFP) was transfected, alone or along, with 10 nM or 20 nM Ago2 to achieve 1:0.5 and 1:1 molar ratio, respectively, in (FIG. 2A) HEK293T and (FIG. 2B) NIH3T3 cells, which were modified to stably express GFP. For the transfection, 2 pmole ds siRNA, 2 pmole Ago2, and transfection reagent (according to the manual instruction) were mixed in 15 μl 20 mM HEPES, 150 mM KCl, and 2 mM $MgCl_2$ at room temperature for 30 min. The complex was added into 85 μl cell culture media containing 5000-20000 cells per well in a 96-well plate.

Figure 2A:
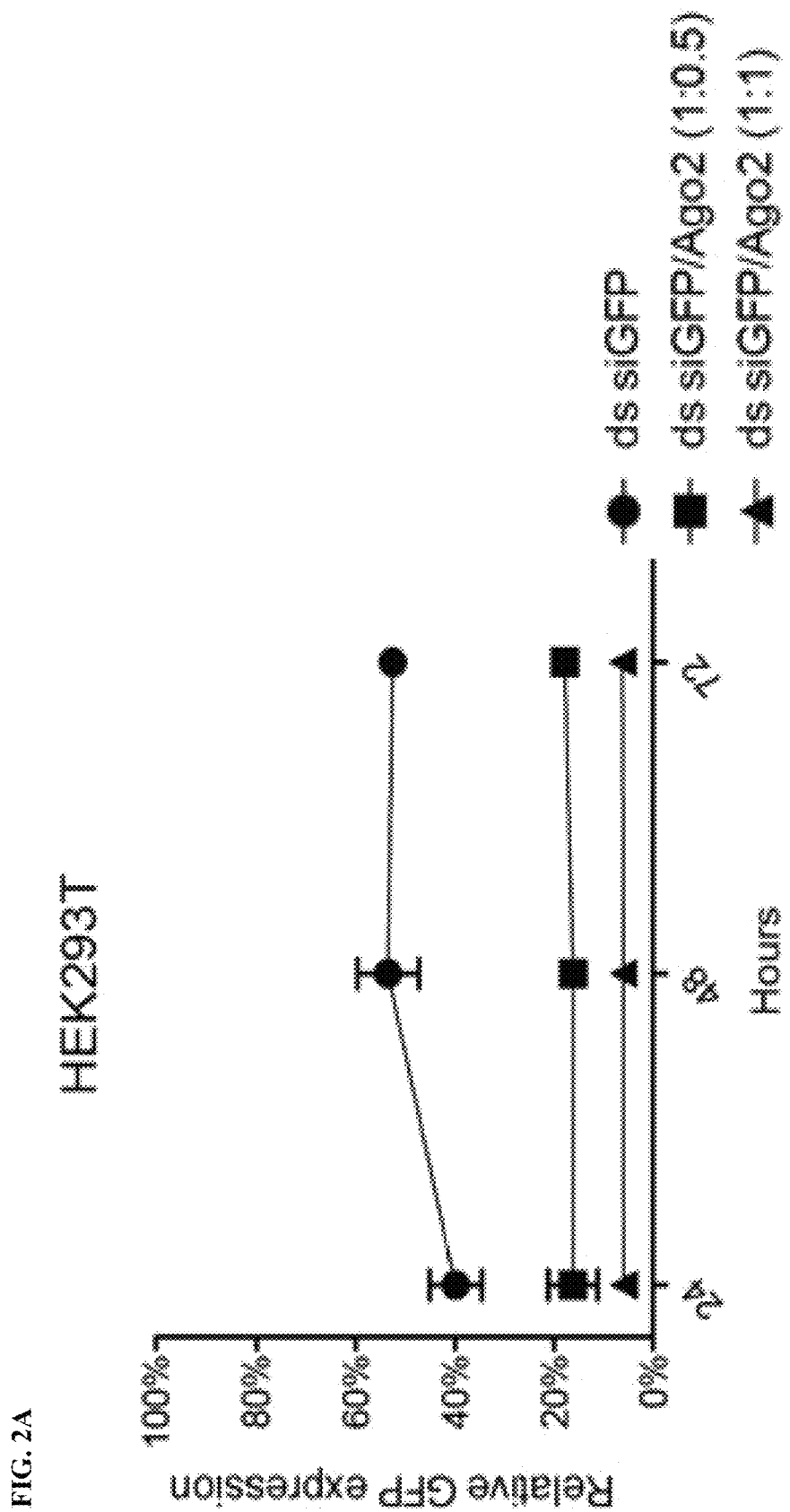
Figure 2B:
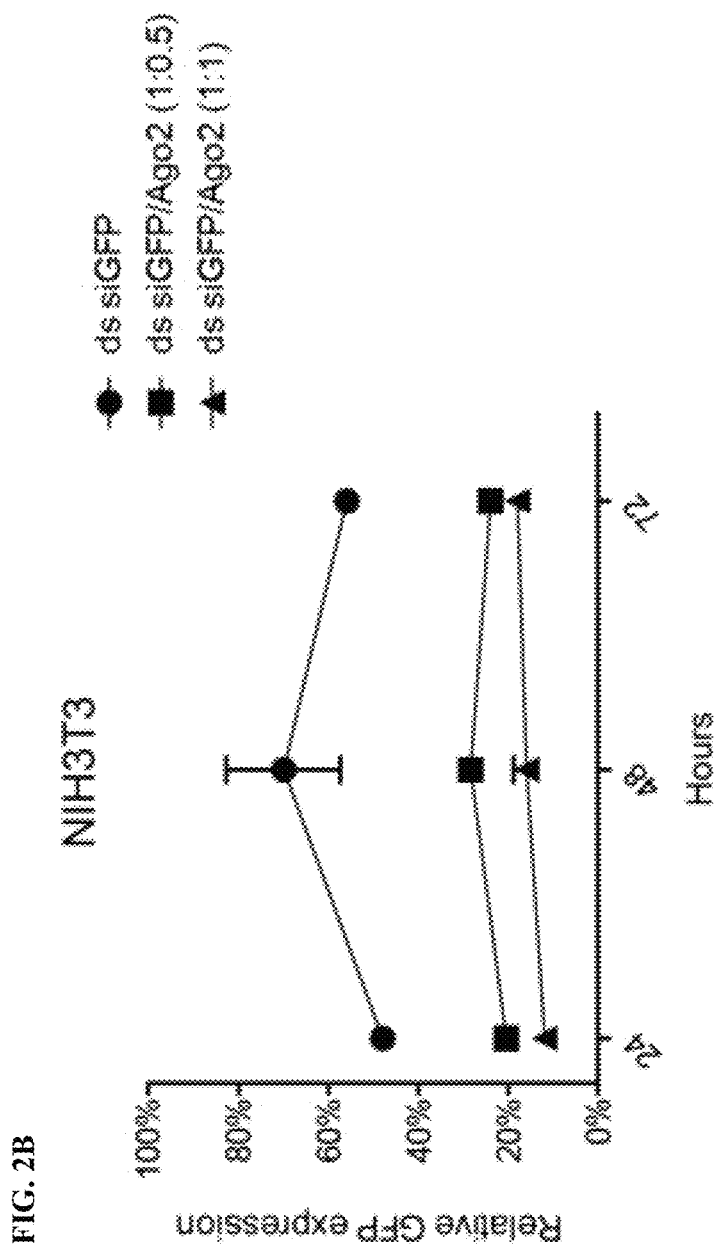
Figure 2D:
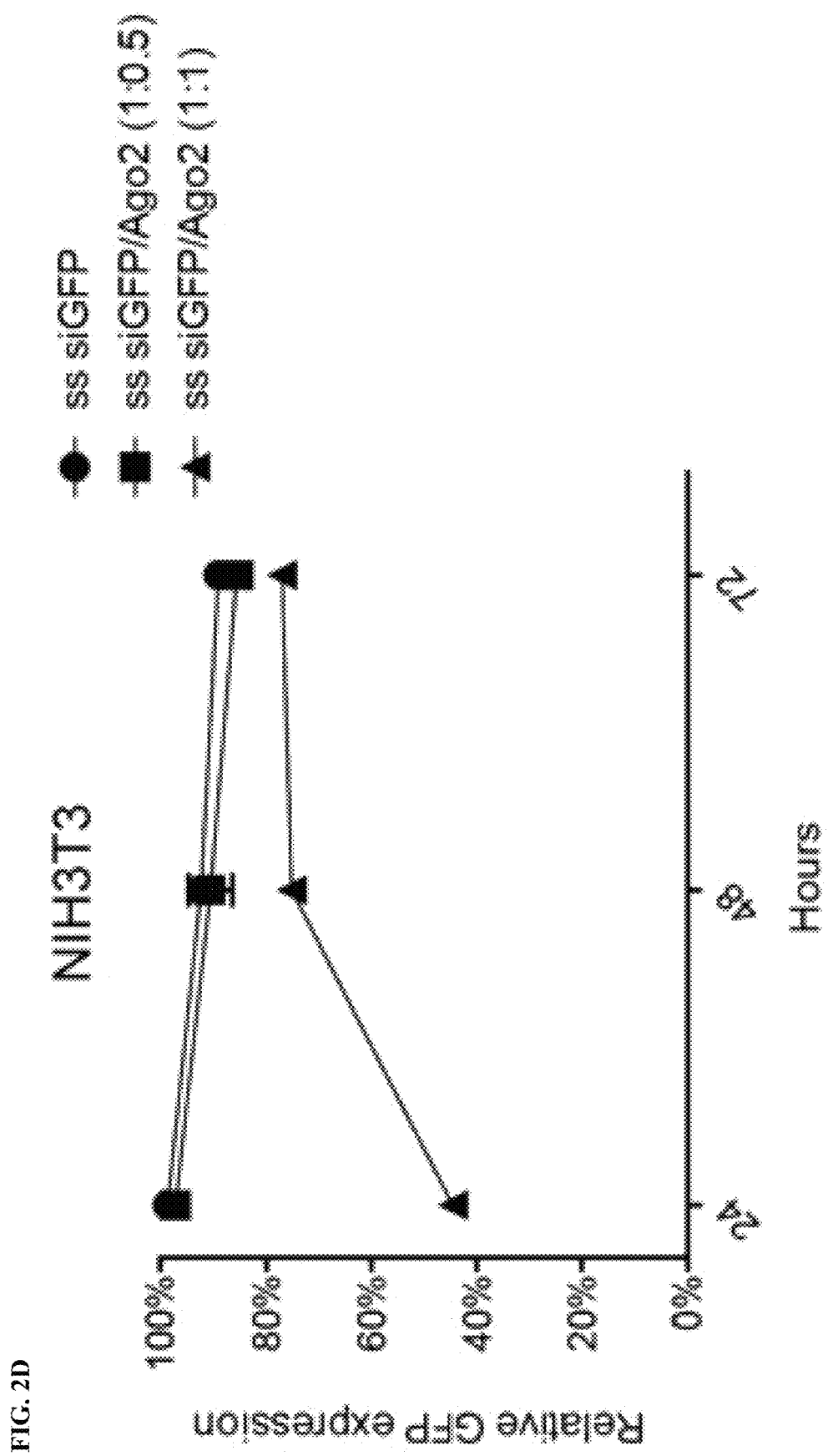

Relative GFP levels were quantified by flow cytometry at 24, 48 and 72 hours post transfection and normalized to non-transfected GFP expressing cells. In contrast, single stranded siRNA against GFP (ss siGFP) alone or along with Ago2 at 1:0.5 and 1:1 molar ratios elicited less efficient gene silencing in (FIG. 2C) HEK293T and (FIG. 2D) NIH3T3 cells. The results depicted in FIG. 2 showed that co-delivering double stranded (ds) siRNA with recombinant Ago2 resulted in superior silencing of GFP expression.

Example 3: Preassembling microRNA34a with Recombinant Ago2 Resulted in Superior Silencing of microRNA34a Targets To test if co-encapsulation of microRNA34a with Ago2 could enhance the silencing of target mRNA expression, a GFP was engineered with a micro34a binding site at 3' untranslated region (UTR) (FIG. 3A), such that GFP expression was decreased by delivery of microRNA34a.

The recombinant Ago2 protein and transfection conditions utilized are described in Example 1.

20 nM microRNA34a was transfected, alone or along, with 10 nM or 20 nM Ago2 to achieve 1:0.5 and 1:1 molar ratios, respectively, in HEK293T cells, which were modified to express GFPmicroRNA34a binding site. Relative GFP levels were quantified by flow cytometry at 24, 48, 72 and 96 hours post transfection (FIG. 3B).

To test if co-delivery of Ago2 could improve the silencing of endogenous microRNA34a targets, 20 nM microRNA34a was transfected, alone or along, with 10 nM Ago2 at 1:0.5 into ovarian cancer cells, OVCAR8. Co-delivery of Ago2 resulted in ~3-fold silencing of the microRNA34a target, CDK4, compared to traditional delivery of microRNA34a alone (FIG. 3C). The specificity was confirmed by using a control ds siRNA that has the same "A, T, C and G" composition as the siRNA of interest (e.g., microRNA34a) but bears a scrambled sequence that is predicted not to target any endogenous mRNA computationally. For example, the miRctl shown in FIG. 3C is the scrambled control siRNA. As expected, miRctl did not affect relative CDK4 mRNA levels, alone or when provided with Ago2. Moreover, co-delivering microRNA34a with recombinant Ago2 unpredictably and remarkably resulted in superior silencing of the microRNA34a target (FIG. 3C). Thus, microRNA34a may represent a promising inhibitor for various cancers and is currently undergoing clinical trials.

Example 4: Double-Stranded siRNA/Ago2 Complex is More Potent than Single-Stranded siRNA/Ago2

Human 293T cells were genetically modified to stably express a destabilized version of green fluorescence protein (d2GFP) with a short half-life relative to enhanced GFP, which allows for fast readout of GFP silencing at the mRNA level (Bu P et al. (2013) *Cell Stem Cell* 12:602-615). Meanwhile, recombinant RNA-free human Ago2 protein was produced from SF9 insect cells and purified to homogeneity using a well-established protocol (FIG. 4A) (Elkayam E et al. (2012) *Cell* 150:100-110). Next, it was examined whether transfection of single-stranded anti-GFP siRNA (ss siGFP)/Ago2 complexes was more potent than ss siGFP alone in knocking down GFP expression via commercial transfection reagents. Delivery of ss siGFP with the commercial transfection agent TransIT-X2 led to little to no silencing (FIG. 5A and FIG. 5C). On the other hand, transfection of ss siGFP and Ago2 complexes using TransIT-X2 significantly enhanced GFP silencing compared with the corresponding ss siRNA alone in 293T cells (FIG. 5A and FIG. 5C). However, since the majority of existing siRNA-based therapeutics employ double-stranded siRNA (ds siRNA), the preassembly of ds siRNA and Ago2 was further tested. It was found that ds siGFP/Ago2 induced greater reduction of GFP expression than ds siGFP alone or ss siGFP/Ago2 (FIG. 5B and FIG. 5D). On the contrary, anti-luciferase siRNA (ss siLuc and ds siLuc) alone or along with Ago2 failed to silence GFP expression, ruling out the possibility of non-specific gene knockdown due to cotransfection of Ago2 protein (FIG. 4B and FIG. 4C). It was deduced that the relative low efficacy of ss siGFP alone or codelivered with Ago2 may result from lower stability of ss siRNA in the cytoplasm relative to ds RNA, leading to reduced formation of cytoplasmic RNA-induced silencing complex (RISC) (Raemdonck K et al. (2006) *Biochemistry* 45:10614-10623).

In addition to targeting the internal coding sequence of genes via siRNA, preassembly of Ago2 with miRNA mimics, which represent another class of RNAi-based therapeutics, were also tested. To this end, miR34a-binding sites were inserted into the 3' untranslated region of GFP to examine gene silencing mediated by the tumor suppressor miR34a (FIG. 6A) (Bu P et al. (2013) *Cell Stem Cell* 12:602-615). Delivery of ds miR34a mimics along with Ago2 significantly reduced GFP expression compared with miR34a mimics alone. Notably, at 96-h posttransfection, the GFP silencing from transfection of miR34a had nearly disappeared, while sustained silencing was still detectable in the cells transfected with miR34a/Ago2 complexes (FIG. 6B). In contrast, a scramble control miRNA mimic did not result in GFP knockdown regardless of cotransfection of Ago2 protein (FIG. 6C). Furthermore, it was confirmed that miR34a/Ago2 complexes were able to silence oncogenes, c-MET and CDK4, endogenous targets of miR34a, in OVCAR8 ovarian cancer cells (FIG. 5E, FIG. 5F, FIG. 6D). Therefore, preassembly of ds siRNA or miRNA mimics along with Ago2 represents a promising strategy to improve the potency of RNAi, which targets either coding or non-coding sequences.

In addition to TransIT-X2, it was confirmed that a lipid-based siRNA transfection reagent, Lipofectamine RNAiMAX, was able to successfully deliver ds siGFP/Ago2 complexes with enhanced RNAi over ds siGFP alone in 293Td2GFP cells (FIG. 7A). Nevertheless, a third lipid-based commercial siRNA transfection reagent, Stemfect®, failed to enhance GFP silencing via codelivery of ds siGFP/Ago2 (FIG. 7B). In general, there are clear indications that the efficacy of the coassembled structures is strongly dependent on the type of agent used for transfection.

Example 5: The Polyamine Side-Chain Structure Modulates the Activity of siRNA/Ago2 Complexes To define the rules that govern the coassembly and resulting gene-silencing efficiency, a series of structurally defined cationic polypeptides for the preassembly of ds siRNA/Ago2 was defined, which will be referred to as siRNA/Ago2 for the rest of this study. These polypeptides were derived using N-carboxyanhydride polymerization of L-benzyl aspartate, followed by exhaustive amination of the side chain with various N-amine substituents bearing one to four aminoethylene repeats in the side chain (FIG. 8A and FIG. 9). Therefore, keeping the same backbone while using distinct side-chain structures enables in-depth characterization of synthetic gene carrier assisted assembly and delivery of siRNA/Ago2 complexes. Moreover, these polypeptides have demonstrated superior transfection efficacy for mRNA and DNA delivery with minimal cytotoxicity in vitro and in vivo (Aini H et al. (2016) *Sci Rep* 6:18743; Lin C Y et al. (2016) *J Control Release* 235:268-275; Li J et al. (2017) *ACS Nano* 11:2531-2544; Li J et al. (2017) *Angew Chem Int Ed Engl* 56:13709-13712).

As shown in FIGS. 8B-8D, at an N/P ratio of 20:1 (number of protonatable amines in the polyamine relative to number of phosphates in siRNA), preassembly of siGFP/Ago2 using the polyamine series as delivery agents resulted in enhanced GFP silencing in 293Td2GFP cells compared with siGFP alone, whereas ss siLuc and ds siLuc alone or with Ago2 failed to knock down GFP expression irrespective of the polyamines under the study (FIG. 10). Interestingly, it was observed that the degree of GFP silencing in siGFP/Ago2-transfected cells was proportional to the number of amine groups on the polyamine side chain, even though the N/P ratio was kept the same across all four polyamine carriers. In addition, enhanced gene knockdown was observed by titrating concentrations of siGFP or siGFP/Ago2 from 50 to 200 nM in 293Td2GFP cells (FIG. 11). It was reasoned that the cationic charge density on the polyamine side chain is associated with the number of amine groups and degree of protonation at a given pH. Additionally, the degree of protonation is affected by the spacing between two neighboring amine groups, as protonation of neighboring amines on the 1,2-diaminoethane moiety ($-NH_2CH_2CH_2NH_2-$) is thermodynamically unfavorable due to electrostatic repulsion (Uchida H et al. (2014) *J Am Chem Soc* 136: 12396-12405; Uchida H et al. (2011) *J Am Chem Soc* 133:15524-15532). Consequently, at neutral pH, when gene silencing occurs in the cytoplasm, the charge unit on the polyamine side chain can be estimated as shown in FIG. 8A, which was found to be positively correlated with the increase in GFP silencing via preassembly of siGFP/Ago2. Such speculation can be corroborated by measurements of the sizes and zeta potentials of siRNA and siRNA/Ago2 complexed with polyamines, where increases in surface charge and condensation ability were observed from N1 (EDA) to N4 (TEP) under physiological conditions (FIG. 12). Moreover, it was found that at N/P 20, siRNA and siRNA/Ago2 did not induce cytotoxicity in immortalized fibroblast cells, which make up the majority of cell types found in many tissues, nor did the inclusion of Ago2 affect cell proliferation compared with siRNA transfection alone (FIG. 13).

To further confirm whether protonated amine groups on the side chain play a role in modulating siRNA/Ago2 activity, an additional methylene group on the side chain of N2 (DET) was introduced to generate a side chain with 1,3-diaminopropylene ($-NHCH_2CH_2CH_2NH_2$), referred to as N2 (DPT) herein. According to a previous finding, increased spacing between two protonatable amines in propylene compared with in ethylene repeat units reduces charge repulsion when both amines are protonated (Miyata K et al. (2008) *J Am Chem Soc* 130:16287-16294). Consequently, N2 (DPT) exhibits a higher degree of protonation (~88%) at pH 7.4, compared with N2 (DET), with nearly half the side-chain amines protonated based on potentiometric titration. Interestingly, as shown in FIG. 8E, N2 (DPT) enabled stronger GFP silencing than N2 (DET) when cotransfecting siGFP/Ago2, whereas siRNA against luciferase failed to silence GFP expression with Ago2 and N2 (DPT). Therefore, N2 (DPT) improves gene silencing likely through increased electrostatic interactions with siRNA and Ago2.

Example 6. Preassembly of siRNA/Ago2 is Indispensable for Sustained Gene Silencing Since Ago2 is considered the rate-limiting factor in the RNAi pathway, previous studies have exploited Ago2 overexpression in targeted cells to enhance gene silencing (Diederichs S et al. (2008) *Proc Natl Acad Sci USA* 105:9284-9289; Borner K et al. (2013) *Nucleic Acids Res* 41:e199). It was investigated whether the physical preclustering of siRNA/Ago2 complex or the restoration of stoichiometric amounts of Ago2 within cells resulted in greater gene silencing (FIG. 14A). To test the latter possibility, 293Td2GFP cells were genetically modified to stably overexpress Ago2 using lentivirus. siGFP was subsequently transfected into these cells via each of the four different polyamines. At 24-h posttransfection, GFP expression was reduced in Ago2-overexpressing cells, with all four polyamines. In addition, during the first 24 h, the degree of GFP silencing with Ago2 overexpression was higher than that with siGFP/Ago2 complexes in 293Td2GFP cells for N1 (EDA), N2 (DET), and N3 (TET) (FIG. 14B). This trend reversed at longer times, and at 48- and 72-h posttransfection, codelivering siGFP/Ago2 complexes outcompeted Ago2 overexpression in downregulating GFP levels via N3 (TET) and N4 (TEP) (FIG. 14C and FIG. 14D). On the contrary, siRNA against luciferase (siLuc) failed to silence GFP expression through codelivery of Ago2 protein or in the presence of Ago2 overexpression, suggesting sequence specific knockdown by siGFP/Ago2 with different polyamines (FIG. 10).

To rule out the possibility that overexpressing Ago2 via the lentiviral system may not have increased Ago2 to the same levels as direct delivery of Ago2 protein, we monitored the total Ago2 levels in cells upon delivery of preassembled siRNA/Ago2 (1:1 molar ratio) packaged with N4 (TEP) over 72 h by Western blotting. The amount of Ago2 protein added into culture medium relative to the cell number in Western blotting assays remained the same as in the in vitro transfection studies as shown in FIG. 8. Unexpectedly, the amount of Ago2 introduced into cells through delivery of siRNA/Ago2 complexes was nearly undetectable compared with in cells transfected with siRNA alone. Moreover, the Ago2 level in cells stably overexpressing this gene far exceeded that of basal Ago2 expression in siRNA/Ago2-transfected cells (FIG. 14E). Therefore, simply raising the level of Ago2 inside cells does not explain the improved gene silencing achieved via preassembly of siRNA/Ago2. Furthermore, codelivery of siRNA and Ago2 protein is likely a prerequisite for enhancement of siRNA-mediated gene silencing. It was hypothesized that strong electrostatic interactions between the positively charged polypeptide used as a carrier and the negatively charged siRNA/Ago2 complexes lead to nanoplexed structures that keep the nucleic acid and protein stably bound for extended periods, thus improving the trafficking of siRNA in a prebound form for gene silencing (FIG. 14A).

Example 7: The Side Chains of Polyamines Modulate Nanoscale Distances that Define Functional Assembly of siRNA and Ago2

Endogenous small RNA species such as miRNAs are abundant inside cells and can potentially compete with delivered siRNA for cotransfected Ago2 proteins (Elkayam E et al. (2012) *Cell* 150:100-110). Therefore, it was reasoned that physical stabilization of the siRNA preassembly with Ago2 when packaged in the nanocomplexes is critical for maintaining the assembled system during intracellular trafficking ultimately to the target mRNA. To address whether polyamines differentially modulate the physical interactions between siRNA and Ago2 inside nanocomplexes, siRNA and Ago2 protein were labeled with fluorescein isothiocyanate (FITC) and cyanine 5 (Cy5), respectively. In principle, when these two dyes are in close vicinity to each other (<10 nm), Förster resonance energy transfer (FRET) can be detected by flow cytometry. Consequently, an intracellular FRET assay is able to quantitatively evaluate the proximity between Ago2 and siRNA following cotransfection into an intracellular environment (FIG. 15A). By longitudinally measuring mean FRET intensity, it was found that the number of charged amine groups on the side chain is proportional to the degree of colocalization between FITC-siRNA and Cy5-Ago2 over the course of 72 h after transfection of 293T cells (FIGS. 15B and 15C). Interestingly, this observation correlated with the ability of the polyamines to enhance siRNA-mediated GFP silencing and to maintain it for extended periods (FIG. 8B-8D). Therefore, the results herein suggest that in addition to facilitating cellular uptake, polyamines with distinct sidechain structures also serve to impact the assembly and activity of siRNA/Ago2, which is critical for Ago2-mediated enhancement of gene silencing.

Example 8: The mRNA Cleavage Activity of Ago2 is Primarily Responsible for Enhanced Gene Silencing Among the four Ago members in mammalian cells, only Ago2 is able to cleave target mRNA (Wang B et al. (2009) *Nat Struct Mol Biol* 16:1259-1266). To test whether its intrinsic endonuclease activity was required for enhancing siRNA-mediated knockdown, a catalytically inactive mutant, Ago2 (D669A), was generated (FIG. 16A) (Tan G S et al. (2009) *Nucleic Acids Res* 37:7533-7545). It was found that the slicing deficiency fully abolished the enhancement of siGFP-mediated silencing using N1 (EDA), N2 (DET), and N3 (TET) (FIG. 10B). Interestingly, with N4 (TEP), the mutant Ago2 protein slightly increased siGFP-mediated silencing in comparison with siGFP alone but to a much lower degree than the wild-type Ago2 (FIG. 10B). According to previous work, the endonuclease-inactive Ago2 (D669A) protein remains able to bind ds siRNA and repress mRNA translation through the miRNA pathway (Tan G S et al. (2009) *Nucleic Acids Res* 37:7533-7545; Liu J et al. (2004) *Science* 305:1437-1441). Therefore, given the fact that N4 (TEP) induced the strongest clustering of siRNA/Ago2 in the cytoplasm based on the FRET studies, it was reasoned that Ago2 (D669A)/N4 (TEP) likely represses mRNA translation despite lower gene-silencing efficiency compared with direct mRNA cleavage.

Example 9: Preassembly of Ago2 with siRNA Against Oncogenes in Melanoma Cells

Having confirmed the silencing potency of siRNA/Ago2 with GFP, a therapeutic target, STAT3, was chosen as its overexpression has been associated with malignancy (Yu H et al. (2009) *Nat Rev Cancer* 9:798-809; Pan Y et al. (2017) *Oncogene* 36:1069-1079). An experimentally validated anti-STAT3 siRNA (siSTAT3) sequence from published studies (Kortylewski M et al. (2009) *Nat Biotechnol* 27:925-932; Kortylewski M et al. (2005) *Nat Med* 11:1314-1321) was utilized, and confirmed cytosolic colocalization of FITC-siSTAT3 and Cy5-Ago2 in B16F10 cells at 24 h after N4 (TEP)-mediated transfection (FIG. 17A). Additionally, the majority of siRNA/Ago2 nanoplexes escaped from late endosomes and lysosomes, as evidenced by imaging Cy5-labeled Ago2 and immune staining against Rab7, a marker for late endocytosis, at 24-h posttransfection with N4 (TEP) (FIG. 18). Next, siSTAT3 was transfected alone or codelivered with Ago2 via N4 (TEP) into B16F10 cells. Enhanced STAT3 knockdown through siSTAT3/Ago2 was observed at both the mRNA and protein levels (FIG. 17B and FIG. 17C). In addition to enhanced target gene knockdown, it was asked whether this could translate into cancer inhibition. A single transfection of siSTAT3 along with Ago2 and N4 (TEP) induced pronounced growth inhibition of melanoma cells for up to 5 d, whereas siSTAT3 with N4 (TEP) failed to do so (FIG. 17D). Such an observation can be corroborated by an earlier study that reported a half-life of greater than 5 d for Ago2 (Olejniczak S H et al. (2013) *Proc Natl Acad Sci USA* 110:157-16). Additionally, it was speculated that such an increased proliferation inhibition resulted from a more stabilized siRNA/Ago2 complex through N4 (TEP) in the cytoplasm of B16F10 cells, which was demonstrated in the aforementioned GFP silencing and FRET studies (FIGS. 8B-8D and FIG. 15).

Example 10: Delivery of siSTAT3/Ago2 Reduces Tumor Burden and Increases Survival in a Melanoma Mouse Model Having confirmed the in vitro efficacy of siSTAT3/Ago2 with N4 (TEP), the synergistic preassembly in a well-established mouse melanoma model was investigated. C57BL/6 mice were challenged with B16-F10 tumor cells on day 0 and, after primary tumor establishment, N4 (TEP)-packaged siSTAT3 and siSTAT3/Ago2 (along with corresponding control siRNA) were injected at 5 µg siRNA per tumor on days 7, 10, 13, and 16 (FIG. 19A). The tumor size was measured every 3 d and used as an indication of cancer progression.

Treatment with siSTAT3/Ago2 significantly reduced tumor burden and prolonged animal survival relative to control groups (FIG. 19B and FIG. 19C). To understand the underlying mechanisms, the same treatment was administered four times to separate batches of mice. Two days after the last treatment, tumor derived samples were stained for STAT3 expression as well as with two markers for cell proliferation (Ki67 positive) and apoptosis (active caspase 3 positive). Consistent with the tumor measurements and survival study, only siSTAT3/Ago2-treated tumors resulted in reduced STAT3 expression (FIG. 19D). In addition, the inhibitory effect of siSTAT3/Ago2 on tumor progression was attributed to decreased cell proliferation, as evidenced by much fewer Ki67-positive nuclei (FIG. 19D). In contrast, the staining for cleaved caspase 3, a hallmark of apoptotic cells, showed that delivery of siSTAT3/Ago2 did not appreciably induce cell apoptosis, with a lack of noticeable differences across different treatment regimes (FIG. 19D). Therefore, it was concluded that preassembly of siSTAT3 and Ago2 can potentially exert great therapeutic efficacy by inhibiting cancer cell proliferation.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed:

1. A RNA protein complex (RNP) comprising:
(a) a non-native, short double-stranded RNA (dsRNA), or non-native analog thereof; and
(b) a recombinant Argonaute 2 protein (Ago2), wherein said Ago2 comprises:
(i) a polypeptide having 100% sequence identity to the amino acid sequence set forth in SEQ ID NO: 1, or
(ii) a polypeptide having at least 97% sequence identity to the amino acid sequence set forth in SEQ ID NO: 3; and
(c) a polyamine comprising a repeat unit represented by the following structural formula:

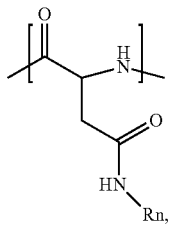

wherein Rn=

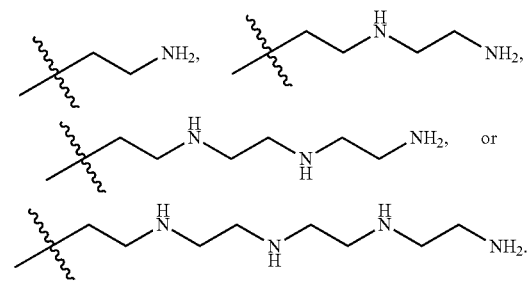

2. The RNP of claim 1, wherein said polypeptide of (ii) has 100% sequence identity to the amino acid sequence set forth in SEQ ID NO: 3.

3. The RNP of claim 1, wherein said dsRNA is selected from the group consisting of:
(a) small interfering RNA (siRNA or ds siRNA);
(b) small hairpin RNA (shRNA);
(c) microRNA (miRNA);
(d) Piwi-interacting RNA (piRNA);
(e) heterochromatin-related guide RNAs (hc-gRNA); and
(f) antigene RNAs (agRNA).

4. The RNP of claim 3, wherein the dsRNA is miRNA.

5. The RNP of claim 4, wherein the miRNA is microRNA34a.

6. The RNP of claim 1, wherein said dsRNA is 45-50 nucleotides in length.

7. The RNP of claim 1, wherein said dsRNA comprises at least one phosphate-sugar backbone modification.

8. The RNP of claim 7, wherein the at least one phosphate-sugar backbone modification is selected from the group consisting of:
(a) phosphorothioate linkage;
(b) phosphoramidate linkage;
(c) phosphodithioate linkage;
(d) chimeric methylphosphonate-phosphodiester linkage; and
(e) 5'-N-phosphoramidite linkage.

9. The RNP of claim 1, wherein the dsRNA comprises a silencing sequence.

10. The RNP of claim 9, wherein said silencing sequence comprises one, two, three, four, or five nucleotide basepair mismatch.

11. The RNP of claim 10, wherein said analog comprises at least one nucleoside selected from the group consisting of:
(a) 2-aminoadenosine;
(b) 2-thiothymidine;
(c) inosine;
(d) pyrrolo-pyrimidine;
(e) 3-methyl adenosine;
(f) C5-propynylcytidine;
(g) C5-propynyluridine;
(h) C5-bromouridine;
(i) C5-fluorouridine;
(j) C5-iodouridine;
(k) C5-methylcytidine;
(l) 7-deazaadenosine;
(m) 7-deazaguanosine;
(n) 8-oxoadenosine;
(o) 8-oxoguanosine;
(p) O(6)-methylguanine; and
(q) 2-thiocytidine.

12. The RNP of claim 1, for use in silencing the expression of a target gene, wherein the use comprises introducing the RNP into a cell.

13. The RNP of claim 1, for use in gene silencing in a subject, wherein the use comprises administering a therapeutically effective amount of the RNP to the subject.

14. The RNP of claim 1, wherein said dsRNA is 40-45 nucleotides in length.

15. The RNP of claim 1, wherein said dsRNA is 35-40 nucleotides in length.

16. The RNP of claim 1, wherein said dsRNA is 30-35 nucleotides in length.

17. The RNP of claim 1, wherein said dsRNA is 25-30 nucleotides in length.

18. The RNP of claim 1, wherein said dsRNA is 20-25 nucleotides in length.

19. The RNP of claim 1, wherein said dsRNA is 15-20 nucleotides in length.

20. The RNP of claim 1, wherein said dsRNA is 10-15 nucleotides in length.

21. The RNP of claim 1, wherein the RNP has a N/P ratio (number of protonatable amines in the polyamine relative to number of phosphates in siRNA) is 20:1.

22. A method for silencing the expression of a target gene in a cell, comprising:
  (i) providing a non-native, short double-stranded RNA (dsRNA), or non-native analog thereof;
  (ii) complexing the dsRNA to a recombinant Argonaute 2 protein (Ago2); wherein said Ago2 comprises: (a) a polypeptide having 100% sequence identity to the amino acid sequence set forth in SEQ ID NO: 1, or (b) a polypeptide having at least 97% sequence identity to the amino acid sequence set forth in SEQ ID NO: 3; and a polyamine comprising a repeat unit represented by the following structural formula:

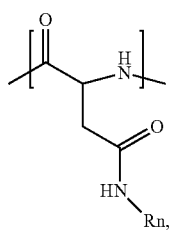

wherein Rn=

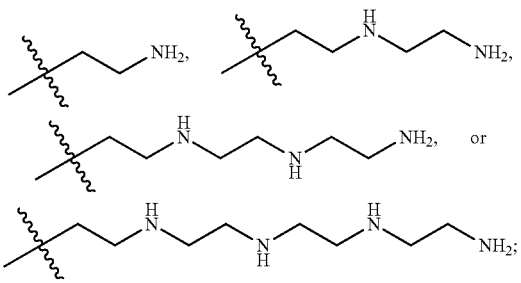

(iii) forming an Ago2 protein-dsRNA complex (RNP) comprising the dsRNA and the Ago2; and
  (iv) introducing the RNP into the cell;
thereby inducing gene silencing of the target gene.

23. The method of claim 22, wherein the RNP comprises a 1:0.5 or 1:1 ratio of dsRNA to Ago2.

24. The method of claim 22, wherein the cell is a stem cell or an embryonic stem cell.

25. The method of claim 22, wherein the cell is in culture.

* * * * *